United States Patent [19]
Aoki et al.

[11] Patent Number: 5,719,291
[45] Date of Patent: Feb. 17, 1998

[54] CYCLOHEXANE DERIVATIVES

[75] Inventors: Yuhko Aoki, Chigasaki; Hiromichi Kotaki; Kazunao Masubuchi, both of Yokohama; Toru Okuda, Fujisawa; Nobuo Shimma, Chigasaki; Takuo Tsukuda; Isao Umeda, both of Yokohama, all of Japan

[73] Assignee: Hoffmann-La Roche Inc., Nutley, N.J.

[21] Appl. No.: 433,007

[22] Filed: May 3, 1995

Related U.S. Application Data

[62] Division of Ser. No. 911,853, Jul. 10, 1992, Pat. No. 5,449,785.

[30] Foreign Application Priority Data

Jul. 24, 1991 [EP] European Pat. Off. .............. 91112370
Aug. 14, 1991 [EP] European Pat. Off. .............. 91113621
Jun. 22, 1992 [EP] European Pat. Off. .............. 92110497

[51] Int. Cl.⁶ .................... C07D 405/04; C07D 309/04
[52] U.S. Cl. .................... 548/262.2; 548/345.1; 548/311.1; 549/216; 549/332; 549/396; 549/398; 549/399; 549/416; 549/417
[58] Field of Search .............. 548/262.2, 345.1, 548/311.1; 549/216, 332, 396, 398, 399, 416, 417; 564/193, 462; 568/670; 562/400

[56] References Cited

U.S. PATENT DOCUMENTS

| | | | |
|---|---|---|---|
| 4,252,742 | 2/1981 | Blackwell, III et al. | 564/447 |
| 4,920,138 | 4/1990 | Ito et al. | 514/383 |
| 4,952,604 | 8/1990 | Hensens et al. | 548/262.2 |
| 5,124,345 | 6/1992 | Ito et al. | 514/383 |
| 5,248,790 | 9/1993 | Treuner | 549/222 |
| 5,266,593 | 11/1993 | Ermann et al. | 514/459 |
| 5,270,334 | 12/1993 | O'Sullivan et al. | 514/459 |

FOREIGN PATENT DOCUMENTS

| | | |
|---|---|---|
| 061 910 | 10/1982 | European Pat. Off. . |
| 0433780 | 6/1991 | European Pat. Off. . |
| 2132547 | 1/1973 | Germany . |
| 3902031 | 7/1990 | Germany . |
| 5048 | 6/1986 | Japan . |

OTHER PUBLICATIONS

Tetrahedron Letters, vol. 31, No. 22, pp. 3133–3136 (1990).

Nohira, et al, The Resolution and Rotations of trans–2–Aminocyclohexanecarboxylic Acids and Derivatives, Bulletin of the Chemical Society of Japan, vol. 43, No. 7, pp. 2230–2233, (1970).

G. Knupp, et al, Synthese und absolute Konfiguration 2–substituierter Cyclohexanamine, Chemische Berichte, vol. 117 No. 6, pp. 2076–2098 (1984).

Todd Cochran, et al, The Use of Nuclear Magnetic Resonance as a Monitor in Optical Resolutions. II. The Synthesis and Resolution of cis–and trans–2–(o–Bromophenyl)cyclohexylamines, The Journal of Organic Chemistry, vol. 36, No. 20, (1971).

Verbit, et al, Optically Active Aromatic Chromophores, XI¹ Circular Diohroism Studies of Some 1–Substituted 2–Phenylcylohexanes, Journal Of the American Chemical Society, vol. 94, No. 15 (1972).

Chemical Abstracts, vol. 95:220155f (1981).

Chemical Abstracts, vol. 110, No. 13, 110:114264j (1989).

*Primary Examiner*—Joseph McKane
*Attorney, Agent, or Firm*—George W. Johnston; William H. Epstein; Briana C. Buchholz

[57] ABSTRACT

Compounds of the formula

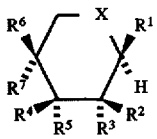

(I)

which have antifungal activity.

30 Claims, No Drawings

CYCLOHEXANE DERIVATIVES

This application is a divisional of Ser. No. 07/911,853 filed Jul. 10, 1992 now U.S. Pat. No. 5,449,785.

BACKGROUND OF THE INVENTION

Tetrahydropyran-3-yl esters produced by the cultivation of the species Penicillium have antifungal activity (U.S. Pat. No. 4,952,604). However, the known tetrahydropyran-3-yl esters are not fully satisfactory as antifungal agents in terms of antifungal activity and stability.

SUMMARY OF THE INVENTION

The present invention relates to novel cyclohexane and tetrahydropyran derivatives, a process for their manufacture, an antifungal composition containing them and the use thereof in combatting fungi.

DETAILED DESCRIPTION OF THE INVENTION

More particularly, the present invention relates to novel compounds represented by formula (I),

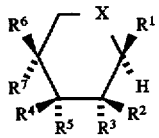

(I)

wherein X is —O— or —CH$_2$—;

R$^1$ is —Y-alkyl, —Y-aralkyl or —Y-aryl where Y is —O—, —CONH—, —NHCO—, —C≡C—, —CH$_2$O—, —CH$_2$S—, or —(CH=CH)$_n$— where n is 0, 1, 2 or 3; or R$^2$ is hydrogen or hydroxy;

R$^3$ is a group capable of coordinating with heme;

R$^4$ and R$^5$ are individually hydrogen, lower alkyl, alkoxy or alkylthio, or can be taken together with the adjacent carbon atom to form a 5- or 6- membered acetal ring;

R$^6$ is hydrogen, lower alkyl, alkoxy or alkylthio, amino, lower alkylamino or di-lower- alkylamino;

R$^7$ is hydrogen, hydroxy, lower alkyl, alkoxy or alkylthio which may be optionally substituted with a hydroxy, an acyl or aryl group, or a 5- or 6-membered heterocyclic ring containing one or more nitrogen atom(s) which may further contain an oxygen or sulfur atom; or R$^6$ and R$^7$ can be taken together with the adjacent carbon atom to form a 5- or 6-membered acetal ring; or R$^2$ and R$^4$, can be taken together to form a single bond, as well as pharmaceutically acceptable salts thereof, and hydrates or solvates of the compounds of the formula (I) or their salts.

As used herein, the term "lower" is intended to mean a carbon chain preferably containing up to and including 7 carbon atoms, unless otherwise indicated.

"Alkyl" preferably means a straight or branched chain alkyl group having 1 to 15 carbon atom(s) such as methyl, ethyl, n-propyl, iso-propyl, n-butyl, iso-butyl, sec-butyl, n-pentyl, iso-pentyl, n-hexyl, iso-hexyl, n-heptyl, n-octyl, n-nonyl, 4,8-dimethylnonyl, n-decyl, n-undecyl, n-dodecyl, n-tridecyl, n-tetradecyl, n-pentadecyl.

"Aralkyl" preferably means an aralkyl group in which the alkylene group between Y and aryl contains 1 to 5 carbon atom(s) such as benzyl, phenethyl, 3-phenyl-propyl, 4-phenylbutyl, 5-phenylpentyl, pyridylmethyl, 2-pyridylethyl, 3-pyridylpropyl, 4-pyridylbutyl, 5-pyridylpentyl, b-naphthyl=methyl, 2-(b-naphthyl)ethyl, 3-(b-naphthyl)propyl, 4-(b-naphthyl)butyl, 5-(b-naphthyl) pentyl, 2-quinolylmethyl, 3-quinolylmethyl, 2-(2-quinolyl) ethyl, 2-(3-quinolyl)ethyl, 3-(2-quinolyl)propyl, 3-(3-quinolyl)propyl, 2-quinoxalinylmethyl, 2-(2-quinoxalinyl) ethyl, 3-(2-quinoxalinyl)propyl.

These aralkyl groups may be optionally substituted in the aromatic ring with 1 or 2 halogen atom(s), hydroxy, di-loweralkylamino, pyrrolidino, piperidino, piperazino, morpholino, lower alkyl or alkoxy groups wherein the alkyl groups may be optionally substituted with one or more halogen atom(s). Especially preferred alkyl groups are benzyl, 4-chlorobenzyl, 4-fluorobenzyl, 2,4-dichlorobenzyl, 2,4-difluorobenzyl, 4-methylbenzyl, 4-ethylbenzyl, 4-propylbenzyl, 4-t-butylbenzyl, phenethyl, 2-(4-chlorophenyl)ethyl, 2-(4-fluorophenyl)ethyl, 2-(2,4-dichlorophenyl)ethyl, 2-(2,4-difluorophenyl)ethyl, 2-(4-methylphenyl)ethyl, 2-(4-ethylphenyl)ethyl, 2-(4-n-propyl-phenyl)ethyl, 3-phenylpropyl, 3-(4-chlorophenyl)propyl, 3-(4-fluorophenyl)propyl, 3-(2,4-dichlorophenyl)propyl, 3-(2,4-difluorophenyl)propyl, 3-(4-methylphenyl)propyl, 3-(4-ethyl-phenyl)propyl, 3-(4 -n-propylphenyl)propyl, 4-phenylbutyl, 4-(4-chlorophenyl)butyl, 4-(4-fluorophenyl) butyl, 4-(2,4-dichloro-phenyl)butyl, 4-(2,4-difluorophenyl) butyl, 4-(4-methylphenyl)-butyl, 4-(4-ethylphenyl)butyl, 4-(4-n-propylphenyl)butyl, 5-phenylpentyl, 5-(4-chlorophenyl)pentyl, 5-(4-methylphenyl)-pentyl, b-naphthylmethyl, 2-(b-naphthyl)ethyl, 3-(b-naphthyl)-propyl, 4-(b-naphthyl)butyl, 5-(b-naphthyl)pentyl, and 2-quinolinyl-methyl.

"Aryl" preferably means phenyl, naphthyl, pyridyl, quinolyl or quinoxalinyl which may be substituted with 1 to more halogen atom(s), hydroxy, lower alkyl, haloalkyl, alkoxy, amino or di-lower alkylamino groups, such as ,phenyl, 4-chlorophenyl, 4-fluorophenyl, 2,4-dichlorophenyl, 2,4-difluorophenyl, 4-trifluoromethylphenyl, 2-fluoro-4-trifluoromethylphenyl, 4-methylphenyl, 4-ethyl-phenyl, 4-propyl-phenyl, 4-t-butylphenyl, pyridyl, 2-naphthyl, 2-quinolinyl, 3-quinolyl, 2-quinazolyl.

A group capable of coordinating with heme is, for example, amino, amino-lower alkyl having 1 to 3 carbon atom(s), 1H-imidazol-1-ylmethyl, 1H-1,2,4-triazol-1-ylmethyl, aminoacetoxy, (aminoacetyl)amino, ((lower-alkylamino) acetyl)amino, ((di-lower-alkylamino)acetyl) amino, (aminomethyl)hydroxyphosphinoyloxy, ((lower-alkylamino)methyl)hydroxyphosphinoyloxy, O-methyl-(aminomethyl)hydroxyphosphinoyloxy, O-methyl-((lower-alkylamino) hydroxyphosphinoyloxy, 3-amino-2-oxopropyl, 3-amino-2-hydroxypropyl, 3-(lower-alkylamino)-2-oxopropyl, 3-(di-lower-alkylamino)-2-oxopropyl, 3-(lower-alkylamino)-2-hydroxypropyl, 3-(di-lower-alkylamino)-2 -hydroxypropyl, 1,3-oxazol-5-ylmethyl. Of these, 1H-imidazol-1-ylmethyl, 1H-1,2,4-triazol-1-ylmethyl, aminoacetoxy, (aminoacetyl)amino (aminomethyl)hydroxyphosphinoyloxy, O-methyl-(aminomethyl)hydroxyphosphinoyloxy, 3-amino-2-oxopropyl, 3 -amino-2-hydroxypropyl, 1,3-oxazol-5-ylmethyl are especially preferred.

Examples of lower alkyl are methyl, ethyl, n-propyl, iso-propyl, n-butyl, iso-butyl, sec-butyl, n-pentyl, iso-pentyl, n-hexyl, iso-hexyl.

Examples of lower alkoxy are methoxy, ethoxy, n-propoxy, iso-propoxy, n-butoxy, iso-butoxy, see-butoxy, n-pentyloxy, iso-pentyloxy, n-hexyloxy, iso-hexyloxy.

Examples of lower alkylthio or alkylthio are methylthio, ethylthio, n-propylthio, iso-propylthio, n-butylthio.

Examples of 5- or 6-membered acetal rings are 1,3-dithiolane, 1,3-dithiane, 1,3-dioxolane or 1,3-dioxane.

Examples of lower-alkylamino are methylamino, ethylamino, n-propylamino, iso-propylamino.

Examples of di-lower-alkylamino are dimethylamino, diethylamino, N-ethylmethylamino.

"Acyl" means an aliphatic or aromatic acyl, preferably aliphatic acyl having 1 to 4 carbon atom(s) such as acetyl, propionyl.

The term "5- or 6-membered heterocyclic ring containing one or more nitrogen atom(s) which may further contain an oxygen or sulfur atom" preferably means morpholino, thiomorpholino, 4-methyl-piperazinyl, imidazol-1-yl, 1H-1,2,4-triazol-1-yl.

The novel compounds of formula (I) can be produced according to the following methods:

Process A:

Compounds represented by formula (I) in which $R^2$ is hydrogen, $R^3$ is an aminoacetoxy or (aminoacetyl)amino group, and $R^1$, $R^4$, $R^5$, $R^6$, $R^7$ and X are as defined above can be produced by acylating a compound of formula (II),

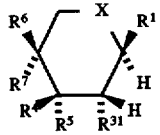
(II)

wherein $R^{31}$ is hydroxy or amino, and $R^1$, $R^4$, $R^5$, $R^6$, $R^7$ and X are as defined above,
with a N-protected glycine or its activated ester, followed by removal of a protecting group.

Process B:

Compounds of formula (I) [in which $R^2$ is a hydrogen atom, $R^3$ is (aminomethyl)hydroxyphosphinoyloxy or O-methyl-(aminomethyl)hydroxyphosphinoyloxy, and $R^1$, $R^4$, $R^5$, $R^6$, $R^7$ and X are as defined above can be produced by reacting a compound represented by formula (II) in which $R^{31}$ is a hydroxy and $R^1$, $R^4$, $R^5$, $R^6$, $R^7$ and X are as defined above with a N-protected-(aminomethyl) phosphonic acid, followed by O-methylation of the resulting phosphonate if desired, and subsequent removal of a protecting radical.

Process C:

Compounds represented by the formula (I) in which $R^2$ is a hydrogen atom, $R^3$ is ((lower-alkylamino)acetyl)amino, ((di-lower-alkyl)acetyl)amino, ((lower-alkylamino)methyl)hydroxyphosphinoyloxy, O-methyl-((lower-alkylamino)methyl)hydroxyphosphinoyloxy, 3-(lower-alkylamino)-2-oxopropyl, 3-(di-lower-alkylamino)-2-oxopropyl, 3-(lower-alkylamino)-2-hydroxypropyl, or 3-(di-lower-alkylamino)-2-hydroxypropyl and $R^1$, $R^4$, $R^5$, $R^6$, $R^7$ and X are as defined above can be produced by N-alkylating a compound of formula (III),

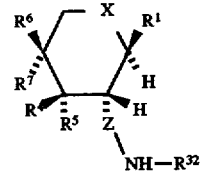
(III)

wherein Z is —NHCOCH$_2$—, —O—PO(OH)CH$_2$—, —O—PO(OCH$_3$)CH$_2$—, —CH$_2$CH(OH)CH$_2$— or —CH$_2$COCH$_2$—, $R^{32}$ is a hydrogen atom or N-protecting group and $R^1$, $R^4$, $R^5$, $R^6$, $R^7$ and X are as defined above, followed, if necessary, by removal of an N-protecting group.

Process D:

Compounds represented by the general formula (I) in which $R^2$ is hydroxy and $R^3$ is an azol-1-ylmethyl group and $R^1$, $R^4$, $R^5$, $R^6$, $R^7$ and X are as defined above can be produced by reacting a compound of formula (IV),

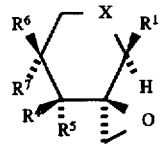
(IV)

wherein R1, R4, R5, R6, R7 and X are as defined above; with an alkali metal salt of imidazole or 1H-1,2,4-triazole.

Process E:

Compounds represented by the formula (I) in which $R^3$ is 1H-imidazol-1-ylmethyl or 1H-1,2,4-triazol-1-ylmethyl, and $R^1$, $R^2$, $R^4$, $R^5$, $R^6$, $R^7$ and X are as defined above can be produced by reacting a compound of formula (V),

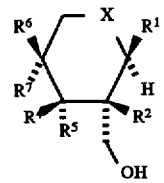
(V)

wherein $R^2$ is a hydrogen, or $R^2$ and $R^4$ can be taken together to form a single bond, and $R^1$, $R^4$, $R^5$, $R^6$, $R^7$ and X are as defined above,
with mesyl chloride, tosyl chloride or triflic anhydride, followed by treatment of the resulting mesylate, tosylate or triflate with an alkali metal salt of imidazole or 1H-1,2,4-triazole.

Process F:

Compounds of formula (I) in which X is a methylene group, $R^2$ is hydrogen, $R^3$ is 3-amino-2-hydroxypropyl, $R^6$ is methyl, and $R^1$, $R^4$, $R^5$ and $R^7$ are as defined above can be produced by reacting a compound of formula (VI),

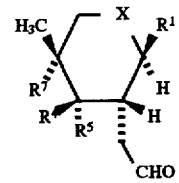
(VI)

wherein $R^1$, $R^4$, $R^5$ and $R^7$ are as defined above, with trimethylsilyl cyanide followed by reduction of the resulting O-protected cyanohydrin to b-amino alcohol.

A process for producing six-membered ring compounds of formula (I) according to the present invention will be explained in more detail in the following examples.

Process A:

Specific examples of the compound represented by formula (II) include, (2S,3R,5R)-5-methyl-2-[(E)-1-nonenyl]tetrahydro-2H-pyran-3-ol, (2S,3R,4S,5S) -5-methyl-2-[(Z)-1-nonenyl]-4-propoxytetrahydro-2H-pyran-3-ol, (2S,3R,4S,5S)-5-methyl-2-[(E)-1-nonenyl]-4-propoxytetrahydro-2H-pyran-3-ol, (2S,3R,4S,5S)-4-ethoxy-5-methyl-2-[(E)-1-nonenyl] tetrahydro-2H-pyran-3-ol, (2S,3R,4S,5S)-5-methyl-2-nonyl-4-propoxytetrahydro-2H-pyran-3-ol, (2S,3R,4R,5S)-4-methoxy-5-methyl-2-[(E)-1-nonenyl] tetrahydro-2H-pyran-3-ol, (2S,3R,4S,5S)-4-methoxy-5-methyl-2-[(E)-1-nonenyl] tetrahydro-2H-pyran-3-ol, (2S,3R,4S,5S)-4methoxy-5-methyl-2-[(Z)-1-nonenyl]tetrahydro-2H-pyran-3-ol, (2S,3R,4S,5S)-4-methoxy-5-methyl-2-nonyltetrahydro-2H-pyran-3-ol, (2S,3R,4S,5S)-2-methoxy-5-methyl-[(E)-decenyl]tetrahydro-2H-pyran-3-ol, (2S,3R,4S,5S)-4-(4,8-dimethylnonyl)-4-methoxy-5-methyl-tetrahydro-2H-pyran-3-ol, (2S,3R,4R,5R)-5-butoxy-4-methoxy-2-[(E)-nonenyl]tetrahydro-2H-pyran-3-ol, (2S,3R,4R,5R)-5-benzyloxy-4-methoxy-2-[(E)-1-nonenyl]tetrahydro-2H-pyran-3-ol, (2S,3R,4S,5R)-4-methoxy-5-methyl-2-nonyltetrahydro-2H-pyran-3-ol, (2S,3R,4S,5R)-4-methoxy-5-methyl-2-[(Z)-1-nonenyl]tetrahydro-2H-pyran-3-ol, (2S,3R,4R,5R)-5-ethoxy-4-methoxy-2-[(E)-1-nonenyl]tetrahydro-2H-pyran-3-ol, (2S,3R,4R,5R)-5-(2,4-difluorobenzyloxy)-4-methoxy-2-[(E)-1-nonenyl]tetrahydro-2H-pyran-3-ol, (9S,10R,11R)-11-methoxy-9-[(E)-1-nonenyl]-8-oxa-1,5-dithiospiro-[5,5]undecan-10-ol, (2S,3R,4R,5S)-4-methoxy-5-methyl-2[(Z)-1-nonenyl]tetrahydro-2H-pyran-3-ol, (2S,3R,4R,5S)-4-methoxy-5-methyl-2-nonyltetrahydro-2H-pyran-3-ol, (2S,3R,4R,5R)-4,5-dimethoxy-2-[(E)-1-nonenyl]tetrahydro-2H-pyran-3-ol, (2S,3R,4S,5S)-4-methoxy-5-methyl-2[(E)-2-(4-propylphenyl)=vinyl]tetrahydro-2H-pyran-3-ol, (2S,3R,4S,5S)-4-methoxy-5-methyl-2-[2-(4-propylphenyl)ethyl]=tetrahydro-2H-pyran-3-ol, (2S,3R,4S,5S)-2-[2-(4-chlorophenyl)enthyl]-4-methoxy-5-methyltetrahydro-2H-pyran-3-ol, (2S,3R,4S,5S)-4-methoxy-5-methyl-2-(2-naphthylethyl)tetrahydro-2H-pyran-3-ol, (2R,3R,4S,5S)-2-[(4-chlorophenylthio)methyl]-4-methoxy-5-methyltetrahydro-2H-pyran-3-ol, (2S,3R,4S,5S)-4-methoxy-5-methyl-2-[4-(4-methylphenyl)butyl]=tetrahydro-2H-pyran-3-ol, (2S,3R,4S,5S)-4-methoxy-5-methyl-2-[(E)-1-octenyl]tetrahydro-2H-pyran-3-ol, (2S,3R,4S,5S)-4-methoxy-5-methyl-2-[(E)-1-undecenyl]tetrahydro-2H-pyran-3-ol, (2S,3R,4S,5S)-2-[(E)-2-(4-ehlorophenyl)vinyl]-4-methoxy-5-methyltetrahydro-2H-pyran-3-ol, (2S,3R,4S,5S)-4-methoxy-5-methyl-2-[(E)-2-naphthylvinyl]=tetrahydro-2H-pyran-3-ol, (2S,3R,4R,5R)-4-methoxy-2-nonyl-5-(3-phenylpropoxy)tetrahydro-2H-pyran-3-ol, (2S,3R,4R,5R)-5-(4-tert-butylbenzyloxy)-4-methoxy-2-[(E)-1-nonenyl]tetrahydro-2H-pyran-3-ol, (2S,3R,4R,5R)-5-(2-hydroxyethoxy)-4-methoxy-2-nonyltetrahydro-2H-pyran-3-ol, (2S,3 R,4S,5S)-4-methoxy-5-methyl-2-(1-nonynyl)tetrahydro-2H-pyran-3-ol, (2S,3R,4S,5S)-2-[(E)-1-heptenyl]-4-methoxy-5-methyltetrahydro-2H-pyran-3-ol, (2S,3R,4S,5S)-2-(heptyloxymethyl)-4-methoxy-5-methyltetrahydro-2H-pyran-3-ol, (2R,3R,4S,5S)-N-heptyl-3-hydroxy-4-methoxy-5-methyltetrahydro-2H-pyran-2-carboxamide (2S,3R,4S,5S)-2-[(Z)-(4-chlorophenyl)vinyl]-4-methoxy-5methyltetrahydro-2H-pyran-3-ol, (2S,3R,4S,5S)-2-(Benzyloxymethyl)-4-methoxy-5-methyltetrahydro-2H-pyran-3-ol, (2S,3R,4S,5S)-2-[(1E,3E)-4,8-dimethyl-1,3,7-nonatrienyl]-4-methoxy-5-methyltetrahydro-2H-pyran-3-ol, (2S,3R,4S,5S)-2-[(1Z,3E)-4,8-dimethyl-1,3,7-nonatrienyl]-4-methoxy-5-methyltetrahydro-2H-pyran-3-ol, (2S,3R,4S,5S)-4-methoxy-5-methyl-2-[(Z)-2-(4-propylphenyl)=vinyl]tetrahydro-2H-pyran-3-ol, (2S,3R,4S,5S)-4-methoxy-5-methyl-2-nonyltetrahydro-2H-pyran-3-ol, (6S,7S,10S)-10-methyl-7-[(E)-1-nonenyl-]-1,4,8-trioxaspiro[4,5]-decan-6-ol, (2S,3R,4S,5S)-4-methoxy-5-methyl-2-[(E)-1-nonenyl]tetrahydro-2H-pyran-3-amine, (2S,3R,4S,5S)-4-methoxy-5-methyl-2-[(Z)-1-nonenyl]tetrahydro-2H-pyran-3-amine, (2S,3R,4S,5S)-4-methoxy-5-methyl-2-nonyltetrahydro-2H-pyran-3-amine, (2S,3R,4S,5S)-4-ethoxy-5-methyl-2-[(Z)-1-nonenyl]tetrahydro-2H-pyran-3-amine, (2S,3R,4S,5S)-5-methyl-2-[(E)-1-nonenyl]-4-propoxytetrahydro-2H-pyran-3-amine, (2S,3R,4S,5S)-5-methyl-2-[(Z)-1-nonenyl]-4-propoxytetrahydro-2H-pyran-3-amine, (2S,3R,4S,5S)-5-methyl-2-nonyl-3-propoxytetrahydro-2H-pyran-3-amine, (2S,3R,4S,5S)-2-(heptyloxymethyl)-4-methoxy-5-methyltetrahydro-2H-pyran-3-amine, (2R,3R,4S,5S)-3-amino-N-heptyl-4-methoxy-5-methyltetrahydro-2H-pyran-2-carboxamide, (2S,3R,4R,5R)-5-butoxy-4-methoxy-2-[(E)-1-nonenyl]tetrahydro-2H-pyran-3-amine, (2S,3R,4R,5R)-5-benzyloxy-4-methoxy-2-[(E)-1-nonenyl]tetrahydro-2H-pyran-3-amine, (2S,3R,4S,5S)-4-methoxy-5-methyl-2-[(E)-2-naphthylvinyl]=tetrahydro-2H-pyran-3-amine, (2S,3R,4S,5S)-4-methoxy-5-methyl-2-(2-naphthylethyl)tetrahydro-2H-pyran-3-amine, (2S,3 R,4S,5S)-4-methoxy-5-methyl-2-[(E)-1-octenyl]tetrahydro-2H-pyran-3-amine, (2S,3R,4S,5S)-4-methoxy-5-methyl-2-[(E)-1-undecenyl]tetrahydro-2H-pyran-3-amine, (2S,3R,4S,5S)-2-[(E)-1-heptenyl]-4-methoxy-5-methyltetrahydro-2H-pyran-3-amine, (2S,3R,4R,5S)-4-methoxy-5-methyl -2-[(E)-1-nonenyl]tetrahydro-2H-pyran-3-amine, (2S,3R,4S,5R)-4-methoxy-5-methyl-2-nonyltetrahydro-2H-pyran-3-amine, (2S,3R,4S,5R)-4-methoxy-5-methyl-2-[(Z)-1-nonenyl]tetrahydro-2H-pyran-3-amine, (1S,2S,6S)-[2-methoxy-3,3-dimethyl-6-[(E)-1-nonenyl]cyclohexyl]=amine, (1S,2S,6S)-[2-methoxy-3,3-dimethyl-6-[(Z)-1-nonenyl]cyclohexyl]=amine, (1S,2S,6R)-[2-methoxy-3,3-dimethyl-6-nonyl cyclohexyl]amine, (1R,2S,6R)-[6-octyloxy-2-methoxy-3,3-dimethylcyclohexyl]amine;

(1R*,2R*)-(2-octyloxy-5,5-dimethylcyclohexyl)amine, (1R*,2S*)-[2-[(E)-1-nonenyl]-5,5-dimethylcyclohexyl] amine, and (1R*,2R*)-(5,5-dimethyl-2-nonylcyclohexyl)amine.

Examples of N-protecting groups for glycine are those well known in peptide chemistry such as tert-butoxycarbony, benzyloxycarbonyl, and phthalyl.

The acylation can be performed by treatment of a compound of formula (II) and N-protected-glycine with a dehydrating agent such as dicyclohexyl-carbodiimide, [1-cyclohexyl-3-(2-morpholinoethyl) carbodiimide metho-p-toluene-sulfonate, 1-ethyl-3-(3-dimethylaminopropyl) carbodiimide hydrochloride, or 2,4,6-triisopropylbenzenesulfonyl chloride, in the presence of a base catalyst such as 4-(dimethylamino)pyridine or 4-pyrrolidinopyridine.

This reaction proceeds in a solvent such as chloroform, dichloromethane, acetonitrile, dimethylformamide, pyridine, and the like, and at a temperature between 0° and 60° C., preferably between 0° and 25° C.

Examples of activated esters of N-protected glycine are an ester of N-hydroxysuccinimide, 1-hydroxybenzotriazole, N-hydroxyphthalimide or N-hydroxy-5-norbornene-2,3-dicarboxide.

The acylation can be performed by treatment of a compound (II) and an activated ester in the presence or absence of a base catalyst such as 4-(dimethylamino)pyridine or 4-pyrrolidinopyridine in the same solvent and reaction temperature as mentioned above.

The N-protecting group can be removed by the procedures known to those skilled in the art.

Process B:

In that process, the same the N-protecting radicals as those described in the above Process A can be used. Preferred is the t-butoxycarbonyl group.

The reaction can be carried out by treatment of a compound (II) and N-protected-(aminomethyl)phosphonic acid with the same dehydrating agent as described in the above Process A, or with an activating agent such as 2,4,6-triisopropylbenzenesulfonyl chloride and the like, in the presence of 4-dimethylaminopyridine or 4-pyrrolidinopyridine.

This reaction can be carried out in an organic solvent such as methylene chloride, chloroform, acetonitrile, dimethylformamide, pyridine and the like, and at a temperature between 0° and 60° C., preferably between 0° and 40° C. The N-protective group can then removed by the procedures known to those skilled in the art.

O-methylation of the resulting phosphonate can be carried out by reacting the resulting phosphonate with a methylating agent such as diazomethane, trimethylsilyldiazomethane, methyl iodide and the like. This reaction can be carried out in an organic solvent such as ether, tetrahydrofuran, dioxane, methanol or ethanol. A mixture of two or more solvents may also be used. The reaction using methyl iodide can be carried out in the presence of an acid acceptor such as alkali metal carbonate.

Process C:

In this process, the same N-protective group as defined in the above Process A can be used.

The N-alkylation can be carried out either with an alkylating agent or with a lower-alkylaldehyde under known conditions (i.e., Leuckart) or under catalytic hydrogenation conditions.

The reaction with an alkylating agent such as methyl iodide or ethyl iodide proceeds in the presence of an acid acceptor, such as alkali metal hydride, alkali metal carbonate or diisopropylethylamine in a solvent such as methylene dichloride, chloroform, tetrahydrofuran or the like. The reaction temperature is between –20° and 30° C., preferably between 0° and 25° C. A N-protecting group can be removed by the procedures known to those skilled in the art.

The reductive N-alkylation under Leuckart condition can be carried out by the procedure described in Org. Reaction Vol. V, Chapter 7, pp.301–330 (1949).

The reductive N-alkylation under catalytic hydrogenation conditions proceeds in a solvent such as methanol, ethanol or the like a room temperature.

Process D:

Specific examples of compounds of formula (IV) include:

(3S,4S,7S,8S)-8-methoxy-7-methyl-4-[(E)-1-nonenyl]-1,5-dioxaspiro[2,5]octane, (3S,4S,7S,8S)-8-methoxy-7-methyl-4-nonyl-1,5-dioxaspiro[2,5]=octane, (3S,4S,7S,8S)-8-methoxy-7-methyl-4-[(Z)-1-nonenyl]-1,5-dioxaspiro[2,5]octane, (3S,4S,7S,8S)-8-ethoxy-7-methyl -4-[(Z)-1-nonenyl]-1,5-dioxaspiro[2,5]octane, (3S,4S,7S,8S)-7-methyl-4-[(E)-1-nonenyl]-8-propoxy-1,5-dioxaspiro[2,5]octane, (3S,4S,7S,8S)-7-methyl-4-[(Z)-1-nonenyl]-8-propoxy-1,5-dioxaspiro[2,5]octane, (3S,4S,7S,8S)-7-methyl-4-nonyl-8-propoxy-1,5-dioxaspiro[2,5]=octane, (3S,4S,7R,8S)-7-butoxy-8-methoxy-4-[(E)-1-nonenyl]-1,5-dioxaspiro[2,5]octane, (3S,4S,7R,8S)-7-benzyloxy-8-methoxy-4-[(E)-1-nonenyl]-1,5-dioxaspiro[2,5]octane, (3S,4S,7S,8S)-8-methoxy-7-methyl-4-[(E)-2-naphthylvinyl]-1,5-dioxaspiro[2,5]octane, (3S,4S,7S,8S)-8-methoxy-7-methyl-4-(2-naphthylethyl)-1,5-dioxaspiro[2,5]octane, (3S,4S,7S,8S)-8-methoxy-7-methyl -4-[(E)-1-octenyl]-1,5-dioxaspiro[2,5]octane, (3S,4S,7S,8S)-8-methoxy-7-methyl-4-[(E)-1-undecenyl]-1,5-dioxaspiro[2,5]octane, (3S,4S,7S,8S)-4-[(E)-1-heptenyl]-8-methoxy-7-methyl-1,5-dioxaspiro[2,5]octane, (3S,4S,7S,8R)-8-methoxy-7-methyl -4-[(E)-1-nonenyl]-1,5-dioxaspiro[2,5]octane, (3S,4S,7R,8S)-8-methoxy-7-methyl-4-nonyl-1,5-dioxaspiro[2,5]=octane, (3S,4S,7R,5S)-8-methoxy-7-methyl-4-[(Z)-1-nonenyl]-1,5-dioxaspiro[2,5]octane, and (3S,4R,7S,8S)-8-methoxy-7-methyl-4-(heptylaminocarbonyl)-1,5-dioxaspiro[2,5]octane.

The above reaction can be performed in a solvent such as N,N-dimethyl formamide or dimethylsulfoxide at a temperature between –10° and 60° C., preferably between 0° and 25° C. The amount of the alkali metal salt of imidazole or 1H-1,2,4-triazole is usually 1 to 10 equivalents, preferably from 3 to 5 equivalents to the epoxide.

Process E:

Specific examples of the compound of formula (V) include:

(2S,5R)-[5,6-dihydro-5-methyl-2-nonyl-2H-pyran-3-yl] methanol, (2S,5R)-[5,6-dihydro-5-methyl-2-[(E)-1-nonenyl]-2H-pyran-3-yl]methanol, (2S,5R)-[5,6-dihydro-5-methyl-2-[(E)-2-naphthylvinyl]-2H-pyran-3-yl]methanol, (2S,5R)-[5,6-dihydro-5-methyl-2-(2-naphthylethyl)-2H-pyran-3-yl]methanol, (1R,2R,6S)-[2-methoxy-3,3-dimethyl-6-[(E)-1-nonenyl]cyclohexyl]=methanol, (1R,2R,6R)-[2-methoxy-3,3-dimethyl-6-nonylcyclohexyl]methanol, (1R,2R,6R)-[2-methoxy-3,3-dimethoxy-6-octyloxycyclohexyl]=methanol, (1R,2R,6S)-[2-methoxy-3,3-dimethyl-6-[(Z)-1-nonenyl]cyclohexyl]=methanol, (1R,2R,6S)-[2-methoxy-3,3-dimethyl-6-[(E)-2-naphthylvinyl]=cyclohexyl]methanol, (1R,2R,6R)-[2-methoxy-3,3-dimethyl-6-(2-naphthylethyl)=cyclohexyl]methanol, (1R*,6S*)-[3,3-dimethyl-6-[(E)-1-nonenyl]cyclohexyl]methanol, (1R*,6R*)-[3,3-dimethyl-6-nonylcyclohexyl]methanol, (1S*,6R*)-[3,3-dimethyl-6-octyloxycyclohexyl]methanol, (1R*,6S*)-[3,3-dimethyl-6-[(Z)-1-nonenyl]cyclohexyl]methanol, (1R*,6S*)-[3,3-dimethyl-6-[(E)-2-naphthylvinyl]cyclohexyl]=methanol, (1R*,6S*)-[3,3-dimethyl-6-(2-naphthylethyl)cyclohexyl]methanol, (1R,2R,6S)-[2-ethoxy-3,3-dimethyl-6-[(E)-1-nonenyl]cyclohexyl]=methanol, (1R,2R,6S)-[2-ethoxy-3,3-dimethyl-6-[(E)-2-naphthylvinyl]=cyclohexyl]methanol, (1R,2R,6R)-[3,3-dimethyl-6-nonyl-2-propoxycyclohexyl]methanol, (1R,2R,6R)-[3,3-dimethyl-6-(2-naphthylethyl)-2-propoxycyclo=hexyl]methanol (1R,2R,6R)-[2-methoxy-3,3-dimethyl-6-(naphthylmethoxy)=cyclohexyl]methanol, (1R,2R,6R)-[2-methoxy-3,3-dimethyl-6-(2-naphthylethoxy)=cyclohexyl]methanol, (1R,2R,6R)-[2-methoxy-3,3-dimethyl-6-(quinolylmethoxy)=cyclohexyl]methanol, (1R,2R,6R)-[2-methoxy-3,3-dimethyl-6-(2-quinolylethyloxy)=cyclohexyl]methanol, (1S*,6R*)-[3,3-dimethyl-6-(naphthylmethoxy)cyclohexyl]methanol, (1S*,6R*)-[3-3-dimethyl-6-(2-naphthylethoxy)cyclohexyl]methanol, (1S*,6R*)-[3,3-dimethyl-6-(quinolylmethoxy)cyclohexyl]methanol, and (1S*,6R*)-[3,3-dimethyl-6-(2-quinolylethoxy)cyclohexyl]methanol, Sulfonylation can be performed in a dry organic solvent such as methylene chloride, chloroform, ether, tetrahydrofuran in the presence of an acid acceptor such as triethylamine, pyridine or the like, and at a temperature between −10° and 40° C., preferably between 0° and 25° C.

The subsequent substitution reaction can be performed in a solvent such as N,N-dimethylformamide at a temperature between 0° and 60° C., preferably between 15° and 25° C. The amount of the alkali metal salt of imidazole or 1H-1,2,4-triazole is usually 1 to 10 equivalents, preferably from 3 to 5 equivalents to the sulfonate derivative.

Process F:

Specific examples of the compound represented by the formula (VI) include

[(1S*,2R*)-2-octyloxy-5,5-dimethylcyclohexyl]acetaldehyde,

[(1S,2R,6R)-6-octyloxy-2-methoxy-3,3-dimethylcyclohexyl]=acetaldehyde,

[(1S*,2R*)-5,5-dimethyl-2-nonylcyclohexyl]acetaldehyde,

[(1R,2R,6R)-1-methoxy-3,3-dimethyl-6-nonylcyclohexyl]=acetaldehyde,

[(1R,2R,6R)-2-ethoxy-3,3-dimethyl-6-nonylcyclohexyl]=acetaldehyde,

[(1S*,2R*)-5,5-dimethyl-2-(naphtylmethoxy)cyclohexyl]=acetaldehyde,

[(1S*,2R*)-5,5-dimethyl-2-(2-naphtylethoxy)cyclohexyl]=acetaldehyde,

[(1R,2R,6R)-2-methoxy-3,3-dimethyl-6-(naphtylmethoxy)=cyclohexyl]acetaldehyde, and [(1R,2R,6R)-2-methoxy-3,3-dimethyl-6-(2-naphtylethoxy)=cyclohexyl]acetaldehyde.

The conversion of the aldehyde group of compound (VI) into an O-trimethylsilyl-cyanohydrin can be carried out by treatment of the compound represented by the general formula (VI) with trimethylsilyl cyanide in the presence of catalytic amount of Lewis acid such as zinc chloride, zinc iodide, etc. preferably zinc iodide.

This reaction can be performed in a solvent such as benzene, toluene, xylene, etc., and at a temperature between 0° and 60° C., preferably between 0° and 25° C.

The reduction of the resulting cyanohydrin derivative to the corresponding b-amino alcohol derivative can be performed by use of alkali metal hydride reagents such as lithium aluminum hydride, etc.

This reaction proceeds in a solvent such as ether, tetrahydrofuran, etc., and at a temperature between 25° and 100° C., preferably between 50° and 80° C.

The manufacture of the pharmaceutically acceptable acid addition salts of the compound represented by formula (I) can be carried out by treatment of a free base of the compound represented by formula (I) with an acid in a per se conventional procedure for salt formation. Examples of therapeutically acceptable acids useful in the above process are inorganic acids (e.g. hydrochloric acid, hydrobromic acid, phosphoric acid, nitric acid, sulfuric acid) and organic acids (e.g. oxalic acid, acetic acid, formic acid, trifluoroacetic acid, maleic acid, succinic acid, fumaric acid, tartaric acid, citric acid, salicylic acid, sorbic acid, lactic acid).

Synthesis of starting material

The starting compounds of formulas II, IV, V and VI are novel compounds, and can be prepared in accordance with the following flow sheets 1, 2, 3, 4, 5 and 6:

a) Compounds of formula (II) in which X is an oxygen atom, $R^2$ is a hydrogen atom, $R^3$ is a hydroxy radical, and $R^1$, $R^4$, $R^5$, $R^6$ and $R^7$ are as defined above can be manufactured according to flow sheet 1 as follows:

flow sheet 1(1)

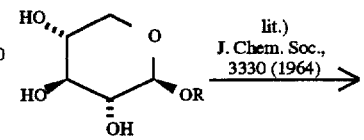

Alkyl D-xylopyranoside (1)

-continued
flow sheet 1(1)

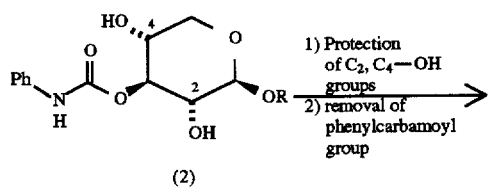
(2)

1) Protection of C$_2$, C$_4$—OH groups
2) removal of phenylcarbamoyl group

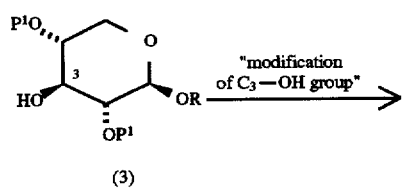
(3)

"modification of C$_3$—OH group"

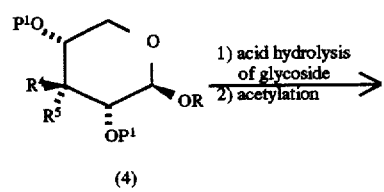
(4)

1) acid hydrolysis of glycoside
2) acetylation

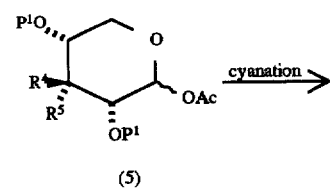
(5)

cyanation

-continued
flow sheet 1(1)

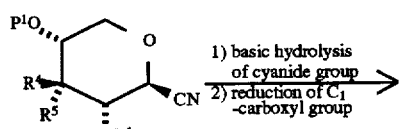
(6)

1) basic hydrolysis of cyanide group
2) reduction of C$_1$-carboxyl group

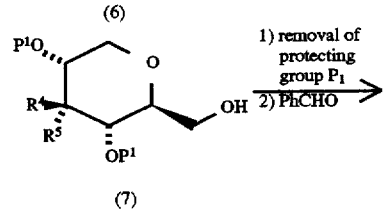
(7)

1) removal of protecting group P$_1$
2) PhCHO

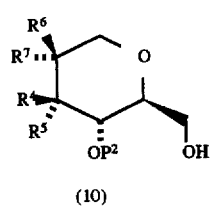
(8)

$\begin{pmatrix} R \text{ is lower-alkyl radical,} \\ P^1 \text{ is a hydroxy protecting radical} \end{pmatrix}$ flow sheet 1(2)

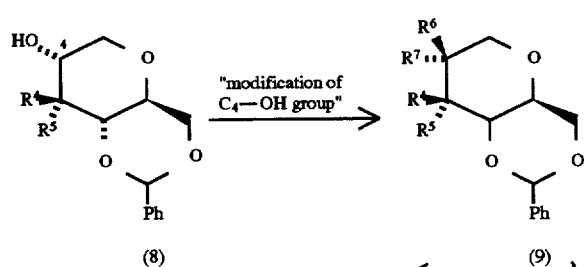

(8) → "modification of C$_4$—OH group" → (9)

1) removal of benzylidene
2) Protection of sec. —OH (i-Bu)$_2$AlH

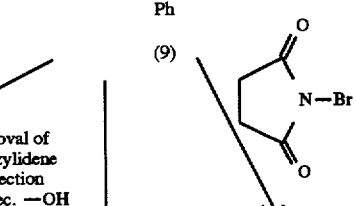
(10)                  (12)

-continued
flow sheet 1(2)

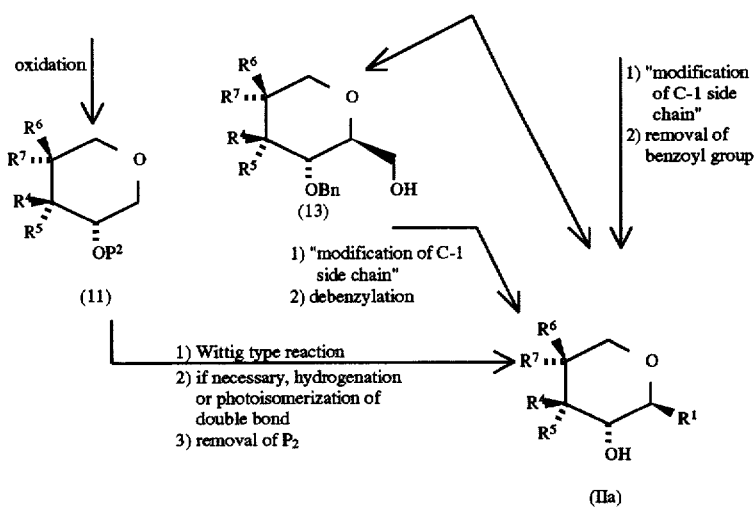

($P^2$ is a hydroxy protecting radical)

b) Compounds of formula (II) in which X is an oxygen atom, $R^2$ is a hydrogen atom, $R^3$ is an amino radical, and $R^4$, $R^5$, $R^6$ and $R^7$ are as defined above are novel compounds, and can be manufactured according to flow sheet 2 as follows:

flow sheet 2

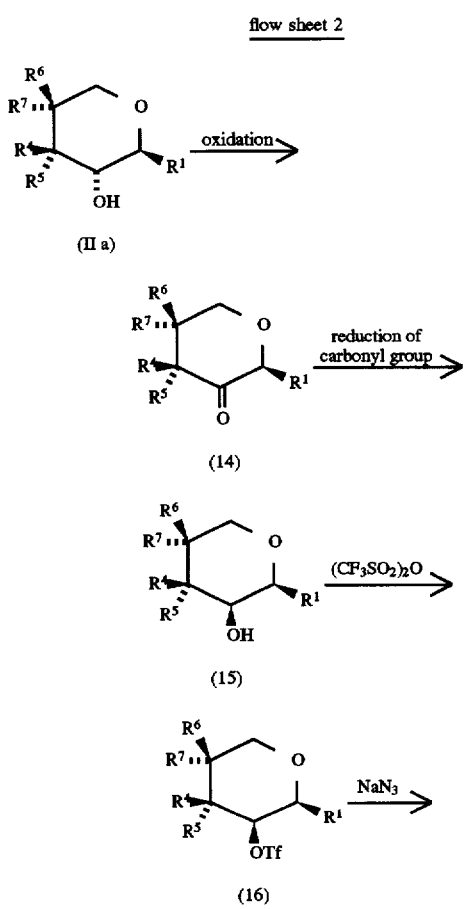

-continued
flow sheet 2

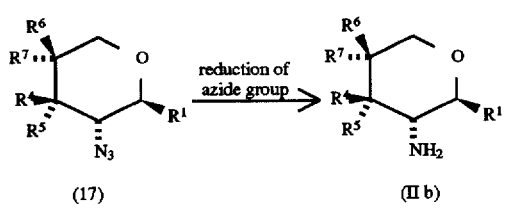

c) Compounds of formula (IV) in which X is an oxygen atom, and $R^1$, $R^4$, $R^5$, $R^6$ and $R^7$ are as defined above can be manufactured according to flow sheet 3 as follows:

flow sheet 3

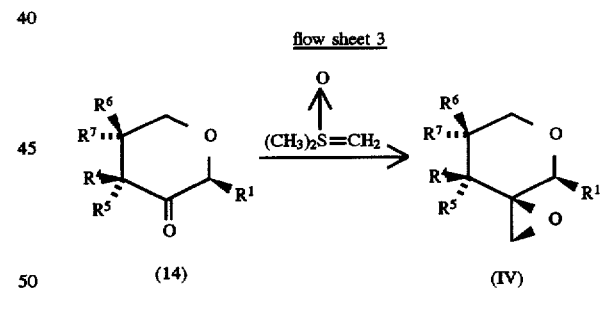

d) Compounds of formula (V) in which X is an oxygen atom, $R^2$ and $R^4$ forms a single bond, and $R^6$ and $R^7$ are as defined above can be manufactured according to the sheet 4 as follows:

flow sheet 4

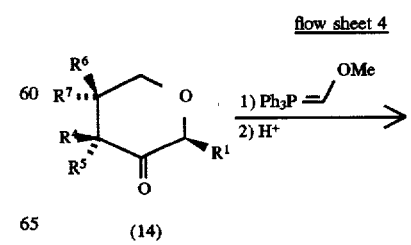

-continued
flow sheet 4
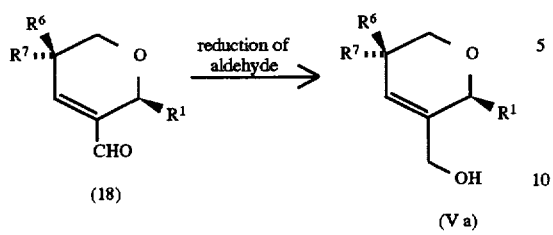
e) Compounds of formula (V) [in which X is methylene, $R^6$ is methyl, and $R^2$, $R^3$, $R^4$, $R^5$ and $R^7$ are as defined above can be manufactured according to flow sheet 5 as follows:
flow sheet 5(1)
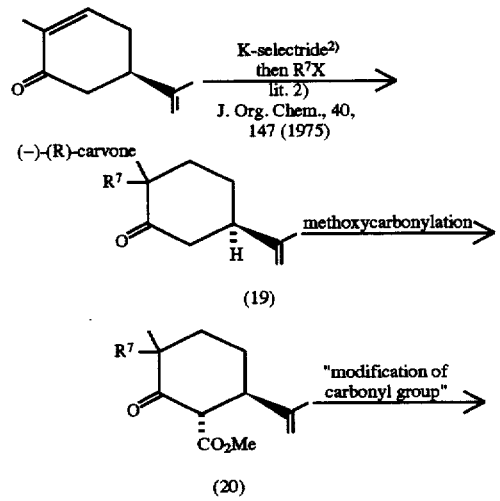
-continued
flow sheet 5(1)
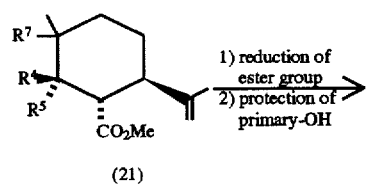
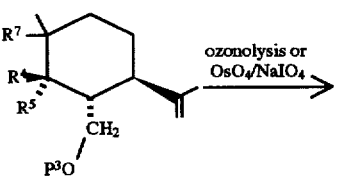
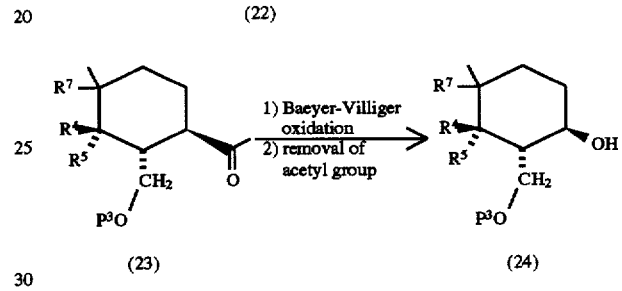
($P^3$ is a hydroxy protecting radical)
flow sheet 5(2)
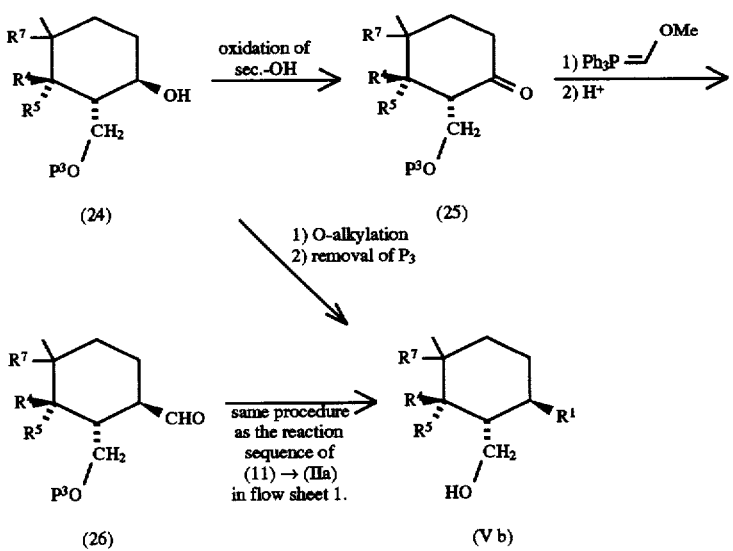
($P^3$ is a hydroxy protecting radical)

f) Compounds of formula (VI) [in which $R^1$, $R^4$, $R^5$ and $R^7$ are as defined above] can be manufactured according to flow sheet 6 as follows:

reductive removal of the resulting alcohol, or Wittig olefination or acetalization of the ketone, etc.

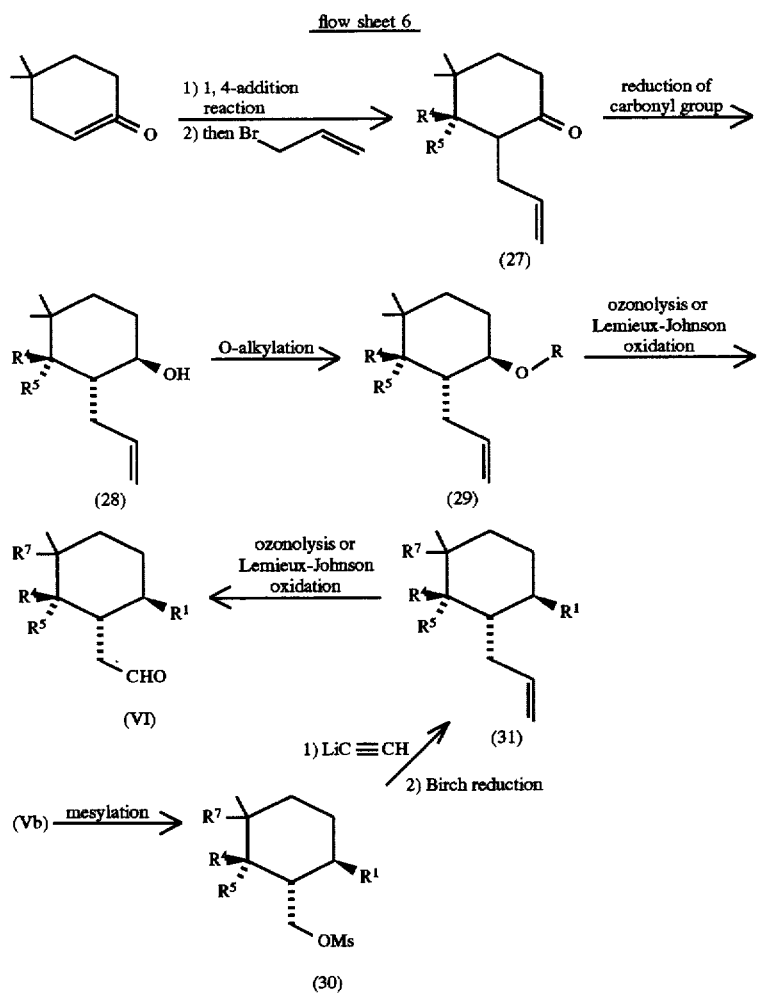

flow sheet 6

In flow sheet 1, the term "modification of $C_3$—OH" (reaction sequence (3) AE (4)) or "modification of $C_4$—OH" (reaction sequence (8) AE (9)) means, for example, O-alkylation, oxidation of sec-OH group, Wittig olefination or acetalization of corresponding oxo derivatives, reductive removal of corresponding thiocarbamate or acetate, or inversion of stereochemistry of sec-OH group by oxidation-reduction sequence etc.

The term "modification of C-1 side chain" (reaction sequence (12) AE (IIa)) means, for example, substitution reaction of bromide (12) with various nucleophiles such as alkali metal salt of an alkylthiol, aralkylthiol, etc. or conversion of bromide (12) into glycoside (IIa) by dehydrobromination, ozonolysis of the resulting enol ether followed by reduction of the lacton into a hemiacetal and then glycosidation.

The term "modification of C-1 side chain" (reaction (13) AE (IIa)) is, for example, O-alkylation or oxidation of the primary OH into a caxboxylic acid which is then converted into a corresponding ester derivative followed by aminolysis with an amine, etc.

In flow sheet 5, the term "modification of carbonyl group (reaction sequence (16) AE (17)) means, for example, reduction of the ketone to an alcohol followed by O-alkylation or The compounds provided according to the present invention exhibit broad antifungal activity against various fungi and can be used as agents for treatment and prophylaxis of fungal infectious diseases. The in vitro antifungal activities and acute toxicity of the compounds of the present invention are shown as follows:

1. In vitro antifungal activities

The in vitro antifungal activities of representative compounds of the present invention were measured by determining the minimal inhibitory concentration (MIC), which is the concentration of an antifungal at which no fungal growth can be observed.

The MICs were determined by the microbroth dilution procedure according to NCCLS with the following minor modifications (Galgiani et al., Antimicrob. Agents Chemother., 33, 731 (1989). The medium was solidified with 0.2% low melting point agarose and buffered to pH 7.0 with 0.25%: $K_2HPO_4$ in Yeast Nitrogen Base (Difco Lab.). Inoculum size was $1 \times 10^5$ cells/ml, and incubation was carried out for 3 days at 27° C. The MICs (mg/ml) are shown in Table 1. The reference compound is compound (IA) in U.S. Pat. No. 4,952,604. The compounds used are identified by reference to the Examples in which they were prepared.

The in vitro antifungal activities of the representative compounds of the present invention shown in Table 1 and Table 2 were measured by determining the minimal inhibitory concentrations (MIC: Method A) or 80% growth inhibition concentration (IC$_{80}$: Method B) respectively. MIC is defined as the concentration of an antifungal at which growth of fungi is not observed and IC$_{80}$ is the concentration where cell turbidity measured at OD$_{630}$ is reduced by 80%.

TABLE 1

Antifungal activity MIC (μg/ml)

| | Compound (Example No.) | | | | | | | | | | |
|---|---|---|---|---|---|---|---|---|---|---|---|
| | USP4952604 compound (IA) | 1 | 4 | 5 | 6 | 8 | 11 | 12 | 21 | 22 | 23 |
| *Candida albicans* | | | | | | | | | | | |
| CY1005 | >200 | 100 | 50 | 25 | 100 | 50 | 200 | >200 | 50 | 50 | 25 |
| CY3003 | >200 | 100 | 50 | 25 | 100 | 50 | 100 | >200 | 100 | 50 | 50 |
| CY1002 | >200 | 100 | 100 | 50 | 100 | 50 | 200 | 200 | 100 | 50 | 25 |
| *Cryptococcus neoformans* | | | | | | | | | | | |
| CY1057 | 3.13 | 1.56 | 3.13 | 12.5 | 12.5 | 12.5 | 6.25 | 1.56 | 12.5 | 6.25 | 12.5 |
| CY1061 | 12.5 | 6.25 | 12.5 | 25 | 25 | 12.5 | 25 | 6.25 | 25 | 12.5 | 12.5 |
| CY1059 | 3.13 | 3.13 | 6.25 | 12.5 | 12.5 | 12.5 | 6.25 | 3.13 | 12.5 | 12.5 | 12.5 |
| *Aspergillus fumigatus* | | | | | | | | | | | |
| CF1003 | 200 | 100 | 3.13 | 50 | 12.5 | 50 | 6.25 | 25 | 12.5 | 50 | 50 |
| CF1023 | 200 | 100 | 1.56 | 50 | 6.25 | 50 | 6.25 | 25 | 12.5 | 50 | 50 |
| CF1004 | 200 | 200 | 3.13 | 100 | 12.5 | 100 | 6.25 | 12.5 | 6.25 | 50 | 50 |

| | Compound (Example No.) | | | | | | | | | | |
|---|---|---|---|---|---|---|---|---|---|---|---|
| | 24 | 27 | 28 | 31 | 35 | 42 | 43 | 46 | 47 | 59 | 68 | 84 |
| *Candida albicans* | | | | | | | | | | | | |
| CY1005 | 100 | 100 | 50 | 50 | 25 | 50 | 25 | 25 | 100 | 25 | 12.5 | 12.5 |
| CY3003 | 50 | 50 | 50 | 25 | 50 | 50 | 25 | 25 | 100 | 25 | 12.5 | 12.5 |
| CY1002 | 50 | 100 | 50 | 50 | 25 | 100 | 50 | 50 | 100 | 50 | 25 | 12.5 |
| *Cryptococcus neoformans* | | | | | | | | | | | | |
| CY1057 | 25 | 6.25 | 3.13 | 6.25 | 3.13 | 3.13 | 6.25 | 25 | 12.5 | 3.13 | 0.39 | 3.13 |
| CY1061 | 50 | 12.5 | 12.5 | 12.5 | 12.5 | 12.5 | 12.5 | 50 | 25 | 3.13 | 3.13 | 6.25 |
| CY1059 | 25 | 12.5 | 3.13 | 12.5 | 6.25 | 3.13 | 6.25 | 50 | 12.5 | 6.25 | 0.78 | 6.25 |
| *Aspergillus fumigatus* | | | | | | | | | | | | |
| CF1003 | 50 | 50 | 50 | 100 | 25 | 100 | 50 | 25 | 25 | 3.13 | 6.25 | 25 |
| CF1023 | 50 | 50 | 25 | 50 | 25 | 50 | 25 | 25 | 25 | 12.5 | 6.25 | 6.25 |
| CF1004 | 25 | 100 | 50 | 200 | 25 | 100 | 50 | 25 | 25 | 12.5 | 12.25 | 6.25 |

TABLE 2

Antifungal activity IC$_{80}$ (μg/ml)

| | Compound (Example No.) | | | | | | | | | |
|---|---|---|---|---|---|---|---|---|---|---|
| | FCZ | 54 | 55 | 71 | 72 | 73 | 74 | 75 | 76 | 77 |
| *Candida albicans* | | | | | | | | | | |
| CY1005 | 1.2 | 12 | 69 | 0.094 | 0.094 | 0.011 | 0.093 | 0.2 | 0.77 | 0.18 |
| CY3003 | 1.0 | 18 | 50 | 0.036 | 0.06 | 0.02 | 0.038 | 0.34 | 0.36 | 0.093 |
| CY1002 | 1.1 | 18 | 49 | 0.03 | 0.095 | 0.008 | 0.076 | 0.18 | 0.38 | 0.16 |
| *C. neoformans* | | | | | | | | | | |
| CY1057 | 5.2 | 46 | 170 | 1.2 | 1.3 | 5.8 | 0.46 | 0.19 | 10 | 0.39 |
| CY1059 | 8.6 | 47 | 150 | 1.9 | 4.8 | 6.1 | 3.8 | 1.3 | 30 | 3.2 |
| *A. fumigatus* | | | | | | | | | | |
| CF1003 | 150 | 150 | >200 | 32 | 14 | 23 | 20 | >200 | 30 | >200 |
| CF1004 | 150 | 140 | >200 | 37 | 12 | 23 | 24 | >200 | 36 | >200 |

| | Compound (Example No.) | | | | | |
|---|---|---|---|---|---|---|
| | 78 | 79 | 80 | 81 | 82 | 83 |
| *Candida albicans* | | | | | | |
| CY1005 | 0.093 | 0.024 | 0.65 | 0.025 | 0.35 | 0.24 |

TABLE 2-continued

| | Antifungal activity IC$_{80}$ (µg/ml) | | | | | |
|---|---|---|---|---|---|---|
| CY3003 | 0.071 | 0.02 | 0.19 | 0.0042 | 0.17 | 0.59 |
| CY1002 | 0.03 | 0.023 | 0.35 | 0.0075 | 0.15 | 0.31 |
| *C. neoformans* | | | | | | |
| CY1057 | 8.4 | 0.86 | 11 | 1.5 | >200 | 0.21 |
| CY1059 | 21 | 4.7 | 12 | 1.5 | >200 | 0.19 |
| *A. fumigatus* | | | | | | |
| CF1003 | >200 | >200 | 93 | >200 | >200 | >200 |
| CF1004 | >200 | >200 | 40 | >200 | >200 | >200 |

IC$_{80}$ was measured by method B

Antifungal activities were determined by either method A or B (see below) using microtest plates according NCCLS with minor modifications (Galgiani et at., Antimicrob. Agents Chemother. 33, 731 (1989)).

(Method A) The medium was solidified with 0.2% low melting point agarose and buffered to pH 7.0 with 0.25% K$_2$HPO$_4$ in Yeast Nitrogen Base (Difco Lab.). Inoculum size was 1×10$^5$ cells/ml, and incubation was carried out for 3 days at 27° C. The MICs (mg/ml) are shown in Table 1. The reference compound is compound (IA) in U.S. Pat. No. 4,952,604.

(Method B) The medium for yeast was buffered to pH 7.0 with 0.25% K$_2$HPO$_4$ in Yeast Nitrogen Base (Difco Lab.). For the filamentous fungi, 0.2% of low melting point agar was supplemented to the above medium. Inoculum size was 1×10$^4$ cells/ml, and incubation was carried out for 1-2 days at 27° C. Fluconazole (Pfizer) was used as reference.

2. Acute toxicity

The acute toxicity (LD$_{50}$) of representative compounds (Examples 4, 21, 60 and 69) of the present invention was determined by oral administration in mice. The respective LD$_{50}$ values of the compounds obtained in Examples 4, 21, 60 and 69 as mentioned below are more than 500 mg/kg.

The compounds of the formula (I) and pharmaceutically acceptable salts thereof are very active antimycotic agents. They are active against a variety of fungal species including *Candida albicans*, *Cryptotoccus neoformans*, *Aspergillus fumigatus*, Trichophyton spp., Microsporum spp., Exophiala spp., *Blastomyces dermatitidis*, and *Histoplasma capsulatum*.

Thus, the compounds of the present invention are useful for topical and systemic treatment of mycoses in animals as well as in humans. For example, they are useful in treating topical and mucosal fungal infections caused by, among other species, Candida, Trichophyton, or Microsporum. They may also be used in the treatment of systemic fungal infections caused by, for example, Candida, Cryptococcus, Aspergillus, Paracoccidiodes, Sporotrix, Exophiala, Blastomyces, or Histoplasma.

For clinical use, the antifungals (I) or salt forms thereof can be administered alone, but will generally be administered in a pharmaceutical mixture formulated as appropriate to the particular use and purpose desired, by mixing excipient, binding agent, lubricant, disintegrating agent, coating material, emulsifier, suspending agent, solvent, stabilizer, absorption enhancer and/or ointment base. The mixture can be used for oral, injectable, rectal or topical administration.

Pharmaceutical formulations for oral administration may be granules, tablets, sugar coated tablets, capsules, pills, suspensions or emulsions. For parenteral injection intravenously, intramuscularly or subcutaneously, the formulations may be in the form of a sterile aqueous solution which may contain other substances, for example, salts or glucose to make the solution isotonic. The antifungal compounds of this invention can also be administered in the form of a suppository or pessary, or they can be applied topically in the form of a lotion, solution, cream, ointment or dusting powder.

The daily dosage level of the antifungal compounds of formula (I) can range from 0.1 to 50 mg/kg (in single or multiple divided doses) when administered by either the oral or parenteral route. Thus tablets or capsules contain from 5 mg to 0.5 g of active compound for administration singly or two or more at a time as appropriate. In any event the actual dosage can be determined by the physician and may be varied upon the age, weight and response of the particular patient.

In addition, the compounds of the formula (I) and their salts have activity against a variety of plant pathogenic fungi, including for example *Pyricularia oryzae*, *Pythium aphanidermatum*, Alternaria spp., and *Paecilomyces variotii*.

Thus, they can be applied for agricultural and horticultural purposes preferably in the form of a composition formulated as appropriate to the particular use and purpose desired, for example dusting powders, or granules, seed dressings, aqueous solutions, dispersions or emulsions, dips, sprays or aerosols. Such compositions may contain such conventional carriers, diluents or adjuvants as are known and acceptable in agriculture and horticulture. Other compounds having herbicidal or insecticidal activity, or additional antifungals can be incorporated in the compositions. The compounds and compositions can be applied in a number of ways, for example they can be applied directly to the plant foliage, stems, branches, seeds or roots or to the soil or other growing medium, and they may be used not only to eradicate disease, but also prophylactically to protect the plants or seeds from attack.

The following examples illustrate the preferred methods for the preparation of the compounds of the present invention, which are not intended to limit the scope of the invention thereto.

Preparation of Starting Materials

Reference Example 1

Preparation of (2R,3R,4S,5S)-3-tert-butyldimethylsilyloxy-methoxy-5-4-methyltetrahydro-2H-pyran-2-carbaldehyde (a) Preparation of methyl 2,4-di-O-benzyl-b-D-xylopyranoside To a solution of methyl 3-O-phenylcarbamoyl-b-D-xylopyranoside (73.6 g, 0.26 mole) in DMF (300 ml) was added by portions 60% NaH in oil (36.0 g, 0.9 mole). After stirring at room temperature for 30 min, benzyl bromide (113 ml, 0.95 mole) was added dropwise to the reaction mixture. After the addition was completed, the stirring was continued for 3 hr. The reaction mixture was evaporated under reduced pressure and the oily residue was partitioned between ether (500 ml) and water (500 ml). The ether layer was dried over anhydrous sodium sulfate, evaporated to dryness under reduced pressure. The resulting amber viscous oil (150 g) was dissolved in 28% NaOMe—MeOH, (750 ml) and heated under reflux for 19 hrs. The reaction mixture was evaporated to dryness under reduced pressure. The oily residue was partitioned between ether (500 ml) and water (500 ml). The ether layer was washed with water (250 ml×2), and evaporated to dryness under reduced pressure. The residue was chromatographed on silica gel using $CH_2Cl_2$/AcOEt (95:5) as an eluent to give methyl 2,4-di-O-benzyl-b-D-xylopyranoside (80.5 g, 90% yield) as amorphous powder; EI-MS: m/z 344 ($M^+$); $^1$H-NMR ($CDCl_3$)d: 2.54 (1H,d,J=2.5 Hz), 3.21 (1H,dd,J=7.5 & 9 Hz), 3.22 (1H,dd,J=10 & 12 Hz), 3.52 (3H,s), 3.49 (1H,m), 3.68 (1H,t,J=9 Hz), 3.93 (1H,dd,J=6 & 12 Hz), 4.25 (1H,d,J=7.5 Hz), 4.63 (1H,d,J=12 Hz), 4.66 (1H,d,J=11.5 Hz), 4.75 (1H,d,J=12 Hz), 4.90 (1H,d,J=12 Hz), 7.31 (10H,br.s).

(b) Preparation of methyl 2,4-di-O-benzyl-3-O-methyl-b-D-xyropyranoside

To a solution of methyl 2,4-di-O-benzyl-b-D-xytopyranoside (38 g, 0.11 mole) in dry DMF (500 ml) was added 60% NaH in oil (4.4 g, 0.11 mole). After stirring at 0° C. for 30 min, methyl iodide (17 g, 0.12 mole) was added and the reaction mixture was allowed to warm to room temperature. The solution was continued to stir for 1 hr and evaporated to dryness under reduced pressure. The oily residue was partitioned between ether (300 ml) and water (300 ml). The ether layer was dried over anhydrous sodium sulfate, evaporated to dryness under reduced pressure to give methyl 2,4-di-O-benzyl-3-O-methyl-b-D-xylopyranoside (39.4 g, 100% yield) as colorless oil; EI-MS: m/z 358 ($M^+$); 254 ($M^+$-Bn); $^1$H-NMR ($CDCl_3$)d: 3.18 (1H,dd,J=10 & 12 Hz), 3.24 (1H,dd,J=7.5 & 9 Hz), 3.29 (1H,t,J=9 Hz), 3.50 (1H,m), 3.52 (3H,s), 3.65 (3H,s), 3.9 (1H,dd,J=5.9 & 12 Hz), 4.21 (1H,d,J=7.5 Hz), 4.62 (1H,d,J=12 Hz), 4.69 (1H, d,J=11 Hz), 4.75 (1H,d,J=12 Hz), 4.85 (1H,d,11 Hz), 7.35 (10 br.s).

(c) Preparation of 2,4-di-O-benzyl-3-O-methyl-a,b-D-xylopyranosyl acetate

A suspension of methyl 2,4-di-O-benzyl-3-O-methyl-b-D-xylopyranside (30 g, 0.084 mole) in AcOH (250 ml) and 2N $H_2SO_4$ (100 ml) was heated at 100° C. for 3 hr. The clear solution was concentrated to half volume under reduced pressure, and partitioned between ether and water (400 ml each). The ether layer was washed successively with water (100 ml×2), 5% aqueous sodium bicarbonate (200 ml) and water (100 ml×2). The ether layer was dried over anhydrous sodium sulfate, evaporated to dryness under reduced pressure to give an anomeric mixture of the corresponding hemiacetal derivative (25 g) as a foam.

A solution of this hemiacetal derivative (25 g), triethyl amine (10 g, 0.1 mole) and catalytic amount of N,N-dimethyl-aminopyridine in dry methylene chloride (200 ml) was treated with acetyl chloride (7.1 g, 0.09 mole) at room temperature for 3 hr with stirring.

The solution was evaporated to dryness under reduced pressure, and partitioned between ether (200 ml) and water (200 ml). The ether layer was washed with water (50 ml×2), and evaporated to dryness under reduced pressure. The residue was chromatographed on silica gel using AcOEt/n-hexane (2:8) as an eluent to give 2,4-di-O-benzyl-3-O-methyl-a,b-D-xylopyranosyl acetate (22.8 g; 70% yield), an anomeric mixture as amorphous powder; EI-MS: m/z 386 ($M^+$), 343 ($M^+$-Ac), 295 ($M^+$-Bn); $^1$H-NMR ($CDCl_3$)d; 2.04 (1.5H,s); 2.13 (1.5H,s), 3.3–3.6 (4H,m), 3.66 (1.5H,s), 3.69 (1.5H,s), 3.70 (0.5H,dd,J=5 & 12 Hz), 3.90 (0.5H,dd,J=5 & 12 Hz), 4.61–4.80 (4H,m), 5.51 (0.5H,d,J=8.0 Hz), 6.15 (0.5H,d,J=3.9 Hz), 7.34 (10H,br.s).

(d) Preparation of 2,4-di-O-benzyl-3-O-methyl-a,b-D-xylopyranosyl cyanide

To a stirred solution of 2,4-di-O-benzyl-3-O-methyl-a,b-D-xylopyranosyl acetate (20 g, 0.052 mole) and $Me_3SiCN$ (20 ml, 0.16 mole) in anhydrous nitromethane (300 ml) was added boron trifluoride etherate (1.0 g, 0.007 mole) at room temperature. After the mixture was stirred at room temperature for 30 min, the mixture was evaporated to dryness under reduced pressure. The residue was chromatographed on silica gel using $CH_2C_{12}$/AcOEt (99:1) as an eluent to give 2,4-di-O-benzyl-3-O-methyl-a,b-D-xylopyranosyl cyanide as colorless oil (13.0 g, 71% yield); EI-MS: m/z 353 ($M^+$), 262 ($M^+$-Bn); $^1$H-NMR of b-cyano-isomer ($CDCl_3$)d; 3.15 (1H,dd,J=10, 11 Hz), 3.23 (1H,t,J=10 Hz), 3.49 (1H,m), 3.59 (1H,t,J=10 Hz), 3.66 (3H,s), 3.96 (1H,dd,J=5 & 11 Hz), 3.97 (1H,d,J=10 Hz), 4.61 (1H,d,J=12 Hz), 4.73 (1H,d,J=12 Hz), 4.84 (1H,d,J=11 Hz), 4.88 (1H,d,J=11 Hz), 7.29–7.42 (10H, m).

(e) Preparation of 2,4-di-O-benzyl-3-O-methyl-1,5-anhydro-L-glucitol

A solution of 2,4-di-O-benzyl-3-O-methyl-a,b-D-xylopyranosyl cyanide (13.0 g, 0.037 mole) in ethanol (100 ml) and aqueous 2.5N NaOH (50 ml) was stirred at room temperature for 2 days. The clear solution was concentrated to one-third of its original volume, adjusted to pH 4 with 1N HCl and partitioned between ether (300 ml) and water (100 ml). The ether layer was washed with water (1.00 ml×2), dried over magnesium sulfate and evaporated to dryness under reduced pressure.

To the resulting residue (8.9 g, 24 mmole) was added dropwise 2.0M solution of borane-methyl sulfide complex in THF (55.7 ml; 4.6 eq.) under nitrogen atmosphere at 0° C. (ice bath). After the addition was completed, the ice-bath was removed and the solution was stirred at room temperature for 21 hr and then at 40° C. for 4 hr. The reaction mixture was carefully poured into water (200 ml) and extracted with AcOEt (70 ml×3). The combined AcOEt layer was washed with brine and dried over anhydrous $MgSO_4$. $MgSO_4$ was filtered off and the solvent was removed under reduced pressure to obtain a crude product (ca. 10 g) as a colourless viscous oil. The crude product was then subjected to silica gel column chromatography. [$SiO_2$: ca. 250 g, eluent: n-hexane/AcOEt=2:1, then 1:1] to give 2,4-di-O-benzyl-3-O-methyl-1,5-anhydro-L-glucitol (5.42 g, 0.015 mole) as colorless needles and its C-5 epimer (1.04 g, 3 mmole) as a colorless viscous oil in 63.0% and 12.1% yield respectively; EI-MS: m/z 358 ($M^+$), 267 ($M^+$-Bn); $^1$H-NMR ($CDCl_3$)d: 1.82 (1H,br,s), 3.18 (1H,dd,J=11 Hz), 3.24 (1H, m), 3.37 (1H,m), 3.48 (1H,m), 3.63 (1H,m), 3.71 (3H,s), 3.80 (1H,br.d,J=12 Hz), 3.95 (1H,dd,J=6 & 11 Hz), 4.62 (1H,d,J=11 Hz), 4.65 (1H,d,J=11 Hz), 4.74 (1H,d,J=11 Hz), 4.87 (1H,d,J=11 Hz), 7.27–7.38 (10H,m).

(f) Preparation of 3-O-methyl-1,5-anhydro-L-glucitol

A solution of 2,4-di-O-benzyl-3-O-methyl-1,5-anhydro-L-glucitol (41.18 g, 115 mmole) in dry ether (80 ml) was added to a vigorously stirred solution of Na (15.8 g, 3.0 eq) in liquid ammonia under nitrogen atmosphere at −78° C.

After 4 hr at the liquid ammonia boiling point (−33° C.), the blue reaction mixture was carefully quenched by the slow addition of MeOH until the blue color disappeared. After evaporation of the liquid ammonia, water-MeOH (1:1) mixture (500 ml) was added and the resulting solution was neutralized by passing through Dowex 50W×8 (ca. 500 ml) column. The column was washed thoroughly with water-MeOH (1:1) mixture (500 ml) and the combined water-MeOH solution was evaporated under reduced pressure to give a crude product (38 g) as a brown oil. The brown oil was purified by silica gel column chromatography [SiO$_2$: ca. 1 kg] with CHCl$_3$/MeOH (4:1) as an eluent to give 3-O-methyl-1,5-anhydro-L-glucitol (16.09 g, 90.4 mmole) as a yellow viscous oil in 78.6% yield; FAB-MS: m/z 179 (MH$^+$); $^1$H-NMR, (CDCl$_3$)d: 1.95 (1H,t,J=6 Hz), 2.10 (1H, d,J=4 Hz), 2.45 (1H,d,J=4 Hz), 3.13 (1H,t,J=9 Hz), 3.28 (1H,t,J=10 Hz), 3.31 (1H,ddd,J=4, 5 & 9 Hz), 3.54 (1H,d, J=4 & 9 Hz), 3.69 (3H,s), 3.66–3.80 (2H,m), 3.90 (1H,m), 4.0 (1H,dd,J=5.5 & 10 Hz).

(g) Preparation of 4,6-O-benzylidene-3-O-methyl-1,5-anhydro-L-glucitol

To a stirred suspension of 3-O-methyl-1,5-anhydro-L-glucitol (0.1 g, 5.6×10$^{-4}$ mole) in benzaldehyde (2.0 ml) was added anhydrous zinc chloride (0.05 g, 3×10$^{-4}$ mole). The mixture was stirred at room temperature for 2 hrs. The mixture was evaporated to dryness under reduced pressure and partitioned between ethyl acetate (50 ml) and 10% sodium carbonate (50 ml). The ethyl acetate layer was washed with brine (20 ml×2), dried over anhydrous sodium sulfate and then evaporated to dryness to give a crude product (0.14 g) as the colorless oil. This oil was triturated with n-hexane (5.0 ml) to give 4,6-O-benzylidene-3-O-methyl- 1,5-anhydro-L-glucitol (0.127 g, 85%) as the colorless amorphous powder; EI-MS: m/z 266 (M$^+$); $^1$H-NMR (CDCl$_3$)d: 2.44 (1H,br.s), 3.33 (1H,dd,J=10 Hz), 3.34 (1H, t,J=11 Hz), 3.40 (1H,dt,J=5 & 10 Hz), 3.57 (1H,t,J=10 Hz), 3.68 (3H,s), 3.71 (1H,t,J=10 Hz), 3.71 (1H,m), 4.06 (1H, dd,J=5.7 & 11 Hz), 4.32 (1H,dd,J=5 & 10 Hz), 5.55 (1H,s), 7.36–7.39 (3H,m), 7.47–7.50 (2H,m).

(h) Preparation of 4,6-O-benzylidene-2-deoxy-3-O-methyl-2-oxo-1,5-anhydro-L-glucitol To a solution of oxalyl chloride (0.136 ml, 1.58 mmole) in dry CH$_2$Cl$_2$ (1.0 ml) was added-dropwise a solution of dry DMSO (0.197 ml, 2.78 mmole) in dry CH$_2$Cl$_2$ (1.0 ml) at −78° C. over 5 min. After stirring for 10 min at −78° C. a solution of 4,6-O-benzylidene-O-methyl-1,5-anhydro-L-glucitol (0.35 g, 1.32 mmole) in dry CH$_2$Cl$_2$ (1.0 ml) was added dropwise to the resulting milky suspension over 5 min at −78° C. After stirring for 15 min at −78° C, triethylamine (0.921 ml, 6.6 mmole) was added dropwise to the reaction mixture over 3 min, and stirring was continued for 30 min at −78° C. The reaction mixture was warmed up to room temperature gradually, and partitioned between CH$_2$Cl$_2$ (20 ml) and water (20 ml). The methylene chloride solution was washed with brine (10 ml×2), dried over anhydrous sodium sulfate and then evaporated to dryness. The residue was chromatographed on silica gel using CH$_2$Cl$_2$/AcOEt (9:1) as an eluent to give 4,6-O-benzylidene-2-deoxy-3-O-methyl-2-oxo-1,5-anhydro-L-glucitol (0.301 g, 86%) as colorless amorphous powder; EI-MS: m/z 264 (M$^+$); $^1$H-NMR-(DMSO)d: 3.45 (3H, s), 3.65 (1H,m), 3.70 (1H,t,J=10 Hz), 3.81 (1H,t,J=10 Hz), 3.90 (1H,dd,J=4 & 10 Hz), 4.01 (1H,d,J=14 Hz), 4.14 (1H,d,J=10 Hz), 4.18 (1H,d,J=14 Hz), 5.54 (1H,s), 7.35–7.41 (3H,m), 7.48–7.52 (2H,m).

(i) Preparation of 4,6-O-benzylidene-2-deoxy-3-O-methyl-2-methylene-1,5-anhydro-L-glucitol KH (17.2 g, 0.15 mol) in oil was placed in a three-necked flask (500 ml); the oil was removed with n-hexane (×3). To the dry KH 90 ml of THF (freshly distilled over LAH) was added, followed by 30 ml of hexamethyldisilazane (0.14 mol) with cooling (20° C.) and vigorous stirring. The resulting mixture was sonicated for 30 min, at which time the initial gray suspension became white. Then 53.6 g of methyltriphenylphosphonium bromide (0.15 mole, recrystallized from dichloromethane-ether) was added to the above mentioned base in one portion. The inner temperature rose to 35°–40° C. The resulting deep yellow suspension was stirred for 20 min. Then the reaction mixture was cooled to −40° C. A solution 4,6-O-benzylidene-2-deoxy 3-O-methyl-2-oxo-1,5-anhydro-L-glucitol (9.0 g, 0.034 mol) in THF-HMPA (9:1, 50 ml) was added dropwise to the cooled mixture over 10 min. The reaction mixture was allowed to warm to room temperature over 1 hr, and then partitioned between water and ether. The combined organic layer was dried over anhydrous magnesium sulfate, and evaporated to dryness to afford a crude exo-methylene derivative as an oil. This crude product was purified by flash chromatography (eluent: n-hexane-ethyl acetate=4:1) to give 4,6-O-benzylidene-2-deoxy-3-O-methyl-2-methylene-1,5-anhydro-L-glucitol (6.36 g, 71.2% yield) as colorless crystals; EI-MS: m/z 262 (M$^+$); $^1$H-NMR (CDCl$_3$)d: 3.53 (2H, m), 3.64 (3H,s), 3.70 (1H,dd,J=10 Hz), 3.95 (1H,m), 4.07 (1H,d,11 Hz), 4.29 (1H,d,11 Hz), 4.30 (1H,m), 5.10 (1H,s), 5.33 (1H,s), 5.56 (1H,s), 7.33–7.40 (3H,m), 7.49–7.52 (2H, m).

(j) Preparation of (2S,3R,4S,5S)-(3-hydroxy-4-methoxy-5-methyltetrahydro-2H-pyran-2-yl)methanol A solution of 4,6-O-benzylidene-2-deoxy-3-O-methyl-2-methylene-1,5-anhydro-L-glucitol (1.0 g, 3.8 mmole) in methanol (10 ml) was stirred under hydrogen atmosphere in the presence of Pd-black (10 mg) at room temperature for 12 hrs. The catalyst was removed by filtration and washed with methanol (10 ml×2). The combined filtrate and washings were evaporated to dryness under reduced pressure to give (2S,3R,4S,5S)-(3-hydroxy-4-methoxy-5-methyltetrahydro-2H-pyran-2-yl)methanol (0.668 g, 100%) as a colorless oil; EI-MS: m/z 176 (M$^+$), 145 (M$^+$—CH$_2$OH); $^1$H-NMR (CDCl$_3$)d: 1.00 (3H,d,7 Hz), 2.05 (1H,br.s), 2.21 (1H,m), 2.42 (1H,br.s), 3.24 (2H,m), 3.38 (3H,s), 3.60 (2H,m), 3.74 (1H,dd,J=6 & 12 Hz), 3.83 (1H,dd,J=2 & 12 Hz), 3.89 (1H,dd,J=3.5 & 12 Hz).

(k) Preparation of (2S,3R,4S,5S)-3-(tert-butyldimethyl=silyloxy)-2-[(tertbutyldimethylsilyloxy)methyl]-4-methoxy-5-methyltetrahydro-2H-pyran To a solution of (2S,3R,4S,5S)-(3-hydroxy-4-methoxy-5-methyltetrahydro-2H-pyran-2-yl)methanol (1 g, 5.68 mmole) and imidazole (1.93 g, 28.4 mmole) in dry DMF (5 ml) was added tert-butyldimethylchlorosilane (1.88 g, 12.5 mmole). After stirring at room temperature for 12 hr, the reaction mixture was evaporated to dryness under reduced pressure. The resulting viscous residue was partitioned between ether (25 ml) and water (20 ml). The ether layer was washed with water (20 ml×2), dried over anhydrous sodium sulfate and evaporated to dryness under reduced pressure. The residue was chromatographed on silica gel using AcOEt/n-hexane (1:100) as an eluent to give (2S,3R,4S,5S)-3-(tert-butyldimethylsilyloxy)-2-[(tert-butyldimethylsilyloxy)methyl]-4-methoxy-5-methyltetrahydro-2H-pyran as a colorless oil (1.84 g, 80% yield); EI-MS: m/z 404 (M$^+$); $^1$H-NMR (CDCl$_3$)d: 0.79 (9H,s), 0.80 (9H,s), 1.1 (3H,d,J=7 Hz), 2.20 (1H,m), 2.93 (1H,dd,J=3.5 & 9 Hz), 3.15 (1H,dd,J=4 & 11 Hz), 3.19 (1H,m), 3.45 (3H,s), 3.55 (2H,m), 3.65 (1H,dd,J=5.5 & 11 Hz), 3.75 (1H,dd,J=4.5 & 11 Hz).

(1) Preparation of (2S,3R,4S,5S)-[3-(tert-butyldimethyl=silyloxy)-4-methoxy-5-methyltetrahydro-2H-pyran-2-yl]methanol A mixture of trifluoroacetic acid (3.28 ml) and water (6.43 ml) was added to a vigorously, stirred solution of (2S,3R, 4S,5S)-3-(tert-butyldimethylsilyloxy)-2-[(tert-butyldimethylsilyloxy)methyl]-4-methoxy-5-methyltetrahydro-2H-pyran (1.0 g, 2.48 mmole) in dry THF (6.43 ml) at 5° C. After vigorous stirring for 25 min at 5° C., the reaction mixture was carefully quenched by the addition of cold saturated aqueous sodium bicarbonate (30 ml). The resulting emulsion was partitioned between ether (50 ml) and water (50 ml). The ether layer was washed with water (20 ml×2), dried over anhydrous sodium sulfate and evaporated to dryness under reduced pressure. The residue was chromatographed on silica gel using AcOEt:n-hexane (2:8) as an eluent to give (2S,3R,4S,5S)-[3-(tert-butyldimethylsilyloxy)-4-methoxy-5-methyltetrahydro-2H-pyran-2-yl]methanol (0.595 g, 83% yield) as a colorless oil; EI-MS: m/z 290 (M$^+$); $^1$H-NMR (CDCl$_3$)d: 0.87 (9H,s), 0.97 (3H,d,J=7 Hz), 1.92 (1H,br.s), 2.2 (1H,m), 3.14 (2H,m), 3.28 (3H,s), 3.56 (1H,t,J=9 Hz), 3.57 (1H,dd,J=3 & 11.5 Hz), 3.65 (1H,br.dd,J=6 & 11 Hz), 3.78 (1H,dd,J=2 & 11.5 Hz), 3.84 (1H,br.dd,J=2 & 11 Hz).

(m) Preparation of (2R,3R,4S,5S)-3-(tert-butyldimethyl=silyloxy)-4-methoxy-5-methyltetrahydro-2H-pyran-2-carbaldehyde To a solution of oxalyl chloride (0.036 ml, 0.42 mmole) in dry CH$_2$Cl$_2$ (0.5 ml) there was added dropwise a solution of dry DMSO (0.049 ml, 0.69 mmole) in dry CH$_2$Cl$_2$ (0.1 ml) at −78° C. over 5 min. After stirring for 10 min at −78° C., a solution of (2S,3R,4S,5S)-[3-(tert-butyldimethylsilyloxy)-4-methoxy-5-methyltetrahydro-2H-pyran-2-yl]methanol (0.1 g, 0.345 mmole) in dry CH$_2$Cl$_2$ (0.1 ml) was added dropwise to the resulting milky suspension over 5 min at −78° C. After stirring for 15 min at −78° C., triethylamine (0.24 ml, 1.73 mmole) was added dropwise to the reaction mixture over 3 min, and stirring was continued for 30 min at −78° C. The reaction mixture was then warmed up to room temperature gradually and partitioned between CH$_2$Cl$_2$ (10 ml) and water (10 ml). The methylene chloride layer was washed with brine (5 ml×2), dried over anhydrous sodium sulfate and evaporated to dryness under reduced pressure. The residue was chromatographed on silica gel using AcOEt/n-hexane (1:9) as an eluent to give (2R,3R,4S,5S)-3-(tert-butyldimethylsilyloxy)-4-methoxy-5-methyltetrahydro-2H-pyran-2-carbaldehyde (0.085 g, 86% yield) as a colorless oil; EI-MS: m/z 288 (M$^+$); $^1$H-NMR (CDCl3)d: 0.85 (3H,d,J=7 Hz), 0.87 (9H,s), 2.28 (1H,m), 3.12 (1H,dd,J=4 & 5 Hz), 3.28 (3H,s), 3.59 (1H, dd,J=5 & 11.5 Hz), 3.81 (1H,d,J=4. Hz), 3.81 (1H,dd,J=9 & 11.5 Hz), 4.08 (1H,dd,J=4 & 5 Hz), 9.80 (1H,s).

(Reference Example 2

Preparation of (2S,3R,4S,5S)-4-methoxy-5-methyl-2-[(Z)-nonenyl]=tetrahydro-2H-pyran-3-ol (a) To a stirred solution of n-octyltriphenylphosphonium bromide (2124 mg) in dry THF (10 ml) and dry HMPA (5 ml), there was added n-BuLi (4.0 ml, 1.6M in n-hexane) at 0° C. After the mixture was stirred at 0° C. for 30 min, a solution of (2S,3R,4S,5S)-4-methoxy-5-methyl-3-(tert-butyldimethylsilyloxy)tetrahydro-2H-pyran-2-carbaldehyde (497 mg) in dry THF (3 ml) was added to the resulting orange solution. The mixture was stirred at 0° C. for 30 min, and at room temperature for 2 hours. The reaction was quenched by addition of saturated aqueous ammonium chloride solution. The mixture was extracted with diethyl ether, and the combined ethereal extracts were washed with brine, dried over sodium sulfate, filtered, and concentrated. Purification of the residue by silica gel chromatography gave (2S,3R,4S,5S)-3-(tert-butyldimethylsilyloxy)-4-methoxy-5-methyl-2-[(Z)-1-nonenyl]tetrahydro-2H-pyran (602 mg, 72% yield).

(b) To a solution of tetra-n-butylammonium fluoride in THF (1.0M, 4.2 ml), there was added the above silylether (400 mg) in dry THF (5.5 ml). After stirring for 2 hrs at room temperature, the reaction was quenched with water. The mixture was extracted with diethyl ether, and the ethereal extract was washed with brine, dried over sodium sulfate, filtered, and concentrated. Purification of the residue by silica gel chromatography gave (2S,3R,4S,5S)-4-methoxy-5-methyl-2-[(Z)-1-nonenyl]tetrahydro-2H-pyran-3-ol (233 mg, 83% yield) as colorless oil; EI-MS: m/z 270 (M$^+$); $^1$H-NMR (CDCl$_3$)d: 0.98 (3H,d,J=7 Hz), 1.2–1.4 (12H,m), 2.0–2.3 (2H,m), 3.13 (1H,dd,J=6 & 9 Hz), 3.34 (3H,s), 3.43 (1H,t,J=9 Hz), 3.56 (1H,dd,J=2 & 12 Hz), 3.75 (1H,dd,J=2 & 12 Hz), 3.80 (1H,dt,J=1 & 9 Hz), 5.36 (1H,ddt,J=10, 11 & 2 Hz), 5.65 (1H,dt,J=11 & 7 Hz).

Reference Example 3

Preparation of (2S,3R,4S,5S)-4-methoxy-5-methyl-2-[(E)-1-noneyl]tetrahydro-2H-pyran-3-ol A solution of (2S,3R,4S,5S)-4-methoxy-5-methyl-2-[(Z)-1-nonenyl]tetrahydro-2H-pyran-3-ol (23 mg) and diphenyl disulfide (15 mg) in cyclohexane (1 ml) was irradiated with a medium-pressure mercury lamp for 1 hr at room temperature. Removal of the solvent gave a crude product, which was purified by preparative thin layer chromatography (developed 3 times with n-hexane: ethyl acetate=5:1) to afford (2S,3R,4S,5S)-4-methoxy-5-methyl-2-[(Z)-1-nonenyl]tetrahydro-2H-pyran-3-ol (20 mg, 87% yield) as a colorless oil; EI-MS: m/z 270 (M$^+$); $^1$H-NMR (CDCl$_3$)d: 0.83 (3H,t,J=7 Hz), 1.03 (3H,d,J=7 Hz), 1.2–1.5 (10H,m), 2.2 (1H,m), 2.3 (2H,m), 3.29 (1H,dd,J=5 & 9 Hz), 3.36 (3H,S), 3.4–3.5 (2H,m), 3.59 (1H,dd,J=2 & 12 Hz), 3.82 (1H,dd,J=1 & 12 Hz), 5.54 (1H,ddt,J=7, 16 & 2 Hz), 5.87 (1H,dt,J=16 & 7 Hz).

Reference Example 4

Preparation of (2S,3R,4S,5S)-4-methoxy-5-methyl-2-nonyltetra=hydro-2H-pyran-3-ol (2S,3R,4S,5S)-4-Methoxy-5-methyl-2-[(Z)-1-nonenyl]=tetrahydro-2H-pyran-3-ol (5.0 mg) was hydrogenated over 5% Pd/C (10 mg) in methanol (1 ml) for 1 hr. The mixture was filtered. The filter cake was washed with methanol. The combined filtrate was evaporated to give (2S,3R,4S,5S)-4-methoxy-5-methyl-2-nonyltetrahydro-2H-pyran-3-ol (4.8 mg, 96% yield) as a colorless oil; EI-MS: m/z 272 (M$^+$); $^1$H-NMR (CDCl$_3$)d: 0.87 (3H,t,J=7 Hz), 1.00 (3H,d,J=7 Hz), 1.2–1.5 (16H,m), 2.2 (1H,m), 3.09 (1H,m), 3.21 (1H,dd,J=5 & 10 Hz), 3.35 (3H, s), 3.39 (1H,t,J=10 Hz), 3.52 (1H,dd,J=2 & 12 Hz), 3.79 (1H,dd,J=2 & 12 Hz).

Reference Example 5

Preparation of (2S,3R,4S,5S)-2-(heptyloxymethyl-4-methoxy-5-methyltetrahydro-2H-pyran-3-ol (a) To a suspension of NaH (6 mg, 0.150 mM) in dry THF (0.5 ml) there was added (2S,3R,4S,5S)-(3-benzyloxy-4-methoxy-5-methyl=tetrahydro-2H-pyran-2-yl)methanol (30 mg, 0.11 mM) in dry THF (1 ml) at 0° C. After 20 min, n-heptyl bromide (22 ml, 0.14 mM) and potassium iodide (22 mg, 0.13 mM) was added to the mixture at 0° C. The reaction mixture was stirred at room temperature for 12 hrs and refluxed for 12 hrs. The reaction mixture was quenched with water and extracted with dichloromethane (2 times). The combined organic layer was washed with water, dried over $MgSO_4$ and concentrated. The residual oil was purified by silica gel chromatography (eluent; n-hexane:ethyl acetate=3:1) to give (2S,3R,4S,5S)-3-benzyloxy-2-(heptyloxymethyl)-4-methoxy-5-methyltetrahydro-2H-pyran (23 mg, 56%) as a colorless oil; EI-MS: m/z 364 ($M^+$).

(b) A mixture of above ether derivative (19 mg, 0.05 mmol) and Pd-black (5 mg) in ethyl acetate (0.8 ml) was stirred under hydrogen atmosphere over night. The catalyst was removed by filtration and washed with dichloromethane. The filtrate was dried over magnesium sulfate, filtered and concentrated. The residue was purified by silica gel chromatography using n-hexane:AcOEt (1:1) as an eluent to give (2S,3R,4S,5S)-2-(heptyloxymethyl)-4-methoxy-5-methyltetrahydro-2H-pyran-3-ol (10 mg, 71% yield) as colorless oil; CI-MS: m/z 275 ($MH^+$); $^1H$-NMR ($CDCl_3$)d: 0.87 (3H,t,J=7 Hz), 1.00 (3H,d,J=7 Hz), 1.27–1.33 (7H,m), 1.56–1.61 (3H,m), 2.19 (1H,m) 2.71 (1H,s), 3.24 (1H,dd,J=9 & 5 Hz), 3.32 (1H,ddd,J=10, 6 & 4 Hz), 3.39 (3H,s) 3.48 (1H,dt,J=7 & 3 Hz), 3.58 (1H,dd,J=12 & 2 Hz), 3.58 (1H,t,J=9 Hz); 3.62 (1H, dd,J=10 & 6 Hz), 3.68 (1H,dd,J=10 & 4 Hz), 3.82 (1H,dd,J=12 & 2 Hz).

Reference Example 6

Preparation of (2S,4S,5S)-4-methoxy-5-methyl-2-[(E)-1-nonenyl]=tetrahydro-2H-pyran-3-one To a mixture of N-chlorosuccinimide (78 mg) and dimethylsulfide (44 ml) in dry toluene (2 ml), there was added a solution of (2S,3R,4S,5S)-4-methoxy-5-methyl-2-[(E)-1-nonenyl]tetrahydro-2H-pyran-3-ol (53 mg) in dry toluene (0.3 ml) at −26° C., and the mixture was stirred at −26° C. for 1 hr. To the resulting mixture, triethylamine (0.1 ml) was added. After 15 min at −26° C., the mixture was allowed to warm to room temperature and continued to stir for an additional 1 hr. The reaction mixture was diluted with diethyl ether (2 ml), and water was added. The mixture was extracted with diethyl ether. The combined organic layers were washed with brine, dried over anhydrous sodium sulfate, filtered, and concentrated. Purification of the residue by flash column chromatography (n-hexane:ethyl acetate=10:1) gave (2S,4S,5S)-4-methoxy-5-methyl-2-[(E)-1-nonenyl]=tetrahydro-2H-pyran-3-one (41 mg, 78% yield) as colorless oil, EI-MS: m/z 267 ($M^+$-H); $^1H$-NMR ($CDCl_3$) d: 0.87 (3H,d,J=7 Hz), 1.02 (3H,d,J=7 Hz), 1.2–1.5 (10H, m), 2.09 (2H,m), 2.61 (1H,m), 3.44 (3H,s), 3.90 (1H,dd,J=3 & 12 Hz), 3.97 (1H,dd,J=2 & 12 Hz), 3.98 (1H,dd,J=1 & 7 Hz), 4.21 (1H,d,J=7 Hz) 5.64 (1H,ddt,J=7, 16 & 2 Hz), 5.79 (1H,dt,J=16 & 6 Hz).

Reference Example 7

Preparation of (2S,3R,4S,5S)-4-methoxy-5-methyl-2-[(E)-1-nonenyl]tetrahydro-2H-pyran-3-amine (a) The ketone (4.1 mg) in Reference Example 6 was dissolved in methanol (0.5 ml) and cooled to 0° C. Sodium borohydride (5.6 mg) was added to this solution. After stirring for 30 min at 0° C., the reaction was quenched by addition of water. The pH of the mixture was adjusted to pH 7 with 0.1N hydrochloric acid. The mixture was extracted with diethyl ether. The organic layer was washed with brine, dried over anhydrous sodium sulfate, filtered, and concentrated. Purification of the residue by silica gel chromatography (n-hexane:ethyl acetate=5:1) afforded (2S,3S,4S,5S)-4-methoxy-5-methyl-2-[(E)-1-nonenyl]=tetrahydro-2H-pyran-3-ol (37 mg, 89% yield).

(b) To a mixture of (2S,3S,4S,5S)-4-methoxy-5-methyl-2-[(E)-1-nonenyl]tetrahydro-2H-pyran-3-ol (30 mg) and 2,6-di-tert-butylpyridine (27 ml) in dry dichloromethane (0.5 ml), there was added trifluoromethane sulfonic anhydride (21 ml) at 0° C. The mixture was stirred for 20 min at 0° C., and then quenched with saturated aqueous sodium bicarbonate solution at 0° C. The resulting mixture was extracted with dichloromethane, and the combined organic extracts were washed with ice cooled saturated aqueous sodium bicarbonate solution and brine, dried over anhydrous sodium sulfate, filtered, and concentrated. Purification of the residue by flash column chromatography (n-hexane:ethyl acetate=10:1) gave (2S,3S,4S,5S)-4-methoxy-5-methyl-2-[(E)-1-nonenyl]=tetrahydro-2H-pyran-3-yl trifluoromethane sulfonate (29 mg, 64% yield) which was immediately used for the following reaction.

(c) The above sulfonate (29 mg) was dissolved in N,N-dimethyl formamide (0.9 ml) and cooled to 0° C. Lithium azide (36 mg) was added to this solution. After stirring for 15 min at 0° C., the reaction mixture was diluted with water (2 ml). The mixture was extracted with ether. The combined ethereal layer was washed with brine, dried over anhydrous sodium sulfate, filtered and concentrated. Purification of the residue by preparative thin layer chromatography (n-hexane:ethyl acetate=10:1) gave (2S,3R,4S,5S)-3-azido-4-methoxy-5-methyl-2-[(E)-1-nonenyl]tetrahydro-2H-pyran (9 mg, 43% yield).

(d) A mixture of the above azide (9 mg) and lithium aluminum hydride (2 mg) in dry ether (1.5 ml) was refluxed for 1 hr. After the mixture was allowed to cool to 0° C., the mixture was treated by successive dropwise addition of 2 ml of water, 2 ml of 15% sodium hydroxide solution, and 6 ml of water. The resulting granular white precipitate was filtered, and the filtrate was concentrated to give a crude product. Purifica-tion of the crude product by preparative thin layer chromatography (ethyl acetate as an eluent) gave (2S,3R,4S,5S)-4-methoxy-5-methyl-2-[(E)-1-nonenyl] tetrahydro-2H-pyran-3-amine (6.8 mg, 83% yield) as a colorless oil; EI-MS: m/z 269 ($M^+$); $^1H$-NMR ($CDCl_3$)d: 0.88 (3H,t,J=7 Hz), 1.03 (3H,d,J=8 Hz), 1.2–1.4 (10H,m), 2.04 (2H,m), 2.16 (1H,m), 3.19 (1H, dd,J=5 & 10 Hz), 3.36 (3H,s), 3.46 (1H,t,J=10 Hz), 3.61 (1H,dd,J=4 & 12 Hz), 3.82 (1H,dd,J=4 & 12 Hz), 5.42 (1H,dd,J=8 & 16 Hz), 5.82 (1H,dt,J=16 & 6 Hz).

Reference Example 8

Preparation of (2S,3R,4S,5S)-5-methyl-4-methoxy-2-(1-nonynyl)=tetrahydro-2H-pyran-3-ol (a) To a solution of triphenylphosphine (136 mg) and carbon tetrabromide (172 mg) in dry dichloromethane (2 ml),there was added a solution of (2S,3R,4S,5S)-4-methoxy-5-methyl-3-(tert-butyl=dimethylsilyloxy) tetrahydro-2H-pyran-2-carbaldehyde (50 mg) in dry dichloromethane (0.5 ml) at room temperature. After stirring for 1 hr at room temperature the mixture was filtered and the filtrate was evaporated. Purification of the residue with silica gel column chromatography gave (2S,3R,4S,5S)-2-(2,2-dibromovinyl)-3-(tert-butyldimethylsilyloxy)-4-methoxy-5-methyltetrahydro-2H-pyran (70 mg, 91% yield).

(b) A solution of the above dibromide (70 mg) in dry tetrahydrofuran at −78° C. was treated with n-butyl lithium (0.19 ml of 1.65M solution in n-hexane). After being stirred for 1 hr at −78° C., the reaction mixture was warmed to room temperature and continued to stir for 1 hr. The reaction was quenched by addition of aqueous saturated ammonium chloride solution. The mixture was extracted with ether. The combined ethereal extracts were washed with brine, dried over anhydrous sodium sulfate, and concentrated. The residue was purified by silica gel chromatography (using n-hexane:ethyl acetate=20:1 as an eluent) to give (2S,3R, 4S,5S)-3-(tert-butyldimethylsilyloxy)-2-ethynyl-4-methoxy-5-methyl-tetrahydro-2H-pyran (23 mg, 51% yield) as colorless oil EI-MS: m/z 284 (M$^+$). $^1$H-NMR (CDCl$_3$)d: 0.10 (3H, s), 0.12 (3H,s), 0.89 (9H,s), 0.99 (3H,d,J=7 Hz), 2.20 (1H,m), 2.42 (1H,d,J=2 Hz), 3.07 (1H, dd,J=5 & 8 Hz), 3.31 (3H,s), 3.50 (1H,dd,J=3 & 12 Hz), 3.67 (1H,t,J=8 Hz), 3.79 (1H,dd,J=3 & 12 Hz), 3.86 (1H,dd,J=2 & 8 Hz).

(c) A solution of the above acetylene derivative (23 mg) in dry tetrahydrofuran at −78° C. was treated with n-butyl lithium (59 ml of 1.65M solution in n-hexane). After being stirred for 30 min at −78° C., n-heptylbromide (38 ml) was added. The mixture was warmed to room temperature and stirred for an additional 1 hr. The reaction was quenched by addition of aqueous saturated ammonium chloride solution. The mixture was extracted with ether. The combined ethereal extracts were washed with brine, dried over anhydrous sodium sulfate, filtered, and concentrated. Purification of the residue by thin layer chromatography gave (2S,3R,4S,5S)-3-(tert-butyldimethylsilyloxy)-4-methoxy-5-methyl-2-(1-nonynyl)tetrahydro-2H-pyran (10 mg, 32% yield). (2S,3R, 4S, 5S)-5-methyl-4-methoxy-2-(1-nonynyl)tetrahydro-2H-pyran-3-ol was obtained as colorless oil from the above compound according to a manner analogous to that of Reference Example 2-b; EI-MS: m/z 268 (M$^+$); $^1$H-NMR (CDCl$_3$)d: 0.87 (3H,t,J=7 Hz), 1.04 (3H,d, J=8 Hz), 1.2–1.4 (10H,m), 2.2 (3H,m), 3.21 (1H, dd,J=5 & 9 Hz), 3.40 (3H,s), 3.55 (1H,dd,J=3 & 12 Hz), 3.62 (1H,t,J=9 Hz), 3.82 (2H,m).

Reference Example 9

Preparation of (2S,3R,4S,5S)-N-heptyl-3-hydroxy-4-methoxy-5-methyl tetrahydro-2H-pyran-2-carboxamide (a) Sodium periodate (0.05 g, 0.234 mmole) and ruthenium oxide (0.02 g, 0.15 mmole) were added to a vigorously stirred emulsion of (2S,3R,4S,5S)-(3-benzyloxy-4-methoxy-5-methyltetrahydro-2H-pyran-2-yl)methanol (0.02 g, 0.075 mmole) in a mixed solvent of acetonitrile (2 ml), carbon tetrachloride (2 ml) and water (3 ml). After stirring for 12 hr, the reaction mixture was adjusted to pH 2 with 0.1N aqueous HCl and partitioned between ether (20 ml) and water (10 ml). The ether layer was dried over anhydrous magnesium sulfate and evaporated to dryness under reduced pressure. To a solution of the resulting crude acid in a mixed solvent of ether (5 ml) and MeOH (1 ml) there was added a 10% solution of trimethylsilyldiazomethane in n-hexane (0.5 g, 0.44 mmole). The mixture was stirred at room temperature for 10 min. The solution was evaporated to dryness under reduced pressure. The residue was chromatographed on silica gel using AcOEt/n-hexane (2:8) as an eluent to give methyl (2R,3R,4S,5S)-3-benzyloxy-4-methoxy-5-methyltetrahydro-2H-pyran-2-carboxylate (6.6 mg, 30% yield) as an oil; EI-MS m/z 294 (M$^+$); $^1$H-NMR (CDCl$_3$)d: 1.0 (3H,d,J=7.2 Hz), 2.2 (1H,m), 3.20 (1H,dd,J=5 & 11 Hz), 3.35 (1H,dd,J=4 & 9 Hz), 3.6 (1H,t,J=9 Hz), 3.65 (3H, s), 3.7 (3H,s), 3.8 (1H,d,J=9 Hz), 4.0 (1H, dd,J=4 & 11 Hz), 4.59 (1H,d,J=12 Hz), 4.62 (1H,d,J=12 Hz), 7.3 (5H,m).

(b) A mixture of methyl (2R,3R,4S,5S)-3-benzyloxy-4-methoxy-5-methyltetrahydro-2H-pyran-2-carboxylate (7 mg, 0.024 mmole) and heptylamine (0.1 ml, 0.68 mmole) was heated at 90° C. for 3 hr. The reaction mixture was adjusted to pH 3 with 0.1N aqueous HCl, and partitioned between ether (10 ml) and water (10 ml). The ether layer was dried over anhydrous magnesium sulfate and evaporated to dryness under reduced pressure. A solution of the resulting crude amide in MeOH (5 ml) was stirred under hydrogen atmosphere in the presence of Pd-black (5 mg) at room temperature for 12 hr. The catalyst was removed by filtration and washed with methanol (2 ml×2). The combined filtrate and washings were evaporated to dryness under reduced pressure. The residue was chromatographed on silica gel using AcOEt/n-hexane (4:6) as an eluent to give (2R,3R,4S, 5S)-N-heptyl-3-hydroxy-4-methoxy-5methyltetrahydro-2H-pyran-2-carboxamide (3.4 mg, 50% yield) as an oil; FAB-MS: m/z 288 (MH$^+$). $^1$H-NMR (CDCl$_3$)d: 0.91 (3H,t, J=6.5 Hz), 1.05 (3H,d,J=7 Hz), 1.25 (10H,br.s), 2.2 (1H, m), 3.10–3.6 (7H,br.m), 3.3 (3H,s), 3.81 (1H,dd,J=2.5 & 12 Hz), 8.0 (1H,br.s).

Reference Example 10

Preparation of (3S,4S,7S,8S)-8-methoxy-7-methyl-4-[(E)-1-nonenyl]-1,5-dioxaspiro[2,5]octane Trimethylsulfoxonium iodide (74 mg) was added to a suspension of sodium hydride (14 mg, 60% oil suspension) in dry dimethylsulfamide (1 ml). The mixture was stirred for 1 hr at room temperature. A solution of (2S,4S,5S)-4-methoxy-5-methyl-2-[(E)-1-nonenyl]tetrahydro-2H-pyran-3-one (30 mg) in dry tetrahydrofuran (0.2 ml) was added dropwise. After stirring for 2 hrs at room temperature, the reaction was quenched by addition of saturated aqueous ammonium chloride solution. The mixture was extracted with diethyl ether, and the combined organic extracts were washed with brine, dried over anhydrous sodium sulfate, filtered, and concentrated. Purification of the residue by preparative thin layer chromatography (n-hexane:ethyl acetate=10:1) gave (3S,4S,7S,8S)-8-methoxy-7-methyl-4-[(E)-1-nonenyl]-1,5-dioxaspiro[2,5]octane (23 mg, 72% yield) as colorless oil; EI-MS: m/z 282 (M$^+$); $^1$H-NMR (CDCl$_3$)d: 0.87 (3H,t,J=7 Hz), 1.10 (1H,d,J=7 Hz), 1.2–1.4 (10H,m), 2.0 (2H,m), 2.2 (1H,m), 2.43 (1H,d,J=5 Hz), 2.80 (1H,d,J=5 Hz), 3.37 (3H,s), 3.52 (1H,d,J=3 Hz), 3.66 (1H, dd,J=3 & 12 Hz), 3.90 (1H,dd,J=4 & 12 Hz), 3.94 (1H,d,J=8 Hz), 5.56 (1H,dd,J=8 & 15 Hz), 5.71 (1H,m).

Reference Example 11

Preparation of (2S,5R)-(5,6-dihydro-5-methyl-2-nonyl-2H-pyran-3-yl)methanol (a) (2S,4S,5S)-4-methoxy-5-methyl-2-nonyltetrahydro-2H-pyran-3-one was obtained from (2S,3R,4S,5S)-4-methoxy-5-methyl-2-nonyltetrahydro-2H-pyran-3-ol according to a manner analogous to that of Reference Example 6.

(b) To a stirred suspension of methoxymethylphosphonium chloride (1,130 mg) in dry tetrahydrofuran (3 ml) there was added n-BuLi (1.9 ml, 1.6M in n-hexane) at 0° C. After the mixture was stirred at 0° C. for 30 min, a solution of (2S,4S,5S)-4-methoxy-5-methyl-2-nonyltetrahydro-2H-pyran-3-one (273 mg) in dry tetrahydrofuran (3 ml) was added to the resulting deep orange solution. After 30 min, the mixture was allowed to warm to room temperature, and stirred for an additional 2 hrs. The reaction was quenched by addition of saturated aqueous ammonium chloride solution. The mixture was extracted with diethyl ether, and the combined organic extracts were washed with brine, dried over anhydrous sodium sulfate, filtered and concentrated. Purification of the residue by silica gel chromatography (n-hexane: ethyl acetate=10:1 as an eluent) gave (2S,4S,5S)-4-methoxy-5-methyl-3-methoxymethylene-2-nonyltetrahydro-2H-pyran (249 mg, 83% yield).

(e) A solution of the above enol ether (249 mg) and p-toluene sulfonic acid (5.3 mg) in dichloromethane (5 ml) was stirred for 1 hr. The reaction mixture was partitioned between saturated aqueous sodium bicarbonate solution and dichloromethane. The organic layer was washed with brine, dried over anhydrous sodium sulfate, filtered, and concentrated. Purification of the residue by silica gel chromatography gave (2S,5R)-5,6-dihydro-5-methyl-2-nonyl-2H-pyran-3-carbaldehyde (141 mg, 67% yield).

(d) To a solution of (2S,5R)-5,6-dihydro-5-methyl-2-nonyl-2H-pyran-2-carbaldehyde (141 mg) in methanol (1 ml), there was added sodium borohydride (21 mg) at room temperature. The mixture was stirred for 30 min, and the reaction was quenched by addition of water. The pH of the mixture was adjusted to pH 7 with 0.1N hydrochloric acid. The mixture was extracted with diethyl ether. The combined organic layers were washed with brine, dried over anhydrous sodium sulfate, filtered, and concentrated. Purification of the residue with preparative thin layer chromatography (using n-hexane:ethyl acetate=5:1 as an eluent) gave (2S,5R)-(5,6-dihydro-5-methyl-2-nonyl-2H-pyran-3-yl)=methanol (142 mg, 100% yield) as colorless oil; EI-MS: m/z 254 (M$^+$); $^1$H-NMR (CDCl$_3$)d: 0.81 (3H,t,J=7 Hz), 0.94 (3H,d,J=8 Hz), 1.20 (14H,br.s), 1.36 (2H,m), 1.48 (1H,m), 3.39 (1H, dd,J=5 & 11 Hz), 3.61 (1H,dd,J=5 & 11 Hz), 3.93 (1H,d, J=12 Hz), 4.01 (1H,d,J=12 Hz), 4.09 (1H,d,J=7 Hz), 5.69 (1H,d,J=3 Hz).

Reference Example 12

Preparation of (1R,2S,3R)-2-benzyloxymethyl-3-methoxy-4,4-dimethylcyclohexanol (a) Preparation of methyl (1S,6R)-3,3-dimethyl-6-(1-methylvinyl)-2-oxocyclohexane-1-carboxylate To a stirred mixture of sodium hydride (162 mg) and dimethyl carbonate (850 ml) in dry pyridine (1 ml) at 80°–85° C. (bath temperature) under Ar atmosphere, a solution of 1-methyl-1,6-dihydrocarvone (335 mg) in dry pyridine (1.5 ml) was added dropwise. After the mixture was stirred for 3 hrs at 80°–85° C., the mixture was cooled with an ice-bath. The reaction mixture was neutralized with acetic acid and diluted with water. The mixture was extracted with ether. The combined organic extracts were washed with saturated sodium-bicarbonate solution and brine, dried over anhydrous sodium sulfate, filtered, and concentrated. Purification of the residue by silica gel column chromatography (using n-hexane:ethyl acetate=20:1 as an eluent) gave methyl (1S,6R)-3,3-dimethyl-6-(1-methylvinyl)-2-oxocyclohexane-1-carboxylate (361 mg, 80% yield).

b) Preparation of methyl (1S,2R,6R)-2-methoxy-3,3-dimethyl-6-(1-methylvinyl)cyclohexane-1-carboxylate To a mixture of methyl (1S,6R)-3,3-dimethyl-6-(1-methylvinyl)-2-oxocyclohexane-1-carboxylate (1.38 g) and cerium (II) chloride heptahydrate (2.14 g) in methanol (10 ml) was added sodium borohydride (217 mg) at 0° C. The mixture was stirred at room temperature for 1 hr, and the reaction was quenched by addition of water. The pH of the mixture was adjusted to pH 7 with 0.1N hydrochloric acid. The mixture was extracted with ether. The combined organic extracts were washed with brine, dried over anhydrous sodium sulfate, filtered, and concentrated. Purification of the residue by flash column chromatography (using n-hexane:ethyl acetate=20:1 as an eluent) gave methyl (1S, 2R,6R)-2-hydroxy-3,3-dimethyl-6-(1-methylvinyl) cyclohexane-1-carboxylate (1.15 g, 83% yield).

A mixture of the above alcohol (1.15 g) and sodium hydride (230 mg, 60% dispersion in oil) and methyl iodide (0.6 ml) in dry N,N-dimethylformamide was stirred for 3 hrs at room temperature. The mixture was cooled to 0° C., and reaction was quenched by addition of water. The pH of the mixture was adjusted to pH 7 with 0.1N hydrochloric acid. The mixture was extracted with diethyl ether, and the combined organic layers were washed with brine, dried over sodium sulfate, filtered and concentrated to give methyl (1S,2R,6R)-2-methoxy-3,3-dimethyl-6-(1-methylvinyl)-cyclohexane-1-carboxylate (1.12 g, 92% yield).

c) Preparation of benzyl [(1R,2R,6R)-2-methoxy-3,3-dimethyl-6-(1-methylvinyl)cyclohexyl]methyl ether To a solution of methyl (1S,2R,6R)-2-methoxy-3,3-dimethyl-6-(1-methylvinyl)cylcohexane-1-carboxylate (1.03 g) in dry diethyl ether (10 ml) at 0° C., lithium aluminum hydride (92 mg) was added in small portions. The mixture was stirred for 1 hr at room temperature. After the mixture was cooled to 0° C., the mixture was treated by successive dropwise addition of 92 ml of water, 92 ml of 15% sodium hydroxide solution and 276 ml of water. The resulting granular white precipitate was filtered, and the filtrate was concentrated to give (1R,2R,6R)-[2-methoxy-3, 3-dimethyl-6-(1-methylvinyl)cyclohexyl]methanol (784 g, 91% yield).

A mixture of the above alcohol (621 g) and sodium hydride (141 mg, 60% dispersion in oil) and benzyl bromide (0.41 ml) in dry N,N-dimethylformamide (2.5 ml) was stirred for 10 hrs at room temperature. After the mixture was cooled to 0° C., the reaction was quenched by addition of water. The pH of the mixture was adjusted to pH 7 with 0.1N hydrochloric acid. The mixture was extracted with diethyl ether, and the combined organic layers were washed with brine, dried over anhydrous sodium sulfate, filtered, and concentrated. Purification of the residue by flash column chromatography (using n-hexane:ethyl acetate=20:1 as an eluent) gave benzyl [(1S,2R,6R)-2-methoxy-3,3-dimethyl-6-(1-methylvinyl)cyclohexyl]methyl ether (726 mg, 83% yield).

(d) Preparation of [(1R,2R,3R)-2-(benzyloxymethyl)-3-methoxy-4,4-dimethylcyclohexyl]-1-ethanone A stream of O$_3$ was bubbled through a solution of the above olefin (600 mg) in methanol (5 ml) at −78° C. until the blue color persisted. N$_2$ was bubbled through the system, and dimethylsulfide (1.45 ml) was added. The cold bath was removed, and the mixture was allowed to stir at room temperature for 2 hrs. After concentration of the reaction mixture, purification of the residue by silica gel chromatography (using n-hexane:ethyl acetate=10:1 as an eluent) gave [(1R,2R,3R)-2-(benzyloxymethyl)-3-methoxy-4,4-dimethylcyclohexyl]-1-ethanone (450 mg, 75% yield).

(e) Preparation of (1R,2S,3R)-2-(benzyloxymethyl)-3-methoxy-4,4-dimethylcyclohexanol To an ice-cooled mixture of 30% hydrogen peroxide (0.46 ml,) and dichloromethane (2.5 ml), a solution of trifluoroacetic anhydride (0.8 ml) in dichloromethane (0.5 ml) was added dropwise with vigorous stirring over 1 hr period. When the addition was completed, a solution of [(1R,2R, 3R)-2-(benzyloxy-methyl)-3-methoxy-4,4- dimethylcyclohexyl]-1-ethanone (440 mg) in dichloromethane (0.5 ml) was obtained. The addition was carried out over a period of 20 min. The resulting mixture was stirred for 20 hrs at room temperature, and then 10% aqueous sodium sulfite solution was added slowly and stirring continued for 15 min. The organic phase was separated and the aqueous phase was extracted with dichloromethane. The combined organic extracts were washed successively with water, 2N potassium bicarbonate solution and brine, and finally dried over anhydrous sodium sulfate. Evaporation of the solvent in vacuo and chromatography of the residue on silica gel (using n-hexane:ethyl acetate=20:1 as an eluent) gave (1R,2R,3R)-2-(benzyloxymethyl)-3-methoxy-4,4-dimethylcylohexyl acetate (161 mg) and (1R,2R,3R)-2-(benzyloxymethyl)-3-methoxy-4,4-dimethylcyclohexanol (128 mg).

The acetate derivative was converted to the alcohol derivative as follows:

To a solution of the above acetate (161 mg) in dry diethyl ether (2 ml) at 0° C., lithium aluminum hydride (10 mg) was added in small portions. The mixture was stirred for 30 min at room temperature. After the mixture was cooled to 0° C., the mixture was treated by successive dropwise addition of 10 ml of water, 10 ml of 15% sodium hydride solution, and 30 ml of water. The resulting granular precipitate was filtered, and the filtrate was concentrated to give (1R,2R,3R)-2-(benzyloxymethyl)-3-methoxy-4,4-dimethylcyclohexanol (128 mg, 92% yield in total) as colorless oil; EI-MS: m/z 278 (M$^+$); $^1$H-NMR (CDCl$_3$)d: 0.90 (3H,s), 0.98 (3H,s), 1.1–1.9 (5H,m), 2.80 (1H,d,J=11 Hz), 3.40 (3H,s), 3.62 (2H,m), 3.95 (1H,dd,J=3 & 9 Hz), 4.53 (1H,d,J=12 Hz), 4.57 (1H,d,J=12 Hz), 7.33 (5H,m).

Reference Example 13

Preparation of (1R,2R,3R)-2-(benzyloxymethyl)-3-methoxy-4,4-(dimethylcyclohexane-1-carbaldehyde (a) To a mixture of N-chlorosuccinimide (216 mg) and dimethylsulfide (119 ml) in dry toluene (3 ml) there was added a solution of (1R,2R,3R)-2-(benzyloxymethyl)-3-methoxy-4,4-dimethylcyclohexanol (150 mg) in dry toluene (0.5 ml) at −26° C., and the mixture was stirred at −26° C. for 1 hr. To the resulting mixture, trimethylamine (0.37 ml) was added. After 15 min at −26° C., the mixture was allowed to warm to room temperature and stirred for an additional 1 hr. The reaction mixture was diluted with diethyl ether and water was added. The mixture was extracted with ether. The combined ethereal phases were washed with brine, dried over anhydrous sodium sulfate and concentrated. Purification of the residue by silica gel chromatography (using n-hexane:ethyl acetate=10:1 as an eluent) gave (1R,2R,3R)-2-(benzyloxymethyl)-3-methoxy-4,4-dimethyl-1-cyclohexanone (125 mg, 83% yield).

(b) To a stirred suspension of methoxymethyltriphenylphosphonium chloride (460 mg) in dry tetrahydrofuran (2 ml) there was added n-BuLi (0.83 ml, 1.60M in n-hexane) at 0° C. After the mixture was stirred at 0° C. for 30 min, a solution of the above ketone (125 mg) in dry tetrahydrofuran (0.5 ml) was added to the resulting deep orange solution. After 30 min, the mixture was allowed to warm to room temperature, and stirred for an additional 2.5 hrs. The reaction was quenched by addition of saturated aqueous ammonium chloride solution. The mixture was extracted with ether. The combined organic layers were washed with brine, dried over anhydrous sodium sulfate, filtered, and concentrated. Purification of the residue by silica gel chromatography (using n-hexane:ethyl acetate=5:1 as an eluent) gave benzyl [(1R,2R)-2-methoxy-6-(methoxymethylene)-3,3-dimethylcyclohexyl]methyl ether (99 mg, 72% yield).

(c) A mixture of the above enol ether (99 mg) and p-toluenesulfonic acid (2.0 mg) in dichloromethane (2.0 ml) was stirred at room temperature for 1 hr. The reaction mixture was partitioned between saturated aqueous sodium bicarbonate and dichloromethane. The organic layer was washed with brine, dried over anhydrous sodium sulfate, filtered, and concentrated. Purification of the residue by silica gel chromatography gave (1R,2R,3R)-2-(benzyloxymethyl)-3-methoxy-4,4-dimethylcyclohexane-1-carbaldehyde (68 mg, 73% yield) as colorless oil; EI-MS: m/z 290 (M$^+$); 1H-NMR (CDCl$_3$)d: 0.89 (3H,s), 1.02 (3H,s), 1.2–1.6 (3H,m), 2.05 (1H,m), 2.43 (1H,m), 2.80 (1H,d,J=11 Hz), 3.42 (3H, s), 3.54 (1H,dd,J=5 & 9 Hz), 3.63 (1H,dd,J=3 & 9 Hz), 4.43 (1H,d,J=12 Hz), 4.47 (1H,d,J=12 Hz), 7.3 (5H,m), 9.55 (1H,d,J=4 Hz).

Reference Example 14

Preparation of (1R,2R,6S)-[2-methoxy-3,3-dimethyl-6-[(E)-1-nonenyl]cylohexyl]methanol (a) To a stirred solution of n-octyltriphenylphosphonium bromide (313 mg) in dry tetrahydrofuran (0.5 ml) and dry HMPA (0.5 ml), n-BuLi (0.44 ml, 1.6M solution in n-hexane) was added at 0° C. After the mixture was stirred at 0° C. for 30 min, a solution of (1R,2R,3R)-2-(benzyloxymethyl)-3-methoxy-4,4-dimethylcyclohexane-1-carbaldehyde (68 mg) in dry tetrahydrofuran (0.5 ml) was added to the resulting orange solution. The mixture was stirred at 0° C. for 30 min, and at room temperature for 2 hrs. The reaction was quenched by addition of saturated aqueous ammonium chloride solution. The mixture was extracted with diethyl ether, and the combined organic extracts were washed with brine, dried over anhydrous sodium sulfate, filtered, and concentrated. The residue was chromatographed on silica gel (using n-hexane:ethyl acetate=10:1 as an eluent) to give benzyl [(1R,2R,6S)-2-methoxy-3,3-dimethyl-6-[(E)-1-nonenyl]cyclohexyl]methyl ether (54 mg 61%).

(b) A solution of the above benzyl ether (54 mg) in dry tetrahydrofuran was added rapidly to a well-stirred solution of sodium (50 mg) in liquid ammonia (1 ml). The mixture was stirred at −33° C. for 10 min. The reaction was quenched by addition of methanol, and the ammonia was allowed to evaporate. The residue was diluted with water, and extracted with diethyl ether. The organic extracts were washed with brine, dried over anhydrous sodium sulfate, filtered, and concentrated. Purification of the residue with preparative thin layer chromatography (using n-hexane:ethyl acetate=5:1 as an eluent) gave (1R,2R, 6S)-[2-methoxy-3,3-dimethyl-6-[(E)-1-nonenyl]cyclohexyl]methanol (33 mg, 79% yield) as colorless oil; EI-MS: m/z 296 (M$^+$); $^1$H-NMR (CDCl$_3$)d: 0.88 (3H,t,J=6 Hz), 0.90 (3H.,s), 1.03 (3H,s), 1.2–1.5 (15H,m), 2.0 (2H,m), 2.15 (1H,m), 2.87 (1H,d,J=11 Hz), 3.55 (3H,s), 3.60 (1H,dd,J=7 & 11 Hz), 3.73 (1H,dd,J=3 & 11 Hz), 5.18 (1H,dt,J=11 & 8 Hz), 5.39 (1H,tt,J=1 & 11 Hz).

Reference Example 15

Preparation of (1R,2R,6R)-(2-methoxy-3,3-dimethyl-6-octyloxy=cyclohexyl)methanol (a) A mixture of (1R,2R,3R)-2-(benzyloxymethyl)-3-methoxy-4,4-dimethylcyclohexanol (7 mg) and sodium hydride (5 mg, 60% dispersion in oil) and n-octyl bromide (20 ml) in dry N,N-dimethylformamide (0.3 ml) was stirred for 2 hrs at room temperature. The mixture was cooled to 0° C., and the reaction was quenched by addition of water. The pH of the mixture was adjusted to pH 7 with 0.1N hydrochloric acid. The mixture was extracted with diethyl ether, and the combined organic extracts were washed with brine, dried over anhydrous sodium sulfate, filtered, and concentrated. Purification of the residue by preparative thin layer chromatography (using n-hexane:ethyl acetate=10:1 as an eluent) gave benzyl [(1R,2R,6R)-2-methoxy-3,3-dimethyl-6-octyloxycyclohexyl]methyl ether (8 mg, 83%).

(b) The above benzyl ether (8 mg) was subjected to hydrogenolysis over 10% Pd/C (5 mg) in methanol (0.5 ml) for 13 hrs. The mixture was filtered. The filter cake was washed with methanol. The combined filtrate was evaporated to give (1R,2R,6R)-(2-methoxy-3,3-dimethyl-6-octyloxycyclohexyl)methanol (5.5 mg, 89% yield) as colorless oil; EI-MS: m/z 300 (M$^+$); $^1$H-NMR (CDCl$_3$)d: 0.87 (3H,t,J=7 Hz), 0.89 (3H,s), 0.92 (3H,s), 1.2–1.4 (14H,m), 1.7 (1H, m), 1.7–1.9 (2H,m), 2.52 (1H,d,J=11 Hz), 2.73 (1H,dt,J=4 & 11 Hz), 3.1–3.5 (4H,m), 3.55 (3H,s).

Reference Example 16

1) Preparation of (1R*,2R*)-4,4-dimethyl-2-(2-propenyl)=cyclohexanol (a) A solution of 4,4-dimethyl-2-cyclohexen-1-one (500 mg) in dry tetrahydrofuran (2 ml) was added to a well stirred solution of lithium (141 mg) in liquid ammonia (5 ml). The mixture was stirred at −33° C. for 1 hr. And then, to this solution allyl bromide (2.4 g) was added, and stirred for 30 min. The reaction was quenched by addition of methanol, and the ammonia was allowed to evaporate. The residue was diluted with water, and extracted with diethyl ether. The organic extracts were washed with brine, dried over anhydrous sodium sulfate, filtered, and concentrated. Purification of the residue with silica gel column chromatography (using n-hexane:ethyl acetate=30:1 as an eluent) gave 4,4-dimethyl-2-(2-propenyl)cyclohexanone (345 mg, 52% yield) as a colorless oil.

(b) To a solution of lithium tri-tert-butoxyaluminohydride (460 mg) in dry tetrahydrofuran (3.5 ml) there was added a solution of 4,4-dimethyl-2-(2-propenyl)cyclohexanone (250 mg) at 0° C., and the mixture was stirred at room temperature for 2 hrs. The reaction was quenched by addition of water. The pH of the mixture was adjusted to pH 7 with 0.1N hydrochloric acid. The mixture was extracted with diethyl ether, and the combined organic layers were washed with brine, dried over anhydrous sodium sulfate, filtered and concentrated. Purification of the residue by silica gel column chromatography (using n-hexane:ethyl acetate=20:1 as an eluent) gave (1R*,2R*)-4,4-dimethyl-2-(2-propenyl) cyclohexanol (185 mg, 73% yield) as a colorless oil; EI-MS: m/z 168 (M$^+$); $^1$H-NMR (CDCl$_3$)d: 0.90 (3H,s), 0.93 (3H,s), 1.2–1.8 (7H,m), 1.95 (1H,m), 2.46 (1H,m), 3.23 (1H,dt,J=5 & 11 Hz), 5.02 (1H,br.d,J=10 Hz), 5.06 (1H,br.d,J=17 Hz), 5.85 (1H,m).

2) Preparation of (1R*,2R*)-5,5-(dimethyl-2-octyloxycyclohexan-1-yl-ethanol (a) A mixture of (1R*,2R*)-4,4-dimethyl-2-(2-propenyl)=cyclohexanol (150 mg), and sodium hydride (43 mg, 60% dispersion in oil) and n-octyl bromide (180 ml) in dry N,N-dimethylformamide (1 ml) was stirred for 3 hrs at room temperature. The mixture was allowed to cool to 0° C., and the reaction was quenched by addition of water. The pH of the mixture was adjusted to pH 7 with 0.1N hydrochloric acid. The mixture was extracted with diethyl ether, and the combined organic extracts were washed with brine, dried over anhydrous sodium sulfate, filtered and concentrated. Purification of the residue by silica gel column chromatography (using n-hexane:ethyl acetate=20:1 as an eluent) gave (1R*,2R*)-4,4-dimethyl-2-(2-propenyl)=cyclohexyl octyl ether (222 mg, 89% yield) as a colorless oil.

b) A stream of O$_3$ was bubbled through a solution of (1R*,2R*)-4,4-dimethyl-2-(2-propenyl)cyclohexyl octyl ether (200 mg) in methanol (2.5 ml) at −78° C. until the blue color persisted. N$_2$ was bubbled through the system, and dimethyl sulfide (1 ml) was added. The cold bath was removed, and the mixture was allowed to stir at room temperature for 2 hrs. The mixture was concentrated, and the residue was purified by silica gel column chromatography (using n-hexane:ethyl acetate=10:1 as an eluent) gave [(1R*, 2R*)-5,5-dimethyl -2-octyloxycyclohexan-1-yl]-ethanal (151 mg, 75% yield) as a colorless oil; EI-MS: m/z 282 (M$^+$); $^1$H-NMR (CDCl$_3$)d: 0.90 (3H,s), 0.92 (3H,t,J=7 Hz), 0.99 (3H,s), 1.2–1.7 (18H,m), 1.82 (1H,m), 2.14 (1H,m), 2.25 (1H,m), 2.75 (1H,m), 3.20 (1H,m), 3.52 (1H,dt,J=5 & 12 Hz), 9.68 (1H,t,J=2 Hz).

Reference Example 17

Preparation of (2R,3R,4S,5S)-2-[(4-chlorophenylthio) methyl]-4-methoxy-5-methyltetrahydro-2H-pyran-3-ol (a) A mixture of 4,6-O-benzylidene-2-deoxy-2-methyl-3-O-methyl-1,5-anhydro-L-mannitol (400 mg), and NBS (345 mg), and barium carbonate (185 mg) in carbon tetrachloride (10 ml) and 1,1,2,2-tetrachloroethane (0.5 ml) was refluxed for 2 hrs. The hot mixture was filtered. The filter cake was washed with carbon tetrachloride. The combined filtrate was evaporated to give crude product, which was purified by silica gel chromatography (using n-hexane:ethyl acetate=10:1 as an eluent) gave (2R,3R,4S,5S)-2-(bromomethyl)-4-methoxy-5-methyltetrahydro-2H-pyran-3-yl benzoate (231 mg, 42% yield) as colorless oil.

(b) A mixture of the above bromide (20 mg), p-chlorothiophenol (17 mg), sodium hydride (5 mg, 60% dispersion in oil), potassium iodide (14 mg) in dry tetrahydrofuran (0.5 ml) was stirred at room temperature for 13 hrs. The mixture was diluted with water, and the pH of the mixture was adjusted to pH 7 with 0.1N hydrochloric acid. The mixture was extracted with dichloromethane, and the combined organic extracts were washed with brine, dried over anhydrous sodium sulfate, filtered and concentrated. Purification of the residue by preparative thin layer chromatography (using n-hexane:ethyl acetate=10:1 as an eluent) gave (2R,3R,4S,5S)-2-[(4-chlorophenylthio)methyl]-4-methoxy-5-methyltetrahydro-2H-pyran-3-ol (13 mg, 75% yield) as colorless oil; EI-MS: m/z 303 (M$^+$); $^1$H-NMR (CDCl$_3$)d: 0.97 (3H,d,J=6 Hz), 2.25 (1H,m), 2.62 (1H,m), 2.71 (1H,m), 3.13 (1H,m), 3.25 (3H,s), 3.3–3.6 (3H,m), 7.08 (2H,d,J=8 Hz), 7.25 (2H,d,J=8 Hz).

EXAMPLE 1

Preparation of (2S,3R,4S,5S)-4-methoxy-5-methyl-2-[(Z) -1-nonenyl]tetrahydro-2H-pyran-3-yl glycinate trifluoro acetic acid salt a) A mixture of (2S,3R,4S,5S)-4-methoxy-5-methyl-2-[ (Z)-1-nonenyl]tetrahydro-2H-pyran-3-ol (9.0 mg), N-(tert-butoxycarbonyl)glycine (17.5 mg), 4-dimethylamino pyridine (12.0 mg), and dicyclohexylcarbodiimide (21.0 mg) in dry dichloro- methane (0.5 ml) was stirred for 3 hours at room temperature. To the reaction mixture water was added, and the mixture was partitioned between water and dichloromethane. The organic layer was washed with brine, dried over sodium sulfate, filtered, and concentrated. Purification of the residue by preparative thin layer chromatography gave (2S,3R,4S,5S)-4-methoxy-5-methyl-2-[(Z)-1-nonenyl]tetrahydro-2H-pyran-3-yl N-(tert-butoxycarbonyl)glycinate (12.8 mg, y. 91%), EI-MS: m/z 427 (M⁺)

b) A mixture of the above ester (12.8 mg) and trifluoroacetic acid (50 ml) in dry dichloromethane (0.5 ml) was stirred at room temperature for 1 hr. Evaporation of the mixture under reduced pressure gave (2S,3R,4S,5S)-4-methoxy-5-methyl-2-[(Z)-1-nonenyl]tetrahydro-2H-pyran-3-yl glycinate trifluoro acetic acid salt (12.0 mg, y. 92% as colorless oil); EI-MS: m/z 327 (M⁺-CF₃CO₂H); ¹H-NMR (CDCl₃)d: 0.89 (3H,t,J=7 Hz), 1.05 (3H,d,J=8 Hz), 1.28 (10H,m), 1.97 (1H,m), 2.10 (1H,m), 2.26 (1H,m), 3.28 (3H, s), 3.39 (1H, dd,J=5 & 9 Hz), 3.57 (1H,dd,J=2 & 12 Hz), 3.65 (1H, br.d,J=17 Hz), 3.80 (1H,dd,J=2 & 12 Hz), 3.84 (1H,br.d,J=17 Hz), 4.00 (1H,t,J=10 Hz), 4.93 (1H,t,J=9 Hz), 5.29 (1H,t,J=10 Hz), 5.66 (1H,dt,J=8 & 10 Hz)

The following compounds in Example 2–51 were obtained as colorless oil unless stated otherwise in a manner analogous to that of Example 1:

EXAMPLE 2

(2S,3R,4S,5S)-2-[(E)-1-heptenyl]-4-methoxy-5-methyltetra-hydro-2H-pyran-3-yl glycinate trifluoroacetic acid salt; EI-MS: m/z 299 (M⁺-CF₃CO₂H); ¹H-NMR (CDCl₃)d: 0.86 (3H,t,J=7 Hz), 1.04 (3H,d,J=8 Hz), 1.2–1.4 (6H,m), 1.99 (2H,m), 2.26 (1H,m), 3.28 (3H,s), 3.35 (1H, dd,J=5 & 9 Hz), 3.56 (1H,dd,J=2 & 12 Hz), 3.64 (1H,t,J=8 Hz), 3.73 (1H,br.d,J=17 Hz), 3.82 (1H,dd,J=2 & 12 Hz), 3.85 (1H,br.d,J=17 Hz), 4.90 (1H,t,J=9 Hz), 5.38 (1H,dd,J=8 & 16 Hz), 5.77 (1H,dt,J=7 & 16 Hz)

EXAMPLE 3

(2S,3R,4S,5S)-4-methoxy-5-methyl-2-[(E)-1-octenyl]tetra-hydro-2H-pyran-3-yl glycinate trifluoroacetic acid salt; EI-MS: m/z 313 (M⁺-CF₃CO₂H); ¹H-NMR (CDCl₃)d: 0.86 (3H,t,J=7 Hz), 1.05 (3H,d,J=8 Hz), 1.2–1.4 (8H,m), 2.00 (2H,m), 2.71 (1H,m), 3.29 (3H,s), 3.36 (1H,m), 3.56 (1H, d,J=12 Hz), 3.61 (1H,t,J=8 Hz), 3.6–3.9 (2H,br), 3.80 (1H, d,J=12 Hz), 4.91 (1H,t,J=9 Hz), 5.39 (1H,dd,J=7 & 16 Hz), 5.77 (1H,dt,J=16 & 7 Hz).

EXAMPLE 4

(2S,3R,4S,5S)-4-methoxy-5-methyl-2-[(E)-1-nonenyl]-tetrahydro-2H-pyran-3-yl glycinate trifluoroacetic acid salt; EI-MS: m/z 327 (M⁺ -CF₃CO₂H); ¹H-NMR (CDCl₃)d: 0.86 (3H,t,J=6 Hz), 1.04 (3H,d,J=7 Hz), 1.24 (br.s,10H), 2.0 (2H,m), 2.2 (1H,br), 3.28 (3H,s), 3.35 (1H,dd,J=5 & 9 Hz), 3.56 (1H,br.d,J=11 Hz), 3.62 (1H,brt,J=9 Hz), 3.7–3.9 (3H, m), 4.90 (1H,t,J=9 Hz), 5.38 (1H,dd,J=15 & 8 Hz), 5.76 (1H,dt,J=15 & 6 Hz)

EXAMPLE 5

(2S,3R,4S,5S)-4-methoxy-5-methyl-2-nonyl-tetrahydro-2H-pyran-3-yl glycinate formic acid salt; EI-MS: m/z 329 (M⁺-HCO₂H); ¹H-NMR (CDCl₃)d: 0.87 (3H,t,J=6.5 Hz), 1.03 (3H,d,J=7 Hz), 1.25 (12H,br.s), 1.45 (2H,m), 1.7 (2H, m), 2.23 (1H,m), 3.18 (1H,m), 3.28 (1H,dd,J=4.5 & 9.5 Hz), 3.3 (3H,s), 3.5 (1H,dd,J=2.2 & 12 Hz), 3.55 (2H,br.s), 3.78 (1H,dd,J=2 & 12 Hz), 4.8 (3H,br.s), 4.87 (1H,dd,J=9.8 Hz), 8.23 (1H, br.s).

EXAMPLE 6

(2S,3R,4S,5S)-2-[(E)-1-decenyl]-4-methoxy-5-methyltetrahydro-2H-pyran-3-yl glycinate trifluoroacetic acid salt; EI-MS: m/z 341 (M⁺-CF₃CO₂H); ¹H-NMR (CDCl₃)d: 0.87 (3H,t,J=7 Hz), 1.05 (3H,d,J=7 Hz), 1.2–1.4 (12H,m), 1.98 (2H,m), 2.26 (1H,m), 3.29 (3H,s), 3.35 (1H, dd,J=5 & 9 Hz), 3.56 (1H,dd,J=2 & 12 Hz), 3.62 (1H,t,J=8 Hz), 3.6–3.9 (2H, br), 3.81 (1H,dd,J=2 & 12 Hz), 4.90 (1H, t,J=9 Hz), 5.39 (1H,dd,J=8 & 16 Hz), 5.77 (1H,dt,16& 7 Hz).

EXAMPLE 7

(2S,3R,4S,5S)-4-methoxy-5-methyl-2-[(E)-1-undecenyl]-tetrahydro-2H-pyran-3-yl glycinate trifluoroacetic acid salt; EI-MS: m/z 355 (M⁺-CF₃CO₂H); ¹H-NMR (CDCl₃)d: 0.87 (3H,t,J=7 Hz), 1.04 (3H,d,J=8 Hz), 1.25–1.3 (14H,m), 1.99 (2H,m), 2.26 (1H,m), 3.28 (3H,s), 3.36 (1H,dd,J=5 & 9 Hz), 3.56 (1H,br.d,J=12 Hz), 3.62 (1H,t,J=8 Hz), 3.7–3.9 (2H,br), 3.81 (1H,br.d,J=12 Hz), 4.90 (1H,t,J=9 Hz), 5.38 (1H,dd,J=8 & 16 Hz), 5.77 (1H, dt,J=16 & 7 Hz).

EXAMPLE 8

(2S,3R,4S,5S)-2-(4,8-dimethylnonyl)-4-methoxyl-5-methyltetrahydro-2H-pyran-3-yl glycinate trifluoroacetic acid salt; EI-MS: m/z 357 (M⁺-CF₃CO₂H); ¹H-NMR (CDCl₃)d: 0.8–0.9 (12H, m), 1.0–1.6 (14H, m), 2.03 (1H, m), 3.24 (1H, m), 3.40 (1H,t,J=11 Hz), 3.43 (3H, s), 3.5–3.8 (4H,m), 4.91 (1H,t,J=9 Hz).

EXAMPLE 9

(2S,3R,4S,5S)-2-[(1E,3E)-4,8-dimethyl-1,3,7-nonatrienyl]-4-methoxyl-5-methyltetrahydro-2H-pyran-3-yl glycinate trifluoroacetic acid salt; EI-MS: m/z 351 (M⁺-CF₃CO₂H); ¹H-NMR (CDCl₃)d: 1.08 (3H,d,J=7 Hz), 1.46 (3H,s), 1.67 (3H,s), 1.73 (3H, s), 2.04 4H,m), 2.71 (1H,m), 3.25 (3H,s), 3.3–3.9 (6H, m), 4.95 (1H,t,J=9 Hz), 5.48 (2H,m), 5.79 (1H,br.d,J=11 Hz), 6.47 (1H,dd,J=11 & 16 Hz).

EXAMPLE 10

(2S,3R,4S,5S)-2-[(1Z,3E)-4,8,-dimethyl-1,3,7-nonatrienyl]-4-methoxy-5-methyltetrahydro-2H-pyran-3-yl glycinate trifluoroacetic acid salt; EI-MS: m/z 351 (M⁺-CF₃CO₂H); ¹H-NMR (CDCl₃)d: 0.88 (3H,d,J=8 Hz), 1.22 (3H,s), 1.47 (3H,s), 1.75 (3H,s), 2.10 (5H,m), 3.2–3.7 (6H, m), 3.53 (3H, s) (1H,t,J=9 Hz), 5.30 (2H,m), 6.05 (1H,d,J=2 Hz), 6.33 (1H,5,J=11 Hz)

EXAMPLE 11

(2S,3R,4S,5S)-4-methoxy-5-methyl-2-[(1E,3E,5E)-1,3,5-nonatrienyl]tetrahydro-2H-pyran-3-yl glycinate formic acid salt; Amorphous powder; EI-MS: m/z 323 (M⁺-HCO₂H); ¹H-NMR (CDCl₃)d: 0.90 (3H,t,J=6.5 Hz), 1.07 (3H,d,J=6.7 Hz), 1.40 (2H,m), 2.07 (2H,dd,J=6.5 & 14 Hz), 2.27 (1H,m), 3.32 (3H,s), 3.47–3.71 (5H,m), 3.83 (1H,dd, J=2.5 & 12 Hz), 4.93 (1H,t,J=8.1 Hz), 5.54 (4H,br.m), 5.73 (1H,m), 6.0–6.25 (4H,m), 8.24 (1H,br.s).

EXAMPLE 12

(2S,3R,4S,5S)-4-methoxy-5-methyl-2-[(1Z,3E,5E)-1,3,5-nonatrienyl]tetrahydro-2H-pyran-3-yl glycinate formic acid salt; EI-MS: m/z 323 (M⁺-HCO₂H); ¹H-NMR (CDCl₃) d: 0.91 (3H,t,J=6.5 Hz), 1.08 (3H,d,J=6.5 Hz), 1.43 (2H,m), 2.09 (2H,dd,J=6.5 & 14 Hz), 2.28 (1H,m), 3.36 (3H,s), 3.41 (1H,dd,J=5 & 8.3 Hz), 3.4 (1H,m), 3.50 (1H,m), 3.57 (1H,dd,J=2.5 & 12 Hz), 3.82 (1H,dd,J=2.3 & 12 Hz), 4.15 (1H,dd,J=8.3 Hz), 4.95 (1H,dd,J=8.3 Hz), 5.31 (1H,dd,J=8.3 & 10 Hz), 5.80 (4H,br.m), 6.06–6.31 (4H,m), 8.2 (1H, br.s).

EXAMPLE 13

(2S,3R,4S,5S)-2-[(E)-2-(4-chlorophenyl)vinyl]-4-methoxy-5-methyltetrahydro-2H-pyran-3-yl glycinate trifluoroacetic acid salt; EI-MS: m/z 340 ($M^+$-$CF_3CO_2H$); $^1$H-NMR (CDCl$_3$)d: 1.04 (3H,d,J=7 Hz), 2.27 (1H,m), 3.42 (3H,s), 3.39 (1H,m), 3.61 (1H,d,J=11 Hz), 3.6–3.9 (3H,m), 3.85 (1H,d,J=11 Hz), 4.95 (1H,t,J=9 Hz), 6.08 (1H,dd,J=6 & 16 Hz), 6.59 (1H,d,J=16 Hz), 7.23 (4H,s).

EXAMPLE 14

(2S,3R,4S,5S)-2-[(Z)-2-(4-chlorophenyl)vinyl]-4-methoxy-5-methyltetrahydro-2H-pyran-3-yl glycinate trifluoroacetic acid salt; EI-MS: 340 ($M^+$-$CF_3CO_2H$); $^1$H-NMR (CDCl$_3$)d: 1.05 (3H,d,J=7 Hz), 2.29 (1H,m), 3.27 (3H,s), 3.35 (1H,dd,J=5 & 9 Hz), 3.60 (1H,d,J=11 Hz), 3.6–3.8 (2H,m), 3.85 (1H,d,J=11 Hz), 4.02 (1H,t,J=9 Hz), 5.05 (1H,t,J=9 Hz), 5.61 (1H,t,J=10 Hz), 6.69 (1H,d,J=11 Hz), 7.23 (2H,d,J=8 Hz), 7.31 (2H,d,J=8 Hz).

EXAMPLE 15

(2S,3R,4S,5S)-2-[2-(4-chlorophenyl)ethyl]-4-methoxy-5-methyltetrahydro-2H-pyran-3yl glycinate trifluoroacetic acid salt; EI-MS: m/z 342 ($M^+$-$CF_3CO_2H$); $^1$H-NMR (CDCl$_3$)d: 1.00 (3H,d,J=7 Hz), 2.23 (1H,m), 2.99 (1H,dd, J=8 & 14 Hz), 3.10 (1H,dd,J=3 & 14 Hz), 3.26 (3H,s), 3.30 (1H,dd,J=5 & 9 Hz), 3.49 (1H,m), 3.78 (1H,dd,J=3 & 12 Hz), 3.85 (2H,br.s), 5.06 (1H,t,J=9 Hz), 7.20 (2H,d,J=9 Hz), 7.27 (2H,d,J=9 Hz)

EXAMPLE 16

(2S,3R,4S,5S)-4-methoxy-5-methyl-2-[(E)-2-naphthylvinyl]=tetrahydro-2H-pyran-3-yl glycinate trifluoroacetic acid salt; EI-MS: m/z 355 ($M^+$-$CF_3CO_2H$); $^1$H-NMR (CDCl$_3$)d: 1.12 (1H,d,J=7 Hz), 2.31 (1H,m), 3.44 (1H,dd,J=5 & 9 Hz), 3.66 (1H,dd,J=2 & 12 Hz), 3.90 (2H,m), 5.05 (1H,t,J=9 Hz), 6.25 (1H,dd,J=7 & 16 Hz), 6.78 (1H,d,J=16 Hz), 7.45 (2H,m), 7.56 (1H,dd,J=2 & 8 Hz), 7.7–7.8 (4H,m).

EXAMPLE 17

(2S,3R,4S,5S)-4-methoxy-5-methyl-2-(2-naphthylethyl)tetra=hydro-2H-pyran-3yl glycinate trifluoroacetic acid salt; EI-MS: m/z 357 ($M^+$-$CF_3CO_2H$); $^1$H-NMR (CDCl$_3$)d: 1.07 (3H,d,J=7 Hz), 1.86 (2H,m), 2.24 (1H,m), 2.80 (1H,m), 3.00 (1H,m), 3.22 (1H,m), 3.28 (1H,dd,J=5 & 10 Hz), 3.29 (3H,s), 3.52 (1H,dd,J=2 & 12 Hz), 3.84 (1H,dd,J=2 & 12 Hz), 3.90 (2H,m), 4.94 (1H,t,J=9 Hz), 7.32 (1H,m), 7.42 (2H,m), 7.44 (1H,br.s), 7.77 (3H,m).

EXAMPLE 18

(2S,3R,4S,5S)-4-methoxy-5-methyl-2-[4-(4-methylphenyl)=butyl]tetrahydro-2H-pyran-3-yl glycinate trifluoroacetic acid salt; EI-MS: m/z 361 ($M^+$-$CF_3CO_2H$); $^1$H-NMR (CDCl$_3$)d: 1.03 (3H;d,J=7 Hz), 1.1–1.51 (6H,m), 2.22 (1H,m), 2.55 (2H,m), 3.16 (1H,m), 3.28 (1H,dd,J=5 & 9 Hz), 3.30 (3H,s), 3.48 (1H,dd,J=2 & 12 Hz), 3.76 (1H dd,J=2 & 12 Hz), 3.9 (2H,m), 4.86 (1H,t,J=9 Hz), 7.60 (4H,m).

EXAMPLE 19

(2S,3R,4S,5S)-4-methoxy-5-methyl-2-(1-nonynyl)tetrahydro-2H-pyran-3-yl glycinate trifluoroacetic acid salt; EI-MS m/z 325 ($M^+$-$CF_3CO_2H$); $^1$H-NMR (CDCl$_3$)d: 0.87 (3H,t,J=7 Hz), 1.00 (3H,d,J=7 Hz), 1.2–1.6 (10H,m), 2.18 (3H,m), 3.30 (1H,m), 3.34 (3H,s), 3.48 (1H,d,J=12 Hz), 3.84 (3H,m), 4.16 (1H,d,J=7 Hz), 5.09 (1H,t,J=7 Hz).

EXAMPLE 20

(2R,3R,4S,5S)-2-(4-chlorophenylthio)methyl-4-methoxy-5methyltetrahydro-2H-pyran-3-yl glycinate trifluoroacetic acid salt; EI-MS: m/z 360 ($M^+$-$CF_3CO_2H$); $^1$H-NMR (CDCl$_3$)d: 0.99 (3H,d,J=6 Hz), 2.22 (1H,m), 2.61 (1H,m), 2.74 (1H,m), 3.13 (1H,m), 3.25 (3H,s), 3.27 (1H, m), 3.49 (1H,d,J=12 Hz), 3.7–3.9 (2H,m), 3.80 (1H,d,J=12 Hz), 7.07 (2H,d,J=8 Hz), 7.20 (2H d,J=8 Hz).

EXAMPLE 21

(2S,3R,4S,5S)-5-methyl-2-[(E)-1-nonenyl]-4-propoxytetrahydro-2H-pyran-3-yl glycinate trifluoroacetic acid salt; EI-MS: m/z 355 ($M^+$-$CF_3CO_2H$); $^1$H-NMR (CDCl$_3$)d: 0.87 (6H,t,J=6 Hz), 1.04 (3H,d,J=6 Hz), 1.26 (10H,br.s), 1.53 (2H,m), 2.00 (2H,m), 2.22 (1H,br.s), 3.28 (1H,m), 3.45 (2H,m), 3.55 (1H,d,J=11 Hz), 3.69 (1H,t,J=8 Hz), 3.79 (3H,m), 4.92 (1H,t,J=8 Hz), 5.45 (1H,dd,J=15& 7 Hz), 5.77 (1H,dt,J=15 & 6 Hz).

EXAMPLE 22

(2S,3R,4S,5-S)-5-methyl-2-[(Z)-1-nonenyl]-4-prpoxytetrahydro-2H-pyran-3-yl glycinate trifluoroacetic acid salt; EI-MS: m/z 355 ($M^+$-$CF_3CO_2H$); $^1$H-NMR (CDCl$_3$)d: 0.87 (6H,m), 1.05 (3H,d,J=7 Hz), 1.26 (10H,br.s), 1.52 (2H,dq, J=14 & 7 Hz), 1.96 (1H,m), 2.11 (1H,m), 2.22 (1H,m), 3.28 (1H,dt,J=10 & 6 Hz), 3.44–3.49 (2H,m), 3.57 (1H,d,J=10 Hz), 3.68–3.81 (3H,m), 4.04 (1H,t,J=9 Hz), 4.95 (1H,t,J=9 Hz), 5.36 (1H,t,J=9 Hz), 5.66 (1H,dt,J=9 & 8 Hz).

EXAMPLE 23

2S,3R,4S,5S)-5-methyl-2-nonyl-4-propoxytetrahydro-2-H-pyran-3-yl glycinate trifluoroacetic acid salt; EI-MS: m/z 327 ($M^+$-$CF_3CO_2H$); $^1$H-NMR (CDCl$_3$)d: 0.84–0.89 (6H, m), 1.01 (3H,d,J=7 Hz), 1.25 (14H,br.s), 1.46–1.56 (4H,m), 2.19 (1H,m), 3.25 (2H,m), 3.39 (1H,dd,J=5 & 9 Hz), 3.45 (2H,m), 3.75 (1H,dd,J=3 & 12 Hz), 3.81–3.93 (2H,m), 4.87 (1H,t,J=9 Hz).

EXAMPLE 24

(2S,3R,4S,5S)-4-methoxy-5-methyl-2-[(E)-1-nonenyl] tetra-hydro-2H-pyran-3-yl glycinate trifluoroacetic acid salt; EI-MS: m/z 327 ($M^+$-$CF_3CO_2H$); $^1$H-NMR (CDCl$_3$)d: 0.88 (3H,t,J=7 Hz), 0.98 (3H,d,J=7 Hz), 1.27 (10H,br.s), 2.02–2.11 (3H,m), 3.25 (1H,dd,J=8 & 3 Hz), 3.34 (3H,s), 3.41 (1H,dd,J=12 & 8 Hz), 3.74 (1H,dd,J=12 & 4 Hz), 3.81–3.91 (2H,m), 4.33 (1H,br.t,J=6 Hz), 5.16 (1H,m), 5.41 (1H,dd,J=15 & 6 Hz), 5.80 (1H,dt,J=15 & 7 Hz)

EXAMPLE 25

(2S,3R,4R,5S)-4-methoxy-5-methyl -2-[(Z)-1-nonenyl] tetra-hydro-2H-pyran-3-yl glycinate trifluoroacetic acid salt; EI-MS: m/z 327 ($M^+$-$CF_3CO_2H$); $^1$H-NMR (CDCl$_3$)d: 0.88 (3H,t,J=7 Hz), 1.02 (3H,d,J=6 Hz), 1.27–1.36 (10H,m), 2.02–2.18 (3H,m), 3.30 (1H,br.d,J=5 Hz), 3.35 (3H,s), 3.42 (1H,dd,J=12 & 6 Hz), 3.78 (3H,m), 4.61 (1H,br.t-like), 5.09 (1H,br.d-like), 5.37 (1H,t,J=9 Hz), 5.68 (1H,dt,J=10 & 8 Hz)

EXAMPLE 26

(2S,3R,4R,5S)-4-methoxy-5-methyl-2-nonyltetrahydro-2H-pyran-3-yl glycinate trifluoroacetic acid salt; EI-MS: m/z 329 ($M^+$-$CF_3CO_2H$); $^1$H-NMR (CDCl$_3$)d: 0.88 (3H,t, J=7 Hz), 1.01 (3H,d,J=7 Hz), 1.26 (14H,br.s), 1.45–1.52 (2H,m), 2.07 (1H,m), 3.29 (1H,dd,J=7 & 3 Hz), 3.36 (3H,s), 3.37 (1H,m), 3.73 (1H,dd,J=12 & 4 Hz), 3.79 (1H,br.t-like), 3.88 (2H,br.s), 5.03 (1H,m)

EXAMPLE 27

(2S,3R,4S,5S)-4-ethoxy-5-methyl-2-[(Z)-1-nonenyl] tetrahydro-2H-pyran-3-yl glycinate trifluoroacetic acid salt; EI-MS m/z 341 (M$^+$-CF$_3$CO$_2$H); $^1$H-NMR (CDCl$_3$)d: 0.81 (3H,t,J=7 Hz), 0.98 (3H,d,J=7 Hz), 1.07 (3H,t,J=7 Hz), 1.20 (10H,br.s), 1.90 (1H,m), 2.05 (1H,m), 2.16 (1H,m), 3.32 (1H,t,J=9 Hz), 3.41 (1H,dd,J=9 & 5 Hz), 3.50 (2H,d,J=10 Hz), 3.59–3.63 (2H,m), 3.71 (1H,d,J=10 Hz), 3.96 (1H,t,J=9 Hz), 4.88 (1H,t,J=9 Hz), 5.29 (1H,t,J=10 Hz), 5.58 (1H,dt, J=9 & 8 Hz)

EXAMPLE 28

(2S,3R,5R)-5-methyl-2-[(E)-1-nonenyl]tetrahydro-2H-pyran-3-yl glycinate trifluoroacetic acid salt; EI-MS: m/z 297 (M$^+$-CF$_3$CO$_2$H); $^1$H-NMR (CDCl$_3$)d: 0.88 (3H,t,J=7 Hz), 1.01 (3H,d,J=7 Hz), 1.25–1.35 (10H,m), 1.76 (2H,m), 2.03–2.10 (3H,m), 3.51–3.61 (4H,m), 3.88 (1H,t,J=7 Hz), 4.91 (1H,m), 5.46 (1H,dd,J=16 & 7 Hz), 5.76 (1H,dt,J=16 & 7 Hz)

EXAMPLE 29

(2S,3R,4S,5R)-4,5-dimethoxy-2-[(E)-1-nonenyl] tetrahydro-2H-pyran-3-yl glycinate trifluoroacetic acid salt; EI-MS: m/z 343 (M$^+$-CF$_3$CO$_2$H); $^1$H-NMR (CDCl$_3$)d: 0.87 (3H,t,J=7 Hz), 1.25–1.30 (10H,m), 1.98 (2H,m), 3.16 (1H, t,J=11 Hz), 3.26 (1H,t,J=9 Hz), 3.36 (1H,dd,J=10 & 5 Hz), 3.47–3.53 (8H,m), 3.64 (1H,t,J=9 Hz), 4.08 (1H,dd,J=11 & 5 Hz), 4.76 (1H,t,J=10 Hz), 5.28 (1H,dd,J=15 & 7 Hz), 5.78 (1H,dt,J=15 & 7 Hz)

EXAMPLE 30

(2S,3R,4S,5R)-5-ethoxy-4-methoxy-2-[(E)-1-nonenyl] tetra-hydro-2H-pyran-3-yl glycinate trifluoroacetic acid salt; EI-MS: m/z 357 (M$^+$-CF$_3$CO$_2$H); $^1$H-NMR (CDCl$_3$)d: 0.87 (3H,t,J=7 Hz), 1.18–1.32 (13H,m), 1.98 (2H,m), 3.18 (1H, t,J=11 Hz), 3.25 (1H,t,J=9 Hz), 3.46 (1H,dt,J=10 & 4 Hz), 3.50 (3H,s), 3.61–3.68 (5H,m), 4.04 (1H,dd,J=11 & 5 Hz), 4.75 (1H,t,J=10 Hz), 5.28 (1H,dd,J=15 & 7 Hz), 5.78 (1H,dt,J=15 & 7 Hz)

EXAMPLE 31

(2S,3R,4S,5R)-5-benzyloxy-4-methoxy-2-[(E)-1-nonenyl]tetra-hydro-2H-pyran-3-yl glycinate trifluoroacetic acid salt; EI-MS: m/z 419 (M$^+$-CF$_3$CO$_2$H); $^1$H-NMR (CDCl$_3$)d: 0.86 (3H,t,J=7 Hz), 1.23–1.29 (10H,m), 1.97 (2H,m), 3.21 (1H,t,J=11 Hz), 3.34 (1H,t,J=9 Hz), 3.52 (3H,s), 3.57 (1H,dd,J=10 & 4 Hz), 3.61–3.66 (3H,m), 3.98 (1H,dd,J=11 & 5 Hz), 4.59 (1H,d,J=11 Hz), 4.69 (1H,d,J=11 Hz), 4.77 (1H,t,J=10 Hz), 5.27 (1H,dd,J=15 & 7 Hz), 5.77 (1H,dt,J=15 & 7 Hz), 7.27–7.35 (5H,m).

EXAMPLE 32

(2S,3R,4S,5R)-4-methoxy-2-nonyl-5-(3-phenylpropoxy) tetra-hydro-2H-pyran-3-yl glycinate trifluoroacetic acid salt; EI-MS: m/z 449 (M$^+$-CF$_3$CO$_2$H); $^1$H-NMR (CDCl$_3$)d: 0.86 (3H,t,J=7 Hz), 1.24–1.37 (15H,m), 1.42 (1H,m), 1.86 (2H, m), 2.66 (2H,t,J=8 Hz), 3.09 (1H,t,J=11 Hz), 3.17–3.23 (2H,m), 3.39 (1H,m), 3.50 (3H,s), 3.56 (2H,t,J=7 Hz), 3.86 (1H,br.s), 4.01 (1H,dd,J=11 & 5 Hz), 4.70 (1H,t,J=10 Hz), 7.15–7.19 (2H,m), 7.25–7.19 (3H,m)

EXAMPLE 33

(2S,3R,4S,5R)-5-(4-tert-butylbenzyloxy)-4-methoxy-2-[(E)-1-nonenyl]tetrahydro-2H-pyran-3-yl glycinate trifluoroacetic acid salt; EI-MS: m/z 475 (M$^+$-CF$_3$CO$_2$H); $^1$H-NMR (CDCl$_3$)d: 0.86 (3H,t,J=7 Hz), 1.23 (10H,br.s), 1.30 (9H,s), 1.97 (2H,m), 3.19 (1H,t,J=11 Hz), 3.34 (1H,t, J=9 Hz), 3.54 (3H,s), 3.58 (1H,dd,J=10 & 6 Hz), 3.63 (1H,t,J=9 Hz), 3.72 (1H,d,J=18 Hz), 3.84 (1H,d,J=18 Hz), 3.97 (1H,dd,J=12 & 6 Hz), 4.55 (1H,d,J=11 Hz), 4.68 (1H,d,J=11 Hz), 4.77 (1H,t,J=10 Hz), 5.27 (1H,dd,J=15 & 7 Hz), 5.77 (1H,dt,J=15 & 7 Hz), 7.25 (2H,d,J=8 Hz), 7.36 (2H,d,J=8 Hz)

EXAMPLE 34

(2S,3R,4S,5R)-5-(2,4-difluorobenzyloxy)-4-methoxy-2-[(E)-1-nonenyl]tetrahydro-2H-pyran-3-yl glycinate trifluoroacetic acid salt; EI-MS: m/z 455 (M$^+$-CF$_3$CO$_2$H); $^1$H-NMR (CDCl$_3$)d: 0.86 (3H,t,J=7 Hz), 1.23–1.31 (10H, m), 1.97 (2H,m), 3.21 (1H,t,J=11 Hz), 3.31 (1H,t,J=9 Hz), 3.49 (3H,s), 3.57–3.66 (2H,m), 3.75–3.86 (2H,m), 4.02 (1H,dd,J=11 & 5 Hz), 4.62 (1H,d,J=12 Hz), 4.69 (1H,d,J=12 Hz), 4.77 (1H,t,J=9 Hz), 5.27 (1H,dd,J=15 & 7 Hz), 5.77 (1H,dt,J=15 & 7 Hz), 6.79 (1H,dt,J=10 & 2 Hz), 6.86 (1H,dt,J=8 & 2 Hz), 7.34 (1H,dt,J=8 & 7 Hz).

EXAMPLE 35

(2S,3R,4S,5R)-5-butoxy-4-methoxy-2-[(E)-1-nonenyl] tetra-hydro-2H-pyran-3-yl glycinate trifluoroacetic acid salt; EI-MS: m/z 385 (M$^+$-CF$_3$CO$_2$H); $^1$H-NMR (CDCl$_3$)d: 0.87 (3H,t,J=7 Hz), 0.92 (3H,t,J=7 Hz), 1.24–1.39 (12H,m), 1.52 (2H,m), 1.98 (2H,m), 3.17 (1H,t,J=11 Hz), 3.24 (1H,t,J=9 Hz), 3.43 (1H,dt,J=10 & 4 Hz), 3.50 (3H,s), 3.58 (1H,t,J=7 Hz), 3.63 (1H,t,J=8 Hz), 3.71 (1H,d,J=18 Hz), 3.84 (1H,d, J=18 Hz), 4.04 (1H,dd,J=12 & 6 Hz), 4.74 (1H,t,J=10 Hz), 5.28 (1H,dd,J=15 & 8 Hz), 5.77 (1H,dt,J=15 & 7 Hz).

EXAMPLE 36

(2S,3R,4S,5R)-5-(2-hydroxyethoxy)-4-methoxy-2-nonyltetra-hydro-2H-pyran-3-yl glycinate trifluoroacetic acid salt; EI-MS: m/z 375 (M$^+$-CF$_3$CO$_2$H); $^1$H-NMR (CDCl$_3$)d: 0.88 (3H,t,J=7 Hz), 1.25 (12H,br.s), 1.31–1.45 (2H,m), 2.07 (2H,br.s), 3.11–3.28 (3H,m), 3.48–3.54 (6H, m), 3.68–3.77 (4H,m), 4.03 (1H,dd,J=12 & 5 Hz), 4.77 (1H,t,J=9 Hz).

EXAMPLE 37

(2S,3R,4S,5R)-5-(2-hydroxy-2-methylpropoxy)-4-methoxy-2-nonyltetrahydro-2H-pyran-3-yl glycinate trifluoroacetic acid salt; FAB-MS: m/z 404 (MH$^+$-CF$_3$CO$_2$H); $^1$H-NMR (CDCl$_3$)d: 0.87 (3H;;t,J=7 Hz), 1.21 (3H,s), 1.24 (17H,s), 1.40 (2H,m), 3.17 (1H,t,J=12 Hz), 3.28 (1H,br.t,J=9 Hz), 3.35 (1H,t,J=9 Hz), 3.39 (1H,d,J=10 Hz) 3.47–3.54 (2H,m), 3.48 (3H,s), 3.95 (2H,br.s), 4.04 (1H,dd,J=12 & 5 Hz), 4.76 (1H,t,J=9 Hz), 6.47 (1H,br.s).

EXAMPLE 38

(2S,3R,4S,5R)-4-methoxy-2-nonyl-5-(2-oxopropoxy) tetrahydro -2H-pyran-3-yl glycinate trifluoroacetic acid salt; FAB-MS: m/z 388 (MH$^+$-CF$_3$CO$_2$H); $^1$H-NMR (CDCl$_3$)d: 0.87 (3H,t,J=7 Hz), 1.24–1.43 (16H,m), 2.12 (3H,s), 3.21 (1H,t,J=11 Hz), 3.26 (1H,t,J=9 Hz), 3.35 (1H,t,J=9 Hz), 3.43–3.53 (1H,m), 3.48 (3H,s), 3.94 (2H,br.s), 4.08 (1H,dd, J=11 & 4 Hz), 4.28 (2H,s), 4.71 (1H,t,J=9 Hz).

EXAMPLE 39

(2S,3R,4S,5R)-4-methoxy-2-nonyl-5-[2-(1H-1,2,4-triazol-1-yl)ethoxy]tetrahydro-2H-pyran-3-yl glycinate trifluoroacetic acid salt; EI-MS: m/z 426 (M$^+$-CF$_3$CO$_2$H); $^1$H-NMR (CDCl$_3$)d: 0.87 (3H,t,J=7 Hz), 1.24–1.60 (14H, m), 1.95 (2H,br.s), 3.00 (1H,t,J=11 Hz), 3.13 (1H,t,J=9 Hz), 3.32 (3H,s), 3.35–3.44 (1H,m), 3.48 (1H,br.s), 3.87 (1H,dd, J=11 & 5 Hz), 3.92–4.05 (2H,m), 4.33 (2H,m), 4.70 (1H,t, J=10 Hz), 7.94 (1H,s), 8.13 (1H,s).

EXAMPLE 40

(2S,3R,4S,5S)-2-heptylcarbamoyl-4-methoxy-5-methyltetra-hydro-2H-pyran-3-yl-glycinate formic acid salt; EI-MS: m/z 344 (M$^+$-HCO$_2$H); $^1$H-NMR (CDCl$_3$)d: 0.90 (3H,t,J=6.5 Hz), 1.10 (3H,d,J=7 Hz), 1.23 (10H,br.s), 2.3 (1H,m), 3.2–3.55 (7H,br.m), 3.3 (3H,s), 3.8 (1H,dd,J=2.5 & 12 Hz), 4.9 (1H,t,J=9.9 Hz), 5.0 (3H,br.s), 8.0 (2H,br.s).

EXAMPLE 41

(2S,3R,4S,5S)-2-(heptyloxymethyl)-4-methoxy-5-methyltetra-hydro-2H-pyran-3-yl glycinate trifluoroacetic acid salt; EI-MS: m/z 331 (M$^+$-CF$_3$CO$_2$H); $^1$H-NMR (CDCl$_3$)d: 0.87 (3H,t,J=7 Hz), 1.04 (3H,d,J=7 Hz), 1.26 (10H,m), 2.24 (1H,m), 3.32 (3H,s), 3.33 (1H,dd,J=9 & 5 Hz), 3.39–3.48 (7H,m), 3.55 (1H,dd,J=12 & 2 Hz), 3.83 (1H,dd,J=12 & 2 Hz), 4.97 (1H,t,J=9 Hz).

EXAMPLE 43

(2S,3R,4S,5R)-4-methoxy-5-methyl-2-[(Z)-1-nonenyl]tetrahydro-2H-pyran-3-yl glycinate trifluoroacetic acid salt; FAB-MS: m/z 328 (MH$^+$-CF$_3$CO$_2$H); $^1$H-NMR (CDCl$_3$)d: 0.88 (3H,t,J=6 Hz), 0.97 (3H,d,J=6 Hz), 1.27 (10H,br.s), 1.95 (2H,m), 2.12 (1H,m), 3.02 (1H,t,J=10 Hz), 3.13 (1H, t,J=12 Hz), 3.40 (3H,s), 3.66 (1H,br.d,J=18 Hz), 3.84 (2H, m), 4.02 (1H,t,J=10 Hz), 4.85 (1H,t,J=10 Hz), 5.24 (1H,t, J=10 Hz), 5.67 (1H,dd,J=10 & 15 Hz).

EXAMPLE 43

(2S,3R,4S,5R)-4-methoxy-5-methyl-2-nonyltetrahydro-2H-pyran-3-yl glycinate trifluoroacetic acid salt; FAB-MS: m/z 390 (MH$^+$-CF$_3$CO$_2$H); $^1$H-NMR (CDCl$_3$)d: 0.87 (3H, t,J=7 Hz), 0.94 (3H,d,J=7 Hz), 1.25 (14H,br.s), 1.43 (2H,m), 1.89 (1H,m), 2.95 (1H,t,J=10 Hz), 3.03 (1H,t,J=12 Hz), 3.21 (1H,t,J=10 Hz), 3.38 (3H,s), 3.81 (1H,dd,J=5 & 12 Hz), 3.86 (2H,s), 4.77 (1H,t,J=10 Hz).

EXAMPLE 44

(2S,3R,4S,5R)-4-methoxy-5-methyl-2-[(E)-1-nonenyl]tetrahydro-2H-pyran-3-yl glycinate trifluoroacetic acid salt; FAB-MS: m/z 328 (MH$^+$-CF$_3$CO$_2$H); $^1$H-NMR (CDCl$_3$)d: 0.88 (3H,t,J=6 Hz), 0.95 (3H,d,J=6 Hz), 1.26 (10H,br.s), 1.97 (3H,m), 3.00 (1H,t,J=10 Hz), 3.10 (1H,t,J=12 Hz), 3.38 (3H,s), 3.65 (1H,t,J=8 Hz), 3.71 (1H,br.d,J=17 Hz), 3.83 (2H,m), 4.81 (1H,t,J=10 Hz), 5.33 (1H,dd,J=8 & 15 Hz), 5.76 (1H,dt,J=8 & 15 Hz).

EXAMPLE 45

(9S,10R,11R)-11-methoxy-9-[(E)-1-nonenyl]-8-oxa-1,5-dithiaspiro[5,5]undecan-10-yl glycinate formic acid salt; EI-MS: m/z 417 (M$^+$-HCO$_2$H); $^1$H-NMR (CDCl$_3$)d: 0.87 (3H,t,J=7 Hz), 1.25 (10H,m), 1.97 (4H,m), 2.72 (1H,m), 2.88 (1H,m), 3.00 (1H,m), 3.13 (1H,m), 3.43 (1H,d,J=9 Hz), 3.49 (2H,d,J=12 Hz), 3.58 (3H,s), 3.63 (1H,t,J=9 Hz), 4.22 (1H,d,J=12 Hz), 5.27 (1H,t,J=9 Hz), 5.41 (1H,dd,J=8 & 16 Hz), 5.74 (1H,dt,J=6 & 16 Hz).

EXAMPLE 46

(6S,7S,10S)-10-methyl-7-[(E)-1-nonenyl]-1,4,8-trioxaspiro[4,5]decan-6-yl glycinate trifluoroacetic acid salt; FAB-MS: m/z: 356 (MH$^+$-CF$_3$CO$_2$H); $^1$H-NMR (CDCl$_3$)d: 0.87 (3H,t,J=6.6 Hz), 1.07 (3H,d,J=6.8 Hz), 1.26–1.44 (10H, br.m), 2.0.(3H,br.m), 3.65 (1H,dd,J=3.7 & 11.7 Hz), 3.78–4.05 (11H,br.m), 4.98 (1H,d,J=8.1 Hz), 5.47 (1H,dd, J=7.3 & 15.4 Hz), 5.78 (1H,dt,J=7.3 & 15.4 Hz).

EXAMPLE 47

(2S,3R,4S,5S)-4-methoxy-5-methyl-2-[(1E,3E)-1,3-nonadienyl]tetrahydro-2H-pyran-3-yl glycinate formic acid salt; EI-MS: m/z 325 (M$^+$-HCO$_2$H); $^1$H-NMR (CDCl$_3$)d: 0.88 (3H,t,J=6.5 Hz), 1.07 (3H,d,J=6.5 Hz), 1.24–1.38 (6H, br.m), 2.04 (2H,q,J=6.5 Hz), 2.26 (1H,m), 3.32 (3H,s), 3.34 (1H,dd,J=3.8 & 9 Hz), 3.43 (1H,d,J=15.0 Hz), 3.53 (1H,d, J=15.0 Hz), 3.58 (1H,dd,J=2.5 & 10.0 Hz), 3.65 (1H,dd,J= 7.5 & 9.0 Hz), 3.82 (1H,dd,J=2.1 & 10.0 Hz), 4.93 (1H,t, J=9.0 Hz), 5.01 (3H,br.s), 5.47 (1H,dd,J=7.5 & 15.0 Hz), 5.71 (1H,dt,J=6.5 & 15.0 Hz), 6.0 (1H,dd,J=10.0,& 15.0 Hz), 6.21 (1H,dd,J=10.0 & 15 Hz), 8.08 (1H,s).

EXAMPLE 48

(2S,3R,4S)-4-methoxy-2-[(Z)-1-nonenyl]tetrahydro-2H-pyran-3-yl glycinate trifluoroacetic acid salt; FAB-MS: m/z 314 (M$^+$-CF$_3$CO$_2$H); $^1$H-NMR (CDCl$_3$)d: 0.88 (3H,br.t), 1.27 (10H,br.s), 1.67 (1H,br.m), 1.99 (1H,br.m), 2.14 (2H, br.m), 3.34 (3H,s), 3.36–3.49 (5H,br.m), 3.67 (1H,br.m), 3.88 (1H,br.m), 4.03 (2H,br.m), 4.80 (1H,br.m), 5.28 (1H, br.m), 5.68 (1H,br.m).

EXAMPLE 49

(2S,3R,4S,5S)-4-methoxy-5-methyl-2-[(E)-2-(4-propylphenyl)vinyl]tetrahydro-2H-pyran-3-yl glycinate trifluoroacetic acid salt; EI-MS: m/z 347 (M$^+$-CF$_3$CO$_2$H); $^1$H-NMR (CDCl$_3$)d: 1.03 (3H,d,J=7 Hz), 1.06 (3H,t,J=8 Hz), 1.72 (2H,m), 2.1–2.3 (3H,m), 3.42 (3H,s), 3.40 (1H,m), 3.62 (1H,d,J=12 Hz), 3.6–3.9 (3H,m), 3.89 (1H,d,J=12 Hz), 4.96 (1H,t,J=9 Hz), 6.09 (1H,dd,J=6 & 16 Hz), 6.60 (1H,d, J=16 Hz), 7.26 (4H,s).

EXAMPLE 50

(2S,3R,4S,5R)-4-methoxy-5-methyl-2-[2-(4-propylphenyl)ethyl]tetrahydro-2H-pyran-3-yl glycinate trifluoroacetic acid salt; EI-MS: m/z 349 (M$^+$-CF$_3$CO$_2$H); $^1$H-NMR (CDCl$_3$)d: 0.97 (3H,d,J=7 Hz), 1.03 (3H,t,J=8 Hz), 1.82 (4H,m), 2.1–2.4 (5H,m), 3.10 (1H,m), 3.30 (3H,s), 3.36 (1H,m), 3.48 (1H,d,J=12 Hz), 3.6–3.8 (2H,m), 3.82 (1H,d,J=12 Hz), 4.92 (1H,t,J=9 Hz), 7.23 (4H,s)

EXAMPLE 51

(2S,3R,4S,5R)-4-methoxy-5-[2-(morpholino)ethoxy]-2-nonyltetrahydro-2H-pyran-3-yl glycinate di-trifluoroacetic acid salt; FAB-MS: m/z 445 (MH$^+$-2CF$_3$CO$_2$H); $^1$H-NMR (CDCl$_3$)d: 0.87 (3H,t,J=7 Hz), 1.20–1.43 (16H,m), 2.95–3.34 (6H,m), 3.43 (3H,s), 3.46–3.70 (3H,m), 3.94–4.04 (12H,m), 4.74 (1H,t,J=8 Hz).

EXAMPLE 52

Preparation of (2S,3R,4S,5S)-3-[(aminoacetyl)amino]-4-methoxy-5-methyl-2-[(E)-1-nonenyl]tetrahydro-2H-pyran trifluoroacetic acid salt;

a) A mixture of (2S,3R,4S,5S)-4-methoxy-5-methyl-2-[(E)-1-nonenyl]tetrahydro-2H-pyran-3-amine (5.2 mg), N-(tert-butoxycarbonyl)glycine (10.1 mg), 4-dimethylaminopyridine (7.0 mg), and dicyclohexylcarbodiimide (12.0 mg) in dichloromethane (0.5 ml) was stirred for 2 hours at room temperature. The reaction was quenched by addition of water. The mixture was extracted with dichloromethane, and the organic layer was washed with brine, dried over anhydrous sodium sulfate, filtered, and concentrated. Purification of the residue by preparative thin layer chromatography (ethylacetate as an eluent) gave (2S, 3R,4S,5S)-3-[[(tert-butoxycarbonylamino)acetyl]amino]-4-methoxy-5-methyl-2-[(E)-1-nonenyl]tetrahydro-2H-pyran (6.3 mg, y. 79%).

b) A mixture of the above amide (6.0 mg) and trifluoroacetic acid (30 ml) in dry dichloromethane (0.3 ml) was stirred at room temperature for 1 hour. Evaporation of the solvent under reduced pressure gave (2S,3R,4S,5S)-3-[(aminoacetyl)=amino]-4-methoxy-5-methyl-2-[(E)-1-nonenyl]tetrahydro-2H-pyran trifluoroacetic acid salt as colorless oil (5.6 mg, y. 83%). EI-MS: m/z 340 (M$^+$-CF$_3$CO$_2$H); $^1$H-NMR (CDCl$_3$)d: 0.87 (3H,t, J=7 Hz), 1.10 (3H,d,J=8 Hz), 1.1–1.3 (10H,m), 1.95 (2H,m), 2.21 (1H,m), 3.0–3.8 (7H,m), 3.27 (3H,s), 5.42 (1H,m), 5.7 (1H,m).

The following compounds in Example 53–55 were obtained in a manner analogous to that of Example 52.

EXAMPLE 53

(2S,3R,4S,5S)-3-[(aminoacetyl)amino]-4-methoxy-5-methyl-2nonyltetrahydro-2H-pyran formic acid salt; FAB-MS: m/z 328 (MH$^+$-HCO$_2$H); $^1$H-NMR (CDCl$_3$)d: 0.87 (3H,t,J=7.3 Hz), 1.01 (3H,d,J=6.9 Hz), 1.24 (12H,br.s), 1.46–1.49 (4H,br.m), 2.18 (1H,m), 3.11 (1H,m), 3.21–3.30 (4H,br.m), 3.48 (1H,br.d,J=11.7 Hz), 3.76–4.05 (4H,br.m), 7.05 (3H,br.s), 7.99 (1H,br.m).

EXAMPLE 54

(1R,2S,3S)-2-[(aminoacetyl)amino-4,4-dimethyl-3-methoxy-1-octyloxycyclohexane trifluoroacetic acid salt:

Heavy syrup; FAB-MS: m/z 343 (MH$^+$-CF$_3$COOH); $^1$H-NMR (CDCl$_3$+D$_2$O) d: 0.85 (3H,s), 0.85 (3H,t,J=7 Hz), 0.95 (3H,s), 1.1–1.6 (12H,m) 1.90 (2H,m) 2.85 (1H,d,J)=11 Hz), 3.17 (1H,m), 3.3–3.6 (2H,m), 3.43 (3H,s), 3.7–4.0 (2H,m).

EXAMPLE 55

(1R,2S,3S)-2-[(aminoacetyl)amino]-4-47dimethyl-3-methoxy-1-[2-(4-methoxyphenyl)ethyl]cyclohexane trifluoroacetic acid salt;

Heavy syrup; EI-MS: m/z 348 (M$^+$-CF$_3$COOH); $^1$H-NMR (CDCl$_3$+D$_2$O)d 0.77 (3H,s), 0.90 (3H,s), 1.0–1.35 (4H,m), 1.7–1.8 (2H,m), 2.35 (1H,m), 2.67 (1H,d,J=10 Hz), 2.65 (1H,m) 3.32 (3H,s), 3.69 (3H,s), 3.6–3.9 (3H,m), 6.75 (2H,d,J=8 Hz), 7.00 (2H,d,J=8 Hz)

The following compounds starting from compounds of formula (II) in which R$^{31}$ is an amino group can also be obtained in a manner analogous to that of Example 52:

(1S,2S,3S)-2-[(aminoacetyl)amino]3-methoxy-4,4-dimethyl-1-](E)-1-nonenyl]cyclohexane, (1R,2S,3S)-2-[(aminoacetyl)amino]3-methoxy-4,4-dimethyl-1-nonylcyclohexane, (1S*,2R)-2-[(aminoacetyl)amino]amino]-4,4-dimethyl-1-nonenyl]cyclohexane, (1S*,2R*)-2-[(aminoacetyl)amino]-4,4-dimethyl-1-nonyl=cyclohexane, (1R*,2R*)-2-[(aminoacetyl)amino]-1-octyloxy-4,4-dimethyl=cyclohexane.

EXAMPLE 56

Preparation of (2S,3R,4S,5S)-3-[[(dimethylamino)acetyl]-amino]-4-methoxy-5-methyl-2-nonyltetrahydro-2H-pyran.

To a suspension of (2S,3R,4S,5S)-3-[(aminoacetyl)amino]-4-methoxy-5-methyl-2-nonyltetrahydro-2H-pyran formic acid salt (10 mg) and potassium carbonate (15 mg) in DMF (1.0 ml) methyl iodide (5 ml) was added After stirring at room temperature for 14 hr, the reaction mixture was evaporated under reduced pressure. The oily residue was partitioned between ether (2 ml) and water (2 ml). The ether layer was washed with water (1 ml) and evaporated to dryness under reduced pressure. The residue was chromatographed on silica gel using CH$_2$Cl$_2$/MeOH (8:2) as an eluent to give the crude product. The crude product was further purified by preparative TLC using AcOEt/isoPrOH as a developing solvent to give (2R,3R,4S,5S)-3-[[(dimethylamino)acetyl:]amino]-4-methoxy-5-methyl-2-nonyltetrahydro-2H-pyran (2 mg, y. 21%), as an oil; FAB-MS: m/z 357 (MH$^+$-HCO$_2$H); $^1$H-NMR (CDCl$_3$)d: 0.87 (3H,t,J=7.3 Hz), 1.00 (3H,d,J=7.3 Hz), 1.25 (12H,br.s), 1.45 (2H,m), 1.69 (2H,m), 2.15 (1H,m), 2.2 (3H,br.s), 2.25 (3H, br.s), 3.0 (1H,m), 3.1 (1H,m), 3.25–3.7 (5H,br.m), 3.36 (3H,s), 7.3 (1H, br.s).

EXAMPLE 57

Preparation of (2S,3R,4S,5S)-4-methoxy-5-methyl-2-nonyl tetrahydro-2H-pyran-3-yl methyl aminomethylphosphonate a) To a solution of (2S,3R,4S,5S)-4-methoxy-5-methyl-2-[(E)-1-nonenyl]tetrahydro-2H-pyran-3-ol (0.5 g), dimethylamino-pyridine (0.03 g) and (N-carbobenzoxyamino)methylphosphonic acid (0.7 g) in dry pyridine (30 ml) there was added 2,4,6-triiso=propyl benzenesulfonyl chloride (0.74 g). The reaction mixture was stirred for 12 hr at room temperature and evaporated to dryness under reduced pressure. The residue was partitioned between ether (50 ml) and 0.1N-HCl (50 ml). The ether layer was dried over anhydrous sodium sulfate, evaporated to dryness under reduced pressure. The resultant yellow oil was dissolved in ether (30 ml) and methanol (5 ml). 10%-trimethylsilyldiazomethane solution in hexane was added to the solution until the evolution of gas ceased. The reaction mixture was evaporated to dryness and purified by silica gel chromatography eluted with CH$_2$Cl$_2$/AcOEt (7:3) to give (2S,3R,4S,5S)-4-methoxy-5-methyl-2-[(E)-1-nonenyl]tetrahydro-2H-pyran-3-yl methyl (benzyloxy=carbonylamino)methylphosphonate (0.8 g, y. 84%) as a colorless oil; EI-MS: m/z 511 (M$^+$) b) A solution of (2S, 3R,4S,5)-4-methoxy-5-methyl-2-[(E)-1-nonenyl] tetrahydro-2H-pyran-3-yl methyl (benzyloxycarbonyl=amino)methylphosphonate (0.8 g) in methanol (20 ml) was stirred under hydrogen atmosphere in the presence of Pd-black (50 mg) at room temperature for 4 hr. The catalyst was removed by filtration and washed with methanol (10 ml×2). The combined filtrate and washings were evaporated to dryness under reduced pressure to give (2S,3R,4S,5S)-4-methoxy-5-methyl-2-nonyl=tetrahydro-2H-pyran-3-yl methyl (aminomethyl)phosphonate (0.534 g, y. 90%) as colorless oil; FAB-MS: m/z 380 (MH$^+$); $^1$H-NMR (CDCl$_3$) d: 0.88 (3H,t,J=6 Hz), 1.0 (3H,d,J=6.3 Hz), 1.24 (14H,br.s), 1.54 (1H,m), 1.7 (.1H,m), 2.31 (1H,m), 3.1–3.3 (5H,br.m), 3.37 (1.5H,s), 3.40 (1.5H,s), 3.47–3.54 (2H,m), 3.79 (1H, m), 3.85 (1.5H,d,J=12 Hz), 3.91 (1.5H,d,J=12 Hz), 4.2 (1H,m). (2S,3R,4S,5S)-4-Methoxy-5-methyl-2-nonyltetrahydro-2H-pyran-3-yl (aminomethyl)phosphonate could also be obtained by the same manner as Example 57 without O-methylation.

EXAMPLE 58

Preparation of (2S,3S,4S,5S)-3-(1H-imidazol-1-ylmethyl)-4-methoxy-5-methyl-2-[(E)-1-nonenyl] tetrahydro-2H-pyran-3-ol A mixture of (3S,4S,7S,8S)-8-methoxy-7-methyl-4-[(E)-1-nonenyl]-1,5-dioxaspiro[2.5]octane (4.2 mg) and imidazole sodium derivative (14.0 mg) in dry N,N-dimethylformamide (0.5 ml) was stirred for 15 hours at room temperature. The reaction mixture was diluted with water. The mixture was extracted with dietyl ether, the combined ethereal extracts were washed with brine, dried over anhydrous sodium sulfate, filtered and concentrated. Purification of the residue by preparative thin layer chromatography (ethyl acetate as an eluent) gave (2S,3S,4S,5S)-3-(1H-imidazol-1-ylmethyl)-4-methoxy-5-methyl-2-[(E)-1-nonenyl]tetrahydro-2H-pyran-3-ol (4.1 mg, y. 79%) as colorless oil; EI-MS: m/z 351 (M$^+$); $^1$H-NMR (CDCl$_3$)d: 0.88 (3H,t,J=8 Hz), 1.10 (3H,d,J=7 Hz), 1.2–1.5 (10H,m), 2.1 (3H,m), 2.39 (1H,br.s, —OH), 2.93 (1H,d,J=5 Hz), 3.39 (3H,s), 3.40 (1H,dd,J=3 & 12 Hz), 3.61 (1H,d,J=8 Hz), 3.76 (1H,dd,J=4 & 12 Hz), 3.96 (1H,d,J=14 Hz), 4.13 (1H,d,J=14 Hz), 5.87 (2H,m), 6.91 (1H,s), 7r14(1H,s), 7.46 (1H,s).

EXAMPLE 59

Preparation of 1-[[(2S,5R)-5,6-dihydro-5-methyl-2-nonyl-2H-pyran-3-yl]methyl]-1H-imidazole a) To a mixture of (2S,5R)-(5,6-dihydro-5-methyl-2-nonyl-2H-pyran-3-yl)methanol (10 mg) and triethylamine (17 ml) in dry dichloro-methane (0.5 ml) was added methanesulfonyl chloride (10 ml) at 0° C. The mixture was allowed to warm to room temperature, and stirred for 30 min. The reaction was quenched by the addition of aqueous saturated sodium bicarbonate solution. The resulting mixture was extracted with dichloromethane. The combined organic layers were washed with brine, dried over anhydrous sodium sulfate, filtered, and concentrated. Purification of the residue by preparative thin layer chromatography gave (2S,5R)-(5,6-dihydro-5-methyl-2-nonyl-2H-pyran-3-yl)methyl methanesulfonate (100 mg).

b) A mixture of the above sulfonate (10.0 mg) and imidazole sodium derivative (27 mg) in dry N,N-dimethylformamide (0.5 ml) was stirred for 13 hours at room temperature. The reaction mixture was diluted with water. The mixture was extracted with ether. The ethereal extracts were washed with brine, dried over anhydrous sodium sulfate, filtered, and concentrated. The residue was heated at 60° C. under reduced pressure to give a crude product, which was purified by thin layer chromatography (using ethyl acetate:methanol=10:1 as an eluent). 1-[[(2S,5R)-5,6-dihydro-5-methyl-2-nonyl-2H-pyran-3-yl]methyl]-1H-imidazole (8.3 mg, y. 91%) was obtained as colorless oil; EI-MS: m/z 304 (M$^+$); $^1$H-NMR (CDCl$_3$)d: 0.88 (3H,t,J=7 Hz), 1.00 (3H,d,J=7 Hz), 1.26 (14H,br.s), 1.40 (2H,m), 1.56 (1H,m), 3.45 (1H,dd,J=5 & 12 Hz), 3.65 (1H,dd,J=4 & 12 Hz), 3.90 (1H,d,J=7 Hz), 4.40 (1H,d,J=16 Hz), 4.49 (1H,d, J=16Hz), 5.56 (1H,d,J=4 Hz), 6.91 (1H,s), 7.10 (1H,s), 7.57 (1H,s).

The following compounds in Example 60–62 were obtained in a manner analogous to that of Example 59.

EXAMPLE 60

1-[[(2S,5R)-5,6-dihydro-5-methyl-2-[(E)-1-nonenyl]-2H-pyran-3-yl]methyl]-1H-imidazole; colorless oil; EI-MS: m/z 302 (M$^+$); $^1$H-NMR (CDCl$_3$)d: 0.88 (3H,t,J=7 Hz), 1.01 (3H,d,J=7 Hz), 1.1–1.6 (10H,m), 2.06 (2H,m), 2.33 (1H,m), 3.46 (1H,dd,J=6 & 8 Hz), 3.70 (1H,dd,J=5 & 11 Hz), 4.24 (1H,d,J=8 Hz), 4.38 (1H,d,J=16 Hz), 4.47 (1H,d,J=16 Hz), 5.45 (1H,dd,J=8 & 16 Hz), 5.69 (2H,m), 6.90 (1H,s), 7.14 (1H,s), 7.66 (1H,s).

EXAMPLE 61

1-[[(2S,5R)-5,6-dihydro-5-methyl-2-nonyl-2H-pyran-3-yl]methyl]-1H-1,2,4-triazole; colorless amorphous powder; EI-MS: m/z 305 (M$^+$); $^1$H-NMR (CDCl$_3$)d: 0.88 (3H,t,J=7 Hz), 1.02 (3H,d,J=7 Hz), 1.26 (14H,br.s), 1.40 (2H,m), 1.56 (1H,m), 3.47 (1H,dd,J=5 & 12 Hz), 3.67 (1H,dd,J=4 & 11 Hz), 3.93 (1H,t,J=6 Hz), 4.64 (1H,d,J=16 Hz), 4.76 (1H,d, J=16 Hz), 5.66 (1H,d,J=4 Hz), 7.98 (1H,s), 8.20 (1H,s).

EXAMPLE 62

1-[[(2S,5R)-5,6-dihydro-5-methyl-2-(2-naphthylethyl)-2H-pyran-3-yl]methyl]-1H-1,2,4-triazole; colorless oil; EI-MS: m/z 333 (M$^+$); $^1$H-NMR (CDCl$_3$)d: 1.06 (3H,d,J=8 Hz), 2.00 (2H,m), 2.34 (1H,br), 2.92 (2H,m), 3.54 (1H,dd, J=5 & 12 Hz), 3.74 (1H,dd,J=4 & 12 Hz), 3.98 (1H,br.s), 4.63 (1H,d,J=16 Hz), 4.75 (1H,d,J=15 Hz), 5.69 (1H,br.s), 7.36 (1H,d,J=1 Hz), 7.44 (2H,m), 7.63 (1H,s), 7.79 (3H,m), 7.93 (1H,s), 8.26 (1H,s).

EXAMPLE 63

Preparation of 1-[[(1R,2R,6S)-2-methoxy-3,3-dimethyl-6-[(E)-1-nonenyl]cyclohexyl]methyl]-1H-imidazole a) To a mixture of (1R,2R,6S)-[2-methoxy-3,3-dimethyl-6-[(E)-1-nonenyl]cyclohexyl]methanol (5 mg) and triethylamine (10 ml) in dry dichloromethane (0.5 ml), there was added methanesulfonyl chloride (4 ml) at. 0° C. The mixture was allowed to warm to room temperature, and stirred for 1 hr. The reaction was quenched by the addition of aqueous saturated sodium bicarbonate solution. The resulting mixture was extracted with dichloromethane. The combined organic layer were washed with brine, dried over anhydrous sodium sulfate, filtered and concentrated. Purification of the residue by preparative thin layer chromatography (using n-hexane:ethyl acetate=10:1 as an eluent) gave (1R,2R,6S)-[2-methoxy-3,3-dimethyl-6-[(E)-1-nonenyl]cyclohexyl]=methyl methanesulfonate (5.5 mg. y. 85%).

b) A mixture of the above sulfonate (5.5 mg) and imidazole sodium derivative (13 mg) in dry N,N-dimethylformamide (0.3 ml was stirred for 6 hrs at room temperature. The reaction mixture was diluted with water. The mixture was extracted with ether. The combined organic extracts were washed with brine, dried over anhydrous sodium sulfate, filtered, and concentrated. Purification of the residue by preparative thin layer chromatography (using ethyl acetate as an eluent) gave 1-[[(1R,2R,6S)-2-methoxy-3,3-dimethyl-6-[(E)-1-nonenyl]cyclohexyl]methyl]-1 H-imidazole (3.8 mg, y. 78%) as colorless oil; EI-MS: m/z 346 (M$^+$); $^1$H-NMR (CDCl$_3$)d: 0.78 (3H,t,J=7 Hz), 0.89 (3H,s), 1.05 (3H,s), 1.2–1.4 (15H,m), 1.7–2.0 (3H,m), 2.58 (1H,d,J=13 Hz), 3.57 (3H,s), 4.07 (1H,d,J=14 Hz), 4.16 (1H,dd,J=3 & 14 Hz), 5.16 (1H,dd,J=9 & 15 Hz), 5.51 (1H,dd,J=15 & 7 Hz), 7.15 (1H,s), 7.22 (1H,s), 7.80 (1H,s).

The following compounds in Example 64–83 were obtained in a manner analogous to that of Example 63.

EXAMPLE 64

1-[[(1R,2R,6S)-2-methoxy-3,3-dimethyl-6-[(Z)-1-nonenyl]-cyclohexyl]methyl]-1H-imidazole: colorless oil; EI-MS: m/z 346 (M$^+$); $^1$H-NMR (CDCl$_3$)d: 0.88 (3H,t,J=7 Hz), 0.90 (3H,s), 1.05 (3H,s), 1.2–1.5 (14H,m), 1.63 (.1H, m), 2.0–2.2 (3H,m), 2.64 (1H,d,J=10 Hz), 3.59 (3H,s), 3.98 (1H,dd,J=4 & 15 Hz), 4.07 (1H,dd,J=4 & 15 Hz), 5.15 (1H,dd,J=9 & 11 Hz), 5.43 (1H,dt,J=11 & 7 Hz), 6.93 (1H,s), 7.05 (1H,s), 7.53 (1H,s).

EXAMPLE 65

1-[[(1R,2R,6R)-2-methoxy-3,3-dimethyl-6-nonylcyclohexyl]-methyl]-1H-1,2,4-triazole: colorless oil;

EI-MS: m/z 349 (M⁺); ¹H-NMR (CDCl₃)d: 0.86 (3H,s), 0.88 (3H,t,J=8 Hz), 1.04 (3H,s), 1.1–1.91 (22H,m), 2.87 (1H,d,J=10 Hz), 3.63 (3H,s), 4.29 (1H,dd,J=4 & 14 Hz), 4.52 (1H,d,J=14 Hz), 8.05 (1H,m), 8.24 (1H,m).

EXAMPLE 66

1-[[(1R,2R,6R)-2-methoxy-3,3-dimethyl-6-nonylcyclohexyl]-methyl]-1H-imidazole: colorless oil; EI-MS: m/z 348 (M⁺); ¹H-NMR (CDCl₃)d: 0.87 (3H,t,J=8 Hz), 0.87 (3H,s), 1.03 (3H,s), 1.1–1.4 (20H), 1.8–2.0 (2H, m), 2.56 (1H,d,J=9 Hz), 3.58 (3H,s), 4.07 (1H,dd,J=3 & 14 Hz), 4.19 (1H,dd,J=3 & 14 Hz), 6.97 (1H,s), 7.10 (1H,s), 7.65 (1H,s).

EXAMPLE 67

(1R,2R,6S)-1-[3,3-dimethyl-2-methoxy-6-(1-methylvinyl)]-cyclohexane-1-ylmethyl-1H-imidazole colorless oil; EI-MS: m/z 262 (M⁺); ¹H-NMR (CDCl₃)d: 0.92 (3H,s), 1.05 (3H,s), 1.2–1.6 (4H,m), 1.56 (3H,s), 1.9 (2H, m), 2.63 (1H,d,J=10 Hz), 3.59 (3H, s), 3.93 (1H,dd,J=2 & 14 Hz), 4.08 (1H,dd,J=3 & 14 Hz), 4.84 (1H,br.s), 4.87 (1H, br.s), 6.94 (1H,s), 7.01 (1,H,s), 7.45 i(1H,s).

EXAMPLE 68

1-[[(1R,2R,6R)-2-methoxy -3,3-dimethyl-6-octyloxy-cyclohexyl]methyl]-1H-imidazole: colorless oil; EI-MS: m/z 350 (M⁺); ¹H-NMR (CDCl₃)d: 0.81 (3H,t,J=10 Hz), 0.83 (3H,s), 0.96 (3H,s), 1.2–1.4 (14H,m), 1.6 (1H,m), 1.7–1.9 (2H,m), 2.49 (1H,d,J=11 Hz), 2.72 (1H,dt,J=4 & 11 Hz), 3.14 (1H,dd,J=7 & 16 Hz), 3.52 (1H,m) 3.55 (3H,s), 4.15 (1H,dd,J=3 & 14 Hz), 4.21 (1H,dd,J=4 & 14 Hz), 6.90 (1H,s), 7.03 (1Hs), 7.55 (1H,s).

EXAMPLE 69

1-[[(1R,2R,6R)-2-methoxy-3,3-dimethyl-6-octyloxycyclohexyl]methyl]-1H-1,2,4-triazole: colorless oil; EI-MS: m/z 351 (M⁺); ¹H-NMR (CDCl₃)d: 0.92 (3H,t, J=10 Hz), 0.95 (3H,s), 1.07 (3H,s), 1.3–1.5 (14H,m), 1.7 (1H,m), 1.9 (2H,m), 2.64 (1H,dt,J=4 & 11 Hz), 2.92 (1H, d,J=11 Hz), 3.14 (1H,dd,J=7 & 16 Hz), 3.58 (1H,dd,J=6 & 15 Hz), 3.72 (3H,s), 4.52 (1H,d,J=14 Hz), 4.58 (1H,dd,J=4 & 14 Hz), 8.06 (1H,br.s), 8.23 (1H,br.s).

EXAMPLE 70

4-trifluoromethyl-N-[(1R,2S,3R)-3-methoxy-4,4-dimethyl-2 (1H-imidazol-1-ylmethyl)cyclohexyl] benzamide: colorless oil; EI-MS: m/z 409 (M⁺); ¹H-NMR (CDCl₃)d: 1.04 (3H,s), 1.09 (3H,s), 1.35 (1H,m), 1.47 (1H,m), 1.74–2.0 (3H,m), 2.71 (1H,br.s), 3.55 (3H,s), 4.11 (1H,m), 4.22 (2H,s), 6.86 (1H,s), 7.00 (1H,s), 7.58 (2H,d, J=7.3 Hz), 8.04 (2H,d,J=7.3 Hz), 8.04 (1H,d,J=7.3 Hz), 8.66 (1H,s).

EXAMPLE 71

1-[[(1R;2R,6R)-2-methoxy-3,3-dimethyl-6-[2-[4-N,N-dimethylamino)phenyl]ethyl]cyclohexyl]methyl]-1H-1,2,4-triazole;

Colorless heavy syrup; EI-MS: m/z 370 (M⁺) ¹H-NMR (C₆D₆)d: 0.91 (3H,S), 0.95 (3H,s), 0.87–1.00 (3H,m), 1.11–1.32 (2H,m), 1.40–1.47 (2H,m), 1.76–1.86 (1H,m), 2.23–2.32 (1H,m), 2.51–2.58 (1H,m), 2.59 (6H,s) 2.88 (1H, d,J=10.3 Hz), 3.51 (3H,s), 3.69 (1H,dd,J=4.0 & 14.7 Hz), 4.21 (1H,dd,J=2.2 & 14.7 Hz), 6.72 (2H,d,J=8 Hz), 7.10 (2H,d,J=8 Hz), 7.57 (1H,s), 7.99 (1H,s).

EXAMPLE 72

1-[[(1R,2R,6R)-6-[2-(4-chlorophenyl)ethyl]-2-methoxy-3,3-dimethylcyclohexyl]methyl]-1H-1,2,4-triazole;

Colorless heavy syrup; EI-MS: m/z 361 (M⁺); H-NMR (CDCl₃)d: 0.89 (3H,s), 1.05 (3H,s), 1.00–1.28 (3H,m), 1.33–1.40 (1H,m) 1.41–1.52 (1H,m), 1.59–1.70 (2H,m), 190–2.00 (1H,m), 2.35–2.46 (1H,m), 2.60–2.70 (1H,m), 2.86 (1H,d,J=11.0 Hz), 3.63 (3H,s), 4.28 (1H,dd,J=4.4 & 14.7 Hz), 4.48 (1H,dd,J=2.2 & 14.7 Hz), 7.09 (2H,d,J=8.1 Hz), 7.25 (2H,d), 7.96 (1H,s), 8.10 (1H s)

EXAMPLE 73

1-[[(1R,2R,6R)-6-[(4-chlorophenylthio)methyl]-2-methoxy-3,3-dimethylcyclohexyl]methyl]-1H-1,2,4-triazole;

Colorless heavy syrup;; EI-MS m/z 379 (M⁺); ¹H-NMR (CDCl₃)d: 0.91 (3H,s), 1.04 (3H,s), 1.10–1.49 (3H,m), 1.57–1.69 (2H,m), 1.93 (1H,m), 2.75 (1H,d,J=11 Hz), 3.05 /(1H,dd,J=7.4 & 12.5 Hz), 3.26 (1H,dd,J=3 & 12.5 Hz), 3.59 (3H,s), 4.25 (1H,dd,J=3.7 & 14.7 Hz), 4.50 (1H,dd,J=2.9 & 14.7 Hz), 7.26 (4H,m), 7.97 (1H,s), 8.24 (1H,s).

EXAMPLE 74

1-[]55(1R,2R,6R)-2-methoxy-3,3-dimethyl-6-[2-(4-methylphenyl)ethyl)cyclohexyl]-1H-1,2,4-triazole;

Colorless heavy syrup; EI-MS: m/z 341 (M⁺); ¹N-NMR (CDCl)d: 0.89 (3H,s), 1.05 (3H,s), 1.00–1.28 (3H,m), 1.33–1.40 (1H,m) 1.42–1.55 (1H,m), 1.60–1.70 (2H,m), 1.91–2.01 (1H,m), 2.33 (3H,s), 2.33–2.44 (1H,m), 2.61–2.71 (1H,m), 2.99 (1H,d,J=10.3 Hz), 3.64 (3H,s), 4.27 (1H,dd,J=4.0 & 14.3 Hz), 4.49 (1H,dd,J=2.6 & 14.3 Hz), 7.04–7.14 (4H,m), 7.95 (1H,s).

EXAMPLE 75

1-[[(1R,2R,6R)-2-methoxy-3,3-dimethyl-6-(2-b-naphthylethyl)cyclohexyl]methyl]-1H,1,1,4-triazole;

Colorless heavy syrupo; EI-MS: m/z 377 (M⁺); ¹H-NMR (CDCl₃)d: 0.91 (3H,s), 1.05 (3H,s), 1.08–1.42 (3H,m), 1.35–1.42 (1H,m), 1.54–1.65 (1H,m), 1.65–1.75 (2H,m), 2.04–2.15 (1H,m), 2.54–2.65 (1H,m), 2.80–2.89 (1H,m), 2.89 (1H,d,J=10.7 Hz), 3.63 (3H,s), 4.29 (1H,dd,J=4.4 & 14.6 Hz) 4.50 (1H,dd,J=2.4 & 14.6 Hz), 7.31 (1H,d,J=8.3 Hz), 7.39.749 (2H,m), 7.59 (1H,s), 7.76–7.84 (3H,m), 7.94 (1H,s) 8.09 (1H,s)

EXAMPLE 76

1-[[(1R,2R,6S)-2-methoxy-3,3-dimethyl-6-(2-quinolin-2-ylethyl)cyclohexyl]methyl]-1H,1,2,4-triazole Colorless solid: EI-MS: m/z 378 (M⁺); ¹H-NMR (CDCl3) d: 0.90 (3H,s), 1.04 (3H,s), 1.08–1.40 (4H,m), 1.50–1.83 (3H,m), 2.30–2.38 (1H,m), 2.88 (1H,d,J=10 Hz), 2.80–2.97 (1H,m), 3.05–3.18 (1H,m), 3.65 (3,H,s), 4.38 (1H,bd), 4.55 (1H,dd,J=2 & 14 Hz), 7.30 (1H,m), 7.53 (1H,m), 7.82 (1H,m) 7.77–7.84 (1H,m), 7.94 (1H,s), 8.00–8.22 (2H,m), 8.21 (1H,s).

EXAMPLE 77

1-[[(1R,2R,6R)-2-methoxy-3,3-dimethyl-6-[2-4-trifluoromethyl)phenyl]ethyl]cyclohexyl]methyl]-1H-1,2,4-triazole;

Colouless solid: EI-MS: m/z 395 (M⁺); ¹H(CDCl₃)d 0.90 (3H,s), 1.96 (3H,s), 1.06–1.29 (3H,m), 1.36–1.42 (1H,m), 1.46–1.57 (1H,m), 1.61–1.72 (2H,m), 1.98–2.08 (1H,m), 2.45–2.56 (1H,m), 2.68–2.80 (1H,m), 2.86 (1H,d,J=11 Hz), 3.63 (3H,s), 4.29 (1H,dd,J=4.4 & 14.7 Hz), 4.49 (1H,dd,J= 2.9 & 14.7 Hz), 7.28 (2H,d,J=8, 0Hz) 7.54 (2H,d,J=8, 0Hz) 7.96 (1H,s), 8.13 (1H,s).

EXAMPLE 78

1-[[(1R,2R,6R)-6-(p-trifluoromethoxyphenethyl)-2-methoxy-3,3-dimethylcyclohexyl]methyl]-1H-1,2,4-triazole;

Colorless crystal; FAB-MS: m/z 412 (MH⁺); ¹H-NMR (CDCl₃)d 0.89 (3H,s), 1.06 (3H,s), 1.1–1.3 (2H,m), 1.38 (1H,m), 1.49 (1H,m) 1.6–1.8 (2H,m), 1.9–2.1 (2H,m) 2.44 (1H,m), 2.69 (1H,m), 2.87 (1H,d,J=11 Hz), 3.64 (3H,s), 4.29 (1H,dd,J=4 & 15 Hz), 4.93 (1H,dd,J=2 & 15 Hz), 7.27 (2H,d,J=9 Hz), 7.17 (2H,d,J=9 Hz), 7.96 (1H,s), 8.13 (1H,s).

EXAMPLE 79

1-[[(1R,2R,6R)-2-methoxy-6-(p-methoxyphenethyl)-3,3-dimethylcyclohexyl]methyl]-1H,1,2,4-triazole;

Colorless crystal: EI-MS:; m/z 357 (M⁺); ¹H-NMR (CDCl₃)d: 0.89 (3H,s), 1.04,3H,s), 1.1–1.3 (2H,m), 1.36 (1H,m) 1.48 (1H,m), 1.6–1.7 (2H,m) 1.8–2.0 (2H,m), 2.37 (1H,m), 2.66 (1H,m,), 2.89 (1H,d,J=11 Hz), 3.64 (3H,s), 3.79 (3H,s), 4.27 (1H,dd,J=4 & 15 Hz), 4.49 (1H,dd,J=3 & 15 Hz,), 6.83 (2H,d,J=9 Hz), 7.08 (2H,d,J=9 Hz), 7.94 (1H,s), 8.01 (1H,s).

EXAMPLE 80

1-[[(1R,2R,6S)-6-(2,4-difluorophenethyl)-2-methoxy-3,3-dimethylcyclohexyl]methyl]-1H-1,2,4-triazole;

Colorless crystal; EI-MS: m/z 363 (M⁺); ¹H-NMR (CDCl₃)d: 0.89 (3H,s), 1.06 (3H,s), 1.1–1.5 (6H,m), 1.8–2.0 (2H,m) 2.4–2.5 (1H,m), 2.6–2.7 (1H,m), 2.93 (1H,d,J=11 Hz), 3.66 (3H,s), 4.29 (1H,dd,J=4 & 15 Hz), 4.51 (1H,d,J= 15 Hz), 6.7–6.9 (2H,m), 7.0–7.2 (1H,m), 7.93 (1H,s).

EXAMPLE 81

1-[[(1R,2R,6R)-6-(4-ethylphenyl)ethyl-2-methoxy-3,3-dimethyl-cyclohexyl]methyl]-1H-1,2,4-triazole;

Amorphos powder; EI-MS: m/z 355 (M⁺); ¹H-NMR (CDCl₃)d: 0.89 (3H,s), 1.05 (3H,s), 1.13 (1H,m), 1.22 (3H,t,J=7 Hz), 1.23 (1H,m) 1.37 (1H,dd,J=3 & 13 Hz), 1.51 (1H,m), 1.63–1.70 (2H,m), 1.98 (1H,m), 2.18 (1H,m), 2.42 (1H,m), 2.63 (2H,q,J=8 Hz), 2.69 (1H,m), 2.88 (1H,d,J=10 Hz), 3.63 (3H,s), 4.27 (1H,dd,J=4 & 14 Hz), 4.50 (1H,dd,J=2 & 15 Hz), 7.08 (2H,d,J=8 Hz), 7.13 (2H,d,J=8 Hz), 8.00 (1H,s), 8.14 (1H,s).

EXAMPLE 82

1-[[(1R,2R,6R)-2-methoxy-3,3-dimethyl-6-[2-(p-pyrrolidinophenyl)ethyl]cyclohexyl]methyl]-1H,1,2,4-triazole;

Colorless heavy syrup; EI-MS: m/z 396 (M⁺) ¹H-NMR (C₆D₆)d: 0.77–1.02 (3H,m), 0.91 (3H,s), 0.94 (3H,s), 1.11–1.34 (2H,m), 1.40–1.57 (6H,m), 1.78–1.89 (1H,m), 2.28–2.38 (1H,m), 2.55–2.66 (1H,m), 2.88 (1H,d,J=11.2 Hz), 2.98–3.06 (4H,m), 3.51 (3H,s), 3.70 (1H,brd,J=14 Hz), 4.21 (1H,brd,J=14 Hz), 6.60 (2H,d,J=8 Hz), 7.12–7.21 (2H), 7.59 (1H,s), 7.99 (1H,s).

EXAMPLE 83

1-[[(1R,2R,6R)-2-methoxy-3,3-dimethyl-6-(4-ethylphenoxy)methyl]methyl]-1H,1,2,4-triazole;

Heavy syrup; EI-MS: m/z 357 (M⁺); ¹H-NMR (CDCl₃)d: 0.94 (3H,s) 1.06 (3H,s), 1.21 (3H,t,J=8 Hz), 1.4–1.75 (5H, m), 2.59 (2H,q,J=8 Hz), 2.87 (1H,d,J=11 Hz), 3.64 (3H,s), 3.92 (1H,dd,J=4 & 10 Hz), 4.08 (1H,dd,J=4 & 10 Hz), 4.36 (1H,dd,J=4 & 14 Hz), 4.59 (1H,dd,J=3 & 14 Hz), 6.81 (2H,d,J=9 Hz), 7.11 (2H,d,J=9 Hz, 7.96 (1H,s), 8.26 (1H,s).

Starting from a compound of formula (V), the following compounds can be obtained in a manner analogous to that of Example 61.

(1R,2R,6R)-1-[[2-methoxy-3,3-dimethyl-6-(naphthylmethoxy)=cyclohexyl]methyl]-1H-imidazole, (1R,2R,6R)-1-[[2-methoxy-3,3-dimethyl-6-(naphthylmethoxy)=cyclohexyl]methyl]-1H-1,2,4-triazole, (1R,2R,6R)-1-[[2-methoxy-3,3-dimethyl-6-(2-naphthylethoxy)=cyclohexyl]methyl]-1H-imidazole, (1R,2R,6R)-1-[[2-methoxy-3,3-dimethyl-6-(2-naphthylethoxy)=cyclohexyl]methyl]-1H-1,2,4-triazole, (1R*,2S*)-1-[[5,5-dimethyl-2-[(E)-1-nonenyl]cyclohexyl]methyl]-1H-imidazole, (1R*,2S*)-1-[[5,5-dimethyl-2-[(E)-1-nonenyl]cyclohexyl]methyl]-1H-1,2,4-triazole, (1R*,2R*)-1-[[5,5-dimethyl-2-nonylcyclohexyl]methyl]-1H-imidazole, (1R*,2R*)-1-[[5,5-dimethyl-2-nonylcyclohexyl]methyl]-1H-1,2,4-triazole, (1S*,2R*)-1-[[5,5-dimethyl-2-octyloxycyclohexyl]methyl]-1H-imidazole, (1S*,2R*)-1-[[5,5-dimethyl-2-octyloxycyclohexyl]methyl]-1H-1,2,4-triazole, (1R*,2S*)-[[5,5-dimethyl-2-[(Z)-1-nonenyl]cyclohexyl]methyl]-1H-imidazole, (1R*,2S*)-[[5,5-dimethyl-2-[(Z)-1-nonenyl]cyclohexyl]methyl]-1H-1,2,4-triazole, (1R*,2S*)-[[5,5-dimethyl-2-[(E)-2-naphthylvinyl]cyclohexyl]=methyl]-1H-imidazole, (1R*,2S*)-[[5,5-dimethyl-2-[(E)-2-naphthylvinyl]cyclohexyl]=methyl]-1H-1,2,4-triazole, (1R*,2S*)-[[5,5-dimethyl-2 (2-naphthylethyl)cyclohexyl]methyl]-1H-imidazole, (1R*,2S*)-[[5,5-dimethyl-2 (2-naphthylethyl)cyclohexyl]methyl]-1H-1,2,4-triazole, (1R,2R,6R)-[[2-methoxy-3,3-dimethyl-6-(naphthylmethoxy)=cyclohexyl]methyl]-1H-imidazole, (1R,2R,6R)-[[2-methoxy-3,3-dimethyl-6-(naphthylmethoxy)=cyclohexyl]methyl]-1H-1,2,4-triazole, (1R,2R,6R)-[[2-methoxy-3,3-dimethyl-6-(2-naphthylethoxy)=cyclohexyl]methyl]-1H-imidazole, (1R,2R,6R )-[[2-methoxy-3,3-dimethyl-6-(2-naphthylethoxy)=cyclohexyl]methyl]-1H-1,2,4-triazole, (1R,2R,6R)-[[2-methoxy-3,3-dimethyl-6-(quinolylmethoxy)=cyclohexyl]methyl]-1H-imidazole, (1R,2R,6R)-[[2-methoxy-3,3-dimethyl-6-(quinolylmethoxy)=cyclohexyl]methyl]-1H-1,2,4-triazole, (1R,2R,6R)-[[2-methoxy-3,3-dimethyl-6-(2-quinolylethoxy)=cyclohexyl]methyl]-1H-imidazole, (1R,2R,6R)-[[2-methoxy-3,3-dimethyl-6-(2-quinolylethoxy)=cyclohexyl]methyl]-1H-1,2,4-triazole, (1S*,2R*)-[[5,5-dimethyl-2-(naphthylmethoxy)cyclohexyl]methyl]-1H-imidazole, (1S*,2R*)-[[5,5-dimethyl-2-(naphthylmethoxy)cyclohexyl]methyl]-1H-1,2,4-triazole, (1S*,2R*)-[[5,5-dimethyl-2-(2-naphthylethoxy)cyclohexyl]methyl]-1H-imidazole, (1S*,2R*)-[[5,5-dimethyl-2-(2-naphthylethoxy)cyclohexyl]methyl]-1H-1,2,4-triazole, (1S*,2R*)-[[5,5-dimethyl-2-(quinolylmethoxy)cyclohexyl]methyl]-1H-imidazole, (1S*,2R*)-[[5,5-dimethyl-2-(quinolylmethoxy)cyclohexyl]methyl]-1H-1,2,4-triazole, (1S*,2R*)-[[5,5-dimethyl-2-(2-quinolylethoxy)cyclohexyl]methyl]-1H-imidazole, (1S*,2R*)-[[5,5-dimethyl-2-(2-quinolylethoxy)cyclohexyl]methyl]-1H-1,2,4-triazole, 2-fluoro-4-trifluoromethyl-N-[(1R,2S,3R)-3-methoxy-4,4-dimethyl-2-(1H-1,2,4-triazol-1-ylmethyl)cyclohexyl]benzamide, 2,4-difluoro-N-[(1R,2S,3R)-3-methoxy-4,4-dimethyl-2-(1H-1,2,4-triazol-1-ylmethyl)cyclohexyl]benzamide, 2,4-dichloro-N-[(1R,2S,3R)-3-methoxy-4,4-dimethyl-2-(1H-1,2,4-triazol-1-ylmethyl)cyclohexyl]benzamide, 4-trifluoromethyl-N-[(1R,2S,3R)-3-methoxy-4,4-dimethyl-2-(1H-1,2,4-triazol-1-ylmethyl)cyclohexyl]benzamide.

EXAMPLE 84

Preparation of 1-[(1S*,2R*)-5,5-dimethyl-2-octyloxycyclohexyl]-3-amino-2-propanol a) A mixture of (1R*,2R*)-5,5-dimethyl-2-octyloxycyclohexan-1-yl-ethanal (50 mg), trimethylsilylnitrile (35 mg) and zinc iodide (5 mg) in dry benzene (1 ml) was stirred at room temperature for 1 hr. The reaction mixture was filtered, and the filtrate was concentrated to give a crude product which was directly used in the next reaction.

b) A mixture of the above TMS-cyanohydrin (25 mg) and lithium aluminum hydride (5 mg) in dry tetrahydrofuran (0.5 ml) was refluxed for 1 hr. The mixture was cooled to 0° C., treated by successive dropwise addition of 5 ml of water, 5 ml of 15% sodium hydroxide solution, and 15 ml of water. The resulting granular precipitate was filtered, and the filtrate concentrated to give a crude product, which was purified by preparative thin layer chromatography (using ethyl acetate:methanol=10:1 as a developing solvent) to give 1-[(1S*,2R*)-5,5-dimethyl-2-octyloxycyclohexyl]-3-amino-2-propanol (13 mg, 63% yield) as a colorless liquid; FAB-MS: m/z 313 (MH$^+$); $^1$H-NMR (CDCl$_3$)d: 0.88 (3H,t,J=10 Hz), 0.92 (3H,s), 0.94 (3H,s), 1.2–1.7 (20H,m), 1.95 (1H,m), 2.80 (2H,br.m), 3.2–3.4 (2H,m), 3.4 (2H,m).

Starting from a compound of formula (VI) the following compounds can be obtained in a manner analogous to that of Example 84:

3-amino-1-[(1S*,2R*)-5,5-dimethyl-2-(3-phenylpropoxy)=cyclohexyl]propan-2-ol 3-amino-1-[(1R,2R,6R)-2-methoxy-3,3-dimethyl-6-octyloxycyclo=hexyl]propan-2-ol 3-amino-1-[(1S,2R,6R)-2-methoxy-3,3-dimethyl-6-nonylcyclo=hexyl]propan-2-ol 3-amino-1-[(1R,2R,6R)-2-methoxy-3,3-dimethyl -6-(3-phenyl=propoxy)cyclohexyl]propan-2-ol.

EXAMPLE 85

Preparation of 3-amino-2-[(1S*,2R*)-5,5-dimethyl-2-octyloxycyclohexyl]-2-propanone a) A mixture of 3-amino-1-[(1S*,2R*)-5,5-dimethyl-2-octyloxycyclohexyl]-2-propanol (50 mg), S-t-butyloxycarbonyl-4,6-dimethyl-2-mercaptopyridine (46 mg) and triethylamine (20 ml) in methanol (1.5 ml) was stirred at room temperature for 2 hrs. Water was added to a reaction mixture and the mixture was partitioned between water and ether. The organic layer was washed with brine, dried over sodium sulfate, filtered, and concentrated. Purification of the residue by silica gel chromatography (using n-hexane:ethyl acetate=5.1 as an eluent) gave 3-[(tert-butoxycarbonyl)amino]-1-[(1S*,2R*)-5,5-dimethyl-2-octyloxycyclohexyl]-2-propanol (55 mg, y. 83%); EI-MS: m/z 395 (M$^+$-H$_2$O).

b) A mixture of the above alcohol (10 mg) and pyridinium dichromate (120 mg) in dichloromethane (2 ml) was stirred at room temperature for 20 hr. The reaction mixture was diluted with ether, and the mixture was filtered through a silica gel packed funnel. The filtered cake was washed with ether. The combined filtrate was evaporated to give 3-[(tert-butoxycarbonyl)amino]-1-[(1S*,2R*)-5,5-dimethyl-2-octyloxycyclohexyl]-2-propanone (7.9 mg, y. 80%), FAB-MS: m/z 412 (MH$^+$).

c) A mixture of the above ketone (6 mg) and trifluoroacetic acid (100 ml) in dichloromethane (0.5 ml) was stirred at room temperature for 1 hr. Evaporation of the mixture under reduced pressure gave 3-amino-1-[(1S*,2R*)-5,5-dimethyl-2-octyloxycyclohexyl]-2-propanone trifluoroacetic acid salt (4.4 mg, y. 71%), colorless oil; EI-MS: m/z 311 (M$^+$-CF$_3$CO$_2$H); $^1$H-NMR (CDCl$_3$)d; 0.87 (3H,t,J=7 Hz), 0.89 (3H,s), 0.96 (3H,s), 1.2–1.6 (18H,m), 1.9–2.3 (3H,m), 2.80 (1H,m), 3.19 (1H,m), 3.50 (1H,m), 3.92 (1H,br.d,J=12 Hz), 4.05 (1H,br.d,J=12 Hz).

Example A

Hard gelatin capsules each containing the following ingredients were manufactured in a conventional manner:

| | |
|---|---|
| 1[[(1R,2R,6R)-2-methoxy-3,3-dimethyl-6-octyloxycyclohexyl]methyl]-1H-imidazole | 100 mg |
| Lactose | 56 mg |
| Crystalline Cellulose | 30 mg |
| Silicic acid, Light Anhydrous | 10 mg |
| Talc | 3 mg |
| Magnesium stearate | 1 mg |
| Total | 200 mg |

Example B

Tablets each containing the following ingredients were manufactured in a conventional manner:

| | |
|---|---|
| 1-[[(1R,2R,6R)-2-methoxy-3,3-dimethyl-6-octyloxycyclohexyl]methyl]-1H-imidazole | 100 mg |
| Lactose | 60 mg |
| Corn starch | 20 mg |
| Sodium Starch Glycolate | 10 mg |
| Polyvinylpyrrolidone | 6 mg |
| Talc | 3 mg |
| Magnesium stearate | 1 mg |
| Total | 200 mg |

We claim:

1. A compound of formula

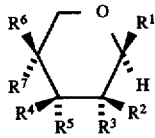

(I)

wherein R¹ is —Y-alkyl, —Y-aralkyl or —Y-aryl; Y is —O—, —CONH—, —NHCO—, —C=C—, —CH₂O—, CH₂S— or —(CH=CH)n; n is 0, 1, 2, or 3; R² is hydrogen or hydroxy; R³ is a group capable of coordinating with heme; R⁴ and R⁵ are individually hydrogen, lower alkyl, alkoxy or alkylthio, or can be taken together with the adjacent carbon atom to form a 5- or 6- membered acetal ring; R⁶ is hydrogen, lower alkyl, alkoxy or alkylthio, amino, lower alkylamino or di-lower-alkylamino; R⁷ is hydrogen, hydroxy, lower alkyl, alkoxy, or alkylthio, and may be substituted with a hydroxy, an acyl or aryl group, or a 5- or 6- membered heterocyclic ring containing as the only hetero atom one or more nitrogens, an oxygen, or a sulfur; or R⁶ and R⁷ can be taken together with the adjacent carbon atom to form a 5- or 6- membered acetal ring; or R² and R⁴ can be taken together to form a single bond; pharmaceutically acceptable salts thereof, and hydrates or solvates or their salts.

2. The compounds of claim 1, wherein —Y-alkyl comprises a straight or branched chain alkyl group having 1 to 15 carbons; —Y-aralkyl consists of an alkylene group having 1 to 5 carbons; —Y-aryl and —Y-aralkyl consists of a phenyl, naphthyl, pyridyl, quinolyl or quinoxalinyl group which may be substituted with one or more halogen atom(s), hydroxy, lower alkyl, halo-lower-alkyl, lower alkoxy, amino, or di-lower-alkylamino groups; the group capable of coordinating with heme is amino or amino-lower alkyl having 1 to 3 carbon atom(s), or 1H-imidazol-1-ylmethyl, 1H-1,2,4-triazol-1-ylmethyl, amino-acetoxy, (aminoacetyl) amino, ((lower-alkylamino)acetyl)amino, (di-lower-alkylamino)acetyl)amino, (aminomethyl)hydroxyphosphinoyloxy, ((lower-alkylamino)methy) hydroxyphosphinoyloxy, O-methyl-(aminomethyl) hydroxyphosphinoyloxy, O-methyl-((lower-alkylamino) methyl)hydroxyphosphinoyloxy, 3-amino-2-oxopropyl, 3-amino-2-hydroxypropyl, 3-(lower-alkylamino)-2-oxopropyl, 3 (di-lower-alkylamino)-2-oxopropyl, 3-(lower-alkylamino)-2-hydroxypropyl, 3-(di-lower-alkylamino)-2-hydroxypropyl or 1,3-oxazol-5-ylmethyl.

3. A compound of formula:

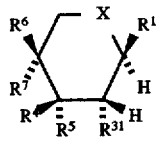

(II)

wherein R³¹ is hydroxy or amino, and R¹, R⁴, R⁵, R⁶, R⁷ are as defined in claim 1 and X is —O—.

4. A compound of formula

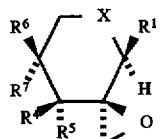

(IV)

wherein R¹, R⁴, R⁵, R⁶, R⁷ are as defined in claim 1 and X is —O—.

5. A compound of formula

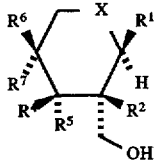

(V)

wherein R² is hydrogen, or R² and R⁴ taken together form a single bond and R¹, R⁴, R⁵, R⁶, R⁷ are as defined in claim 1 and x is —O—.

6. A compound of claim 1 having the formula:
1-[[(2S,5R)-5,6-dihydro-5-methyl-2-nonyl-2H-pyran-3-yl]methyl]-1H-imidazole.

7. The compound of claim 1 where such compound is (2S,3R,5R)-5-methyl-2-[(E)-1-nonenyl]tetrahydro-2H-pyran-3-yl glycinate.

8. The compound of claim 2 wherein said compound is (2S,3R,4S,5S)-4-ethoxy-5-methyl-2-[(Z)-1-nonenyl] tetrahydro-2H-pyran-3-yl glycinate.

9. The compound of claim 2 wherein said compound is (2S,3R,4S,5S)-5-methyl-2-[(Z)-1-nonenyl]-4-propoxytetrahydro-2H-pyran-3-yl glycinate.

10. The compound of claim 1 wherein said compound is (2S,3R,5S)-4-methoxy-5-methyl-2-[(E)-1-nonenyl] tetrahydro-2H-pyran-3-yl glycinate.

11. The compound of claim 1 wherein said compound is (2S,3R,4S,5S)-2-[(E)-1-decenyl]-4-methoxy-5-methyltetrahydro-2H-pyran-3-yl glycinate.

12. The compound of claim 1 wherein said compound is (2S,3R,4S,5S)-4-methoxy-5-methyl-2-[1E,3E,5E)-1,3,5-nonatrienyl]tetrahydro-2H-pyran-3-yl glycinate.

13. The compound of claim 1 wherein said compound is (2S,3R,4S,5S)-4-methoxy-5-methyl-2-[(1Z,3E,5E)-1,3,5,-nonatrienyl]tetrahydro-2H-pyran-3-yl glycinate.

14. The compound of claim 1 wherein said compound is (2S,3R,4S,5S)-4-methoxy-5-methyl-2-[(2)-1-nonenyl] tetrahydro-2H-pyran-3-yl glycinate.

15. The compound of claim 1 wherein said compound is (2S,3R,4S,5R)-5-butoxy-4-methoxy-2-[(E)-1-nonenyl] tetrahydro-2H-pyran-3-yl glycinate.

16. The compound of claim 1 wherein said compound is (2S,3R,4S,5R)-5-benzyloxy-4-methoxy-2-[(E)-1-nonenyl] tetrahydro-2H-pyran-3-yl glycinate.

17. The compound of claim 1 wherein said compound is (6S,7S,10S)-10-methyl-7-[(E)-1-nonenyl]-1,4,8,-trioxaspiro-[4,5]decan-6-yl glycinate.

18. The compound of claim 1 wherein said compound is (2S,3R,4S,5S)-4-methoxy-5-methyl-2-[(1E,3E)-1,3-nonadienyl]tetrahydro-2H-pyran-3-yl glycinate.

19. The compound of claim 1 wherein said compound is (2S,3R,4S,5S)-3-[(aminoacetyl)amino]-4-methoxy-5-methyl-2-[(E)-1-nonenyl]tetrahydro-2H-pyran.

20. The compound of claim 2 wherein said compound is (2S,3R,5S)-5-methyl-2-[(E)-1-nonenyl]-4-propoxytetrahydro-2H-pyran-3-yl glycinate.

21. The compound of claim 2 wherein said compound is (2S,3R,4S,5S)-5-methyl-2-nonyl-4-propoxytetrahydro-2H-pyran-3-yl glycinate.

22. The compound of claim 2 wherein said compound is (2S,3R,4S,5S)-2 (4,8-dimethylnonyl)-4-methoxy-5-methyltetrahydro-2H-pyran-3-yl glycinate.

23. The compound of claim 2 wherein said compound is (2S,3R,4S,5R)-4-methoxy-5-methyl-2-nonyltetrahydro-2H-pyran-3-yl glycinate.

24. The compound of claim 2 wherein said compound is (2S,3R,4S,5R)-4-methoxy-5-methyl-2-[(Z)-1-nonenyl] tetrahydro-2H-pyran-3-yl glycinate.

25. The compound of claim 2 wherein said compound is 1-[[(2S,5R)-5,6-dihydro-5-methyl-2-nonyl-2H-pyran-3-yl]methyl]-1H-imidazole.

26. The compound of claim 2 wherein said compound is 1-[[(2S,5R)-5,6-dihydro-5-methyl-2-nonyl-2H-pyran-3-yl]methyl]-1H-1,2,4-triazole.

27. The compound of claim 2 wherein said compound is 1-[[(2S,5R)-5,6-dihydro-5-methyl-2 (2-naphthylethyl)-2H-pyran-3-yl]methyl]-1H-1,2,4-triazole.

28. The compound of claim 2 wherein said compound is (2S,3R,4S,5S)-3-[(aminoacetyl)amino]-4-methoxy-5-methyl-2-nonenyl]tetrahydro-2H-pyran.

29. The compound of claim 2 wherein said compound is (2S,3R,4S,5S)-4-methoxy-5-methyl-2-nonyltetrahydro-2H-pyran-3-yl methyl aminomethylphosphonate.

30. The compound of claim 2 wherein said compound is (2S,3R,4S,5S)-4-methoxy-5-methyl-2-nonyltetrahydro-2H-pyran-3-yl aminomethylphosphonate.

* * * * *